US012753187B2

(12) United States Patent
Berger, Jr. et al.

(10) Patent No.: US 12,753,187 B2
(45) Date of Patent: Oct. 6, 2026

(54) AMIDO-SUBSTITUTED PYRIDYL COMPOUNDS AND METHODS OF USE THEREOF FOR THE TREATMENT OF HERPESVIRUSES

(71) Applicant: Merck Sharp & Dohme LLC, Rahway, NJ (US)

(72) Inventors: Richard Thaddeus Berger, Jr., Harleysville, PA (US); Christopher Douglas Cox, Harleysville, PA (US); Brendan M. Crowley, Collegeville, PA (US); Marc Labroli, Moorestown, NJ (US); Michael Aaron Plotkin, Frenchtown, NJ (US); Izzat Tiedje Raheem, Doylestown, PA (US); Deyou Sha, Newark, DE (US); Anthony W. Shaw, Harleysville, PA (US); Jason W. Skudlarek, Audubon, PA (US); Ling Tong, Warren, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 559 days.

(21) Appl. No.: 18/257,003

(22) PCT Filed: Dec. 14, 2021

(86) PCT No.: PCT/US2021/063183
§ 371 (c)(1),
(2) Date: Jun. 12, 2023

(87) PCT Pub. No.: WO2022/132679
PCT Pub. Date: Jun. 23, 2022

(65) Prior Publication Data

US 2024/0083910 A1 Mar. 14, 2024

Related U.S. Application Data

(60) Provisional application No. 63/127,545, filed on Dec. 18, 2020.

(51) Int. Cl.

| | |
|---|---|
| ***C07D 498/04*** | (2006.01) |
| ***A61K 31/444*** | (2006.01) |
| ***A61K 31/4545*** | (2006.01) |
| ***A61K 31/496*** | (2006.01) |
| ***A61K 31/4985*** | (2006.01) |
| ***A61K 31/501*** | (2006.01) |
| ***A61K 31/506*** | (2006.01) |
| ***A61K 31/517*** | (2006.01) |
| ***A61K 45/06*** | (2006.01) |
| ***A61P 31/12*** | (2006.01) |
| ***A61P 31/22*** | (2006.01) |
| ***C07D 401/14*** | (2006.01) |
| ***C07D 519/00*** | (2006.01) |

(52) U.S. Cl.
CPC .......... *C07D 498/04* (2013.01); *A61K 31/444* (2013.01); *A61K 31/496* (2013.01); *A61K 31/4985* (2013.01); *A61K 31/501* (2013.01); *A61K 31/506* (2013.01); *A61K 31/517* (2013.01); *A61P 31/22* (2018.01); *C07D 401/14* (2013.01); *C07D 519/00* (2013.01)

(58) Field of Classification Search
CPC .. C07D 498/04; C07D 401/14; C07D 519/00; A61K 31/444; A61K 31/496; A61K 31/4985; A61K 31/501; A61K 31/506; A61K 31/517; A61P 31/22
See application file for complete search history.

(56) References Cited

U.S. PATENT DOCUMENTS

2009/0163471 A1 6/2009 Rice et al.
2014/0099333 A1 4/2014 Schwink et al.
2019/0315708 A1 10/2019 Bao et al.

FOREIGN PATENT DOCUMENTS

JP 2007186434 A * 7/2007
WO 2002006513 A2 1/2002
(Continued)

OTHER PUBLICATIONS

Corona, Angela et al., 2-(Arylamino)-6-(trifluoromethyl)nicotinic Acid Derivatives: New HIV-1 RT Dual Inhibitors Active on Viral Replication, Molecules, 2020, 1-19, 25, 1338.
(Continued)

*Primary Examiner* — Kamal A Saeed
*Assistant Examiner* — Jalisa Holmes Ferguson
(74) *Attorney, Agent, or Firm* — Jeffrey P. Bergman; Catherine Fitch

(57) ABSTRACT

The present invention relates to novel Amido-Substituted Heterocycle Compounds of Formula (I): and pharmaceutically acceptable salts thereof, wherein $R^1$, $R^2$, $R^3$, $R^4$, and $R^5$ are as defined herein. The present invention also relates to compositions comprising at least one Amido-Substituted Heterocycle Compounds for treating or preventing a herpesvirus infection in a patient.

(I)

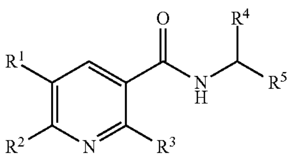

18 Claims, No Drawings

(56) References Cited

FOREIGN PATENT DOCUMENTS

| | | | |
|---|---|---|---|
| WO | 03068234 | A1 | 8/2003 |
| WO | 2004054977 | A1 | 7/2004 |
| WO | 2011117254 | A1 | 9/2011 |
| WO | 2016021742 | A1 | 2/2016 |

OTHER PUBLICATIONS

Poole, Claudette L. et al., Antiviral Therapies for Herpesviruses: Current Agents and New Directions, Clinical Therapeutics, 2018, 1282-1298, 40(8).
PUBCHEM-SID:165505553 Deposit Date: Nov. 29, 2013 (Nov. 29, 2013) pp. 1-6; p. 2.

* cited by examiner

AMIDO-SUBSTITUTED PYRIDYL COMPOUNDS AND METHODS OF USE THEREOF FOR THE TREATMENT OF HERPESVIRUSES

CROSS REFERENCE TO RELATED APPLICATIONS

This application is a U.S. National Phase application under 35 U.S.C. § 371 of PCT Application No. PCT/US2021/063183, filed Dec. 14, 2021, which claims priority from U.S. Ser. No. 63/127,545 filed Dec. 18, 2020.

FIELD OF THE INVENTION

The present invention relates to novel Amido-Substituted Pyridyl Compounds, compositions comprising at least one Amido-Substituted Pyridyl Compound, and methods of using the Amido-Substituted Pyridyl Compounds for treating or preventing herpesvirus infection in a patient.

BACKGROUND OF THE INVENTION

Human herpes viruses (Herpesviridae) are responsible for causing a wide variety of diseases in humans. Infection with herpes viruses can occur early in life and by adulthood over 95% of the population is infected by at least one herpes virus. These viruses establish a persistent life-long infection through viral latency in neuronal, lymphoid, or myeloid cells. Recurrent episodes of herpes virus disease can be triggered by numerous stimuli, including concurrent viral infections, stress, fatigue, allergies, pregnancy, sunlight or fever. Herpes virus infection in immune competent individuals generally causes mild self-limiting disease, such as: oral (HSV-1), and genital (HSV-2) ulcers, chicken pox (VZV), flu-like syndrome (CMV), and mononucleosis (EBV). In immunocompromised individuals however, primary infection with, or reactivation of an existing herpes virus infection is a major cause of disease and death. Key at-risk immunocompromised populations include patients undergoing solid organ or stem cell transplants, individuals with HIV/AIDS, and ICU patients.

Herpesviridae comprise a diverse family of double-stranded DNA viruses that are classified into three subfamilies (i.e., α, β, and γ) based upon biological characteristics such as cell tropism, diseases caused, viral life-cycle, and site of viral persistence and latency. The family consists of eight members: Herpes Simplex Virus type 1 and 2 (HSV-1, HSV-2), Varicella Zoster Virus (VZV), Epstein-Barr virus (EBV), Cytomegalovirus (CMV), and human herpes viruses 6-8 (HHV6-8).

α-herpes viruses include herpes simplex virus types 1 and 2 (HSV1 and HSV2), and varicella-zoster virus (VZV). HSV1 causes orofacial lesions, commonly known as fever blisters or cold sores. Approximately 30% of the United States population suffers from recurrent episodes of HSV1. HSV2, which is less common than HSV1, causes genital lesions. Primary infection with VZV causes varicella, commonly known as chicken pox. Reactivation of latent VZV manifests as herpes zoster or shingles. Cytomegalovirus (CMV) is a prototypical β herpes virus. Seroprevalance to CMV in the adult population is ~60%, but certain endemic areas of the world have rates closer to 100%. CMV represents the leading viral cause of morbidity and mortality in at-risk immunocompromised patients. EBV, a γ herpes virus, causes infectious mononucleosis and is responsible for lymphoid cancers such as Burkitt's and Hodgkin's lymphoma.

Presently, there is no cure for herpes. Medicines have been developed that can prevent or shorten outbreaks, but there is a need for improved therapies for treating herpes virus infection and inhibiting viral replication. The current standard of care for immunocompromised patients at risk for herpes virus disease is pre-emptive treatment with high-dose nucleoside/nucleotide analog drugs such as acyclovir, (val) ganciclovir, and cidofovir, all of which target the viral DNA polymerase. In general, current treatments are virus specific (not broad spectrum), and in the case of (val)ganciclovir and cidofovir cannot be administered prophylactically due to dose-related toxicities including bone marrow suppression and renal toxicity. Although efficacious in many settings, the current nucleos(t)ide drugs are also limited by drug-resistant viral variants and existing cross-resistant variants which may lead to treatment failure. Therefore, there is an urgent medical need for improved, well-tolerated anti-herpes agents.

SUMMARY OF THE INVENTION

In one aspect, the present invention provides Compounds of Formula (I)

(I)

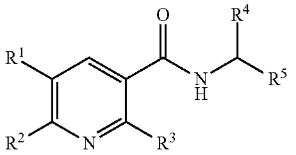

or a pharmaceutically acceptable salt thereof, wherein:

$R^1$ is —O-(5 or 6-membered monocyclic heterocycloalkyl), or —O-(9 or 10-membered bicyclic heterocycloalkyl), wherein said 5 or 6-membered monocyclic heterocycloalkyl group, and said 9 or 10-membered bicyclic heterocycloalkyl group, may each be optionally substituted with one or more R A groups, which can be the same or different;

$R^2$ is selected from H, $C_1$-$C_6$ alkyl, $C_1$-$C_6$ hydroxyalkyl, —($C_1$-$C_6$ alkylene)$_m$-N($R^4$)$_2$, $C_3$-$C_6$ monocyclic cycloalkyl, 6 to 10-membered bicyclic cycloalkyl, 3 to 7-membered monocyclic heterocycloalkyl, 6 to 10-membered bicyclic heterocycloalkyl, —($C_1$-$C_6$ alkylene)$_m$-(5 or 6-membered monocyclic heteroaryl), and 9 or 10-membered bicyclic heteroaryl, wherein said $C_3$-$C_6$ monocyclic cycloalkyl group, said 6 to 10-membered bicyclic cycloalkyl group, said 3 to 7-membered monocyclic heterocycloalkyl group, said 6 to 10-membered bicyclic heterocycloalkyl group, said 5 or 6-membered monocyclic heteroaryl group, and said 9 or 10-membered bicyclic heteroaryl group may each be optionally substituted with one or more $R^B$ groups, which can be the same or different;

$R^3$ is —O—($C_1$-$C_6$ alkyl), —($C_1$-$C_6$ alkylene)-O—($C_1$-$C_6$ alkyl), —O—($C_1$-$C_6$ hydroxyalkyl), —O—($C_1$-$C_6$ cyanoalkyl), —O—($C_1$-$C_6$ alkylene)-($C_3$-$C_7$ cycloalkyl), —O—($C_1$-$C_6$ alkylene)-N($R^4$)$_2$, —O—($C_1$-$C_6$ alkylene)-C(O)N($R^4$)$_2$, —O—($C_1$-$C_6$ haloalkyl), —O—($C_1$-$C_6$ alkylene)-(3 to 7-membered monocyclic heterocycloalkyl), —O—($C_1$-$C_6$ alkylene)-(5 or 6-membered monocyclic heteroaryl), wherein said 3 to 7-membered monocyclic heterocycloalkyl group, said 5 or 6-membered monocyclic heteroaryl group, and said 3 to 7 membered cycloalkyl group may each be optionally substituted with one or more $R^D$ groups, which can be the same or different;

each occurrence of $R^4$ is independently H or $C_1$-$C_6$ alkyl;

$R^5$ is phenyl, which may be optionally substituted with one or more $R^C$ groups, which can be the same or different each occurrence of $R^A$ is independently selected from $C_1$-$C_6$ alkyl, oxo, and —C(O)—$C_1$-$C_6$ alkyl;

each occurrence of $R^B$ is independently selected from $C_1$-$C_6$ alkyl, —O—($C_1$-$C_6$ alkyl), —OH, oxo, halo, —C(O)H, $C_1$-$C_6$ haloalkyl, $C_1$-$C_6$ hydroxyalkyl, $C_3$-$C_6$ monocyclic cycloalkyl, —($C_1$-$C_6$ alkylene)$_m$-(5 or 6-membered monocyclic heteroaryl), —($C_1$-$C_6$ alkylene)$_m$-N($R^4$)$_2$, —($C_1$-$C_6$ alkylene)$_m$-C(O)N($R^4$)$_2$, and —($C_1$-$C_6$ alkylene)-O—($C_1$-$C_6$ alkyl);

$R^C$ represents up to 3 optional phenyl group substituents, which can be the same or different, and are each independently selected from $C_1$-$C_6$ alkyl, halo, —$C_1$-$C_6$ haloalkyl, and —CN;

each occurrence of $R^D$ is independently selected from $C_1$-$C_6$ alkyl, oxo, halo, —$C_1$-$C_6$ haloalkyl, and —CN; and each occurrence of m is independently 0 or 1.

The Compounds of Formula (I) (also referred to herein as the "Amido-Substituted Pyridyl Compounds"), and pharmaceutically acceptable salts thereof can be useful, for example, for inhibiting herpesvirus viral replication or activity, and for treating or preventing herpesvirus infection in a patient. Without being bound by any specific theory, it is believed that the Amido-Substituted Pyridyl Compounds inhibit herpesvirus viral replication by inhibiting herpesvirus polymerase.

Accordingly, the present invention provides methods for treating or preventing herpesvirus infection in a patient, comprising administering to the patient an effective amount of at least one Amido-Substituted Pyridyl Compound.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to novel Amido-Substituted Pyridyl Compounds, compositions comprising at least one Amido-Substituted Pyridyl Compound, and methods of using the Amido-Substituted Pyridyl Compounds for treating or preventing herpesvirus infection in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "patient" is a human or non-human mammal. In one embodiment, a patient is a human.

The term "effective amount" as used herein, refers to an amount of Amido-Substituted Pyridyl Compound and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to a herpesvirus viral infection or herpesvirus-virus related disorder, refers to reducing the likelihood of herpesvirus infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, $—NH_2$, —NH(alkyl), $—N(alkyl)_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include $—CH_2—$, $—CH_2CH_2—$, $—CH_2CH_2CH_2—$, $—CH_2CH_2CH_2CH_2—$, $—CH(CH_3)CH_2CH_2—$, $—CH(CH_3)—$ and $—CH_2CH(CH_3)CH_2—$. In one embodiment, an alkylene group has from 1 to about 6 carbon atoms. In another embodiment, an alkylene group is branched. In another embodiment, an alkylene group is linear. In one embodiment, an alkylene group is $—CH_2—$. The term "$C_1$-$C_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group may be optionally substituted with one or more "ring system substituents" which may be the same or different and are as defined herein below. In one embodiment, an aryl group may be optionally fused to a cycloalkyl or cycloalkanoyl group. Non-limiting examples of aryl groups include phenyl and naphthyl. In one embodiment, an aryl group is phenyl. In another embodiment, an aryl group is napthalene. Unless otherwise indicated, an aryl group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group may be optionally substituted with one or more "ring system substituents" which may be the same or different and are as defined herein below. Unless otherwise indicated, a cycloalkyl group is unsubstituted. In one embodiment, a cycloalkyl group is unsubstituted. The term "3 to 6-membered cycloalkyl" refers to a cycloalkyl group having from 3 to 6 ring carbon atoms. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

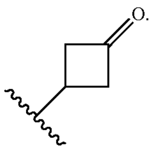 [SMILES: *C1CC(=O)C1]

The term "cycloalkenyl," as used herein, refers to a non-aromatic mono- or multicyclic ring system comprising from about 4 to about 10 ring carbon atoms and containing at least one endocyclic double bond. In one embodiment, a cycloalkenyl contains from about 4 to about 7 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group may be optionally substituted with one or more "ring system substituents" which may be the same or different and are as defined herein below. A ring carbon atom of a cycloalkyl group may be functionalized as a carbonyl group. Unless otherwise indicated, a cycloalkenyl group is unsubstituted. In one embodiment, a cycloalkenyl group is cyclopentenyl. In another embodiment, a cycloalkenyl group is cyclohexenyl. The term "4 to 6-membered cycloalkenyl" refers to a cycloalkenyl group having from 4 to 6 ring carbon atoms.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include $—CH_2F$, $—CHF_2$, $—CF_3$, $—CH_2Cl$ and $—CCl_3$.

The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include $—CH_2OH$, $—CH_2CH_2OH$, $—CH_2CH_2CH_2OH$ and $—CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic and had 9 or 10 ring atoms. A heteroaryl group may be optionally substituted by one or more "ring system substituents" which may be the same or different and are as defined herein below. A heteroaryl group is joined via a ring carbon atom, and any nitrogen atom of a heteroaryl may be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. Unless otherwise indicated, a heteroaryl group is unsubstituted. In one embodiment, a heteroaryl group is a 5-membered heteroaryl. In another embodiment, a heteroaryl group is a 6-membered heteroaryl. In another embodiment, a "9- or 10-membered bicyclic heteroaryl" group comprises a 5- to 6-membered heterocycloalkyl group fused to a benzene ring, such as:

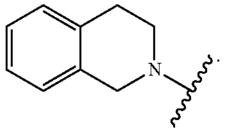 [SMILES: *N1CCc2ccccc2C1]

In still another embodiment, a "9- or 10-membered bicyclic heteroaryl" group comprises a 5- to 6-membered heteroaryl group fused to a cycloalkyl ring or a heterocycloalkyl ring, such as:

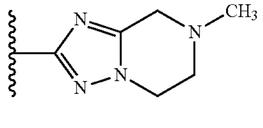

and

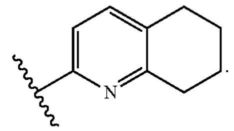

The term "heteroarylene," as used herein, refers to a bivalent group derived from an heteroaryl group, as defined above, by removal of a hydrogen atom from a ring carbon or ring heteroatom of a heteroaryl group. A heteroarylene group can be derived from a monocyclic or multicyclic ring system comprising about 5 to about 14 ring atoms, wherein from 1 to 4 of the ring atoms are each independently O, N or S and the remaining ring atoms are carbon atoms. A heteroarylene group may be optionally substituted by one or more "ring system substituents" which may be the same or different and are as defined herein below. A heteroarylene group is joined via a ring carbon atom or by a nitrogen atom with an open valence, and any nitrogen atom of a heteroarylene may be optionally oxidized to the corresponding N-oxide. The term "heteroarylene" also encompasses a heteroarylene group, as defined above, which is fused to a benzene ring. Non-limiting examples of heteroarylenes include pyridylene, pyrazinylene, furanylene, thienylene, pyrimidinylene, pyridonylene (including those derived from N-substituted pyridonyls), isoxazolylene, isothiazolylene, oxazolylene, oxadiazolylene, thiazolylene, pyrazolylene, thiophenylene, furazanylene, pyrrolylene, triazolylene, 1,2,4-thiadiazolylene, pyrazinylene, pyridazinylene, quinoxalinylene, phthalazinylene, oxindolylene, imidazo[1,2-a]pyridinylene, imidazo[2,1-b]thiazolylene, benzofurazanylene, indolylene, azaindolylene, benzimidazolylene, benzothienylene, quinolinylene, imidazolylene, benzimidazolylene, thienopyridylene, quinazolinylene, thienopyrimidylene, pyrrolopyridylene, imidazopyridylene, isoquinolinylene, benzoazaindolylene, 1,2,4-triazinylene, benzothiazolylene and the like, and all isomeric forms thereof. The term "heteroarylene" also refers to partially saturated heteroarylene moieties such as, for example, tetrahydroisoquinolylene, tetrahydroquinolylene, and the like. Unless otherwise indicated, a heteroarylene group is unsubstituted. A heteroarylene group is divalent and unless specified otherwise, either available bond on a heteroarylene ring can connect to either group flanking the heteroarylene group. For example, the group "A-heteroarylene-B," wherein the heteroarylene group is:

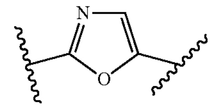 [SMILES: *c1cnc(*)o1]

is understood to represent both:

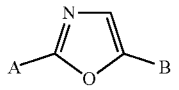

and

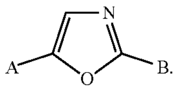

In one embodiment, a heteroarylene group is a monocyclic heteroarylene group or a bicyclic heteroarylene group. In another embodiment, a heteroarylene group is a monocyclic heteroarylene group. In another embodiment, a heteroarylene group is a bicyclic heteroarylene group. In still another embodiment, a heteroarylene group has from about 5 to about 10 ring atoms. In another embodiment, a heteroarylene group is monocyclic and has 5 or 6 ring atoms. In another embodiment, a heteroarylene group is bicyclic and has 9 or 10 ring atoms. In another embodiment, a heteroarylene group is a 5-membered monocyclic heteroarylene. In another embodiment, a heteroarylene group is a 6-membered monocyclic heteroarylene. In another embodiment, a bicyclic heteroarylene group comprises a 5 or 6-membered monocyclic heteroarylene group fused to a benzene ring. In still another embodiment, a heteroaryl group comprises a 5- to 6-membered monocyclic heteroarylene group fused to a cycloalkyl ring or a heterocycloalkyl ring.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(CBz), —N(Tos) group and the like; such protected heterocycloalkyl groups are considered part of this invention. A heterocycloalkyl group may be optionally substituted by one or more "ring system substituents" which may be the same or different and are as defined herein below. The nitrogen or sulfur atom of the heterocycloalkyl may be optionally oxidized to the corresponding N-oxide, S-oxide or S,S-dioxide. Unless otherwise indicated, a heterocycloalkyl group is unsubstituted. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

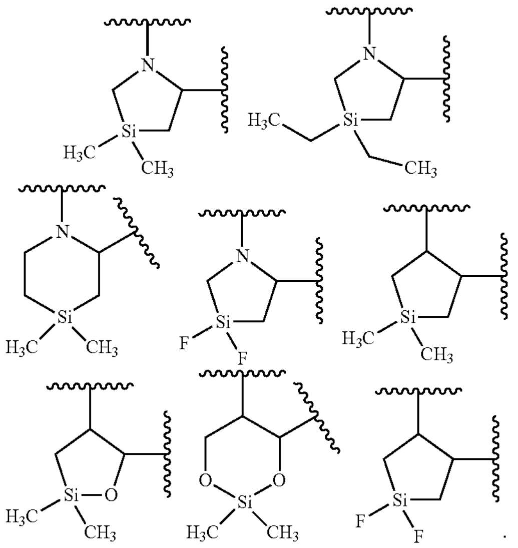

A ring carbon atom of a heterocycloalkyl group may be functionalized as a carbonyl group. Illustrative examples of such a heterocycloalkyl group include, but are not limited to:

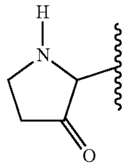

and

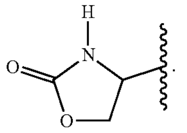

A ring sulfur atom of a heterocycloalkyl group may also be functionalized as a sulfonyl group. An example of such a heterocycloalkyl group is:

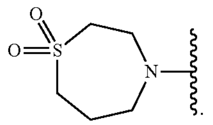 [SMILES: *N1CCCS(=O)(=O)CC1]

In one embodiment, a heterocycloalkyl group is a 5-membered monocyclic heterocycloalkyl. In another embodiment, a heterocycloalkyl group is a 6-membered monocyclic heterocycloalkyl. The term "5- to 7-membered monocyclic cycloalkyl" refers to a monocyclic heterocycloalkyl group having from 5 to 5 ring atoms. The term "4 to 6-membered monocyclic cycloalkyl" refers to a monocyclic heterocycloalkyl group having from 4 to 6 ring atoms. The term "9 to 10-membered bicyclic heterocycloalkyl" refers to a bicyclic heterocycloalkyl group having from 9 to 10 ring atoms.

The term "heterocycloalkenyl," as used herein, refers to a heterocycloalkyl group, as defined above, wherein the heterocycloalkyl group contains from 4 to 10 ring atoms, and at least one endocyclic carbon-carbon or carbon-nitrogen double bond. A heterocycloalkenyl group can be joined via a ring carbon or ring nitrogen atom. In one embodiment, a heterocycloalkenyl group has from 4 to 6 ring atoms. In another embodiment, a heterocycloalkenyl group is monocyclic and has 5 or 6 ring atoms. In another embodiment, a heterocycloalkenyl group is bicyclic. A heterocycloalkenyl group can optionally substituted by one or more ring system substituents, wherein "ring system substituent" is as defined above. The nitrogen or sulfur atom of the heterocycloalkenyl may be optionally oxidized to the corresponding N-oxide, S-oxide or S,S-dioxide. A ring carbon atom of a heterocycloalkenyl group may be functionalized as a carbonyl group. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like and the like. In one embodiment, a heterocycloalkenyl group is a 5-membered heterocycloalkenyl. In another embodiment, a heterocycloalkenyl group is a 6-membered heterocycloalkenyl. The term "4 to 6-membered heterocycloalkenyl" refers to a heterocycloalkenyl group having from 4 to 6 ring atoms. Unless otherwise indicated, a heterocycloalkenyl group is unsubstituted.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in Organic Synthesis (1991), Wiley, New York.

Examples of "ring system substituents" include, but are not limited to, alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, $—NO_2$, —CN, $—SF_5$, —C(O)OH, —C(O)O-alkyl, —C(O)O-aryl, —C(O)O-alkylene-aryl, —S(O)-alkyl, $—S(O)_2$-alkyl, —S(O)-aryl, $—S(O)_2$-aryl, —S(O)-heteroaryl, $—S(O)_Z$-heteroaryl, —S-alkyl, —S-aryl, —S-heteroaryl, —S-alkylene-aryl, —S-alkyleneheteroaryl, $—S(O)_2$-alkylene-aryl, $—S(O)_2$-alkylene-heteroaryl, $—Si(alkyl)_2$, $—Si(aryl)_2$, $Si(heteroaryl)_2$-Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—$NH_2$, —C(=NH)—$NH_2$, —C(=NH)—NH(alkyl), $—N(Y^1)(Y^2)$, -alkylene-$N(Y^1)(Y^2)$, $—C(O)N(Y^1)(Y^2)$, and $—S(O)_2N(Y^1)(Y^2)$, wherein $Y^1$ and $Y^2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moieties are methylenedioxy, ethylenedioxy, $—C(CH_3)_2—$ and the like which form moieties such as, for example:

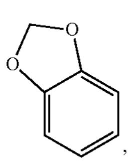,
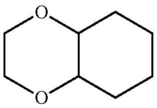
and
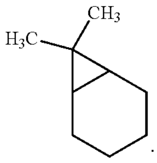.

When any substituent or variable (e.g., $R^1$, m, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g., a drug precursor) that is transformed in vivo to provide an Amido-Substituted Pyridyl Compound or a pharmaceutically acceptable salt or solvate of the compound. The transformation may occur by various mechanisms (e.g., by metabolic or chemical processes), such as, for example, through hydrolysis in blood.

For example, if an Amido-Substituted Pyridyl Compound or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 6 carbon atoms, 1-methyl-1-(alkoxycarbonyloxy) ethyl having from 5 to 8 carbon atoms, N-(alkoxycarbonyl)aminomethyl having from 3 to 9 carbon atoms, 1-(N-(alkoxycarbonyl) amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl, and the like.

Similarly, if an Amido-Substituted Pyridyl Compound contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkyl, α-amino$(C_1-C_4)$alkylene-aryl, arylacyl and α-aminoacyl, or α-aminoacyl-α-aminoacyl, where each α-aminoacyl group is independently selected from the naturally occurring L-amino acids, $—P(O)(OH)_2$, $—P(O)(O(C_1-C_6)alkyl)_2$ or glycosyl (the radical resulting from the removal of a hydroxyl group of the hemiacetal form of a carbohydrate), and the like.

If an Amido-Substituted Pyridyl Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C_3-C_7)$ cycloalkyl, benzyl, a natural α-aminoacyl, $—C(OH)C(O)OY^1$ wherein $Y^1$ is H, $(C_1-C_6)$alkyl or benzyl, $—C(OY^2)Y^3$ wherein $Y^2$ is $(C_1-C_4)$ alkyl and $Y^3$ is $(C_1-C_6)$alkyl; carboxy $(C_1-C_6)$alkyl; amino$(C_1-C_4)$alkyl or mono-N— or di-N,N—$(C_1-C_6)$alkylaminoalkyl; $—C(Y^4)Y^5$ wherein $Y^4$ is H or methyl and $Y^5$ is mono-N— or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—$(C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di $(C_{6-24})$acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.,* 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.,* 5(1), article 12 (2004); and A. L. Bingham et al, *Chem. Commun.,* 603-604 (2001). A typical, non-limiting, process involves dissolving the inventive compound in desired amounts of the desired solvent (organic or water or mixtures thereof) at a higher than room temperature and cooling the solution at a rate sufficient to form crystals which are then isolated by standard methods. Analytical techniques such as, for example IR spectroscopy, show the presence of the solvent (or water) in the crystals as a solvate (or hydrate).

The Amido-Substituted Pyridyl Compounds can form salts which are also within the scope of this invention. The term "salt(s)", as employed herein, denotes acidic salts formed with inorganic and/or organic acids, as well as basic salts formed with inorganic and/or organic bases. In addition, when an Amido-Substituted Pyridyl Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting an Amido-Substituted Pyridyl Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Stereochemically pure compounds may also be prepared by using chiral starting materials or by employing salt resolution techniques. Also, some of the Amido-Substituted Pyridyl Compounds may be atropisomers (e.g., substituted biaryls), and are considered as part of this invention. Enantiomers can also be directly separated using chiral chromatographic techniques.

It is also possible that the Amido-Substituted Pyridyl Compounds may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If an Amido-Substituted Pyridyl Compound incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$), and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Amido-Substituted Pyridyl Compounds, and of the salts, solvates, hydrates, esters and prodrugs of the Amido-Substituted Pyridyl Compounds, are intended to be included in the present invention.

The following abbreviations are used below and have the following meanings: AcOH is acetic acid; n-$Ad_2$(n-Bu)P palladacycle G2 is Chloro[(di(1-adamantyl)-N-butylphosphine)-2-(2-aminobiphenyl)]palladium(II); ATCC is American Type Culture Collection; n-BuLi is n-butyllithium, sec-BuLi is secondary butyllithium; DBAD is di-tert-butyl azodicarboxylate; DIEA is diisopropylethylamine; DMF is N,N-dimethylformamide; DMSO is dimethylsulfoxide; EDTA is ethylenediaminetetraacetic acid; ESI is electrospray ionization; EtOAc is ethyl acetate; EtOH is ethanol; $Et_3N$ is triethylamine; HATU is 1-[Bis(dimethylamino)methylene]-1H-1,2,3-triazolo[4,5-b]pyridinium 3-oxid hexafluorophosphate; HEPES is 2-[4-(2-hydroxyethyl)piperazin-1-yl]ethanesulfonic, acid; HPLC is high performance liquid chromatography; iPrOH is isopropanol; (Ir[DF($CF_3$)PPY]$_2$(DTBPY))$PF_6$ is [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate; LCMS is liquid chromatography/mass spectrometry; LED is light-emitting diode; Me is methyl; MeCN is acetonitrile; MeOH is methanol; MS is mass spectrometry; $PdCl_2$(dppf) is [1,1'-Bis(diphenylphosphino) ferrocene]dichloropalladium(II); PSI is pounds/square inch; SFC is supercritical fluid chromatography; t-butyl is tertiary butyl; TFA is trifluoroacetic acid; THF is tetrahydrofuran; TLC is thin-layer chromatography; and TMEDA is N,N,N',N'-tetramethylethylenediamine.

The Compounds of Formula (I)

The present invention provides Amido-Substituted Pyridyl Compounds of Formula (I):

(I)

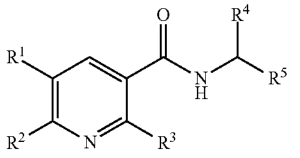

and pharmaceutically acceptable salts thereof, wherein $R^1$, $R^2$, $R^3$, $R^4$, and $R^5$ are as defined above for the Compounds of Formula (I)

In one embodiment, $R^1$ is selected from:

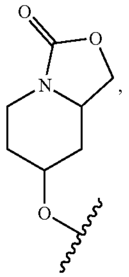
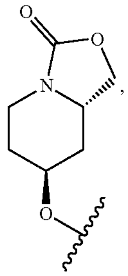
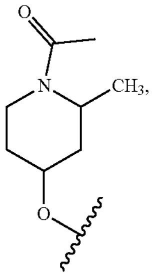
and
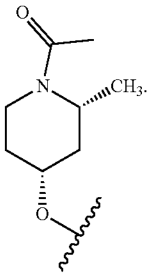

In another embodiment, $R^1$ is

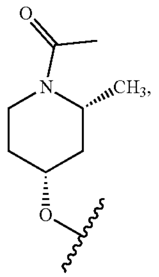
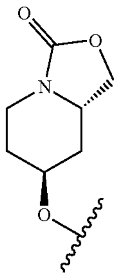
or
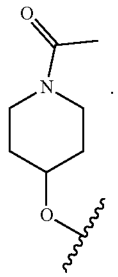

In another embodiment, $R^1$ is

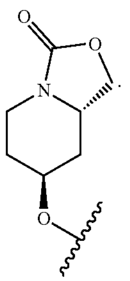 [SMILES: *O[C@H]1CCN2C(=O)OC[C@@H]2C1]

In another embodiment, $R^1$ is

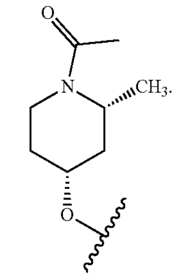 [SMILES: *O[C@@H]1CCN(C(C)=O)[C@H](C)C1]

In one embodiment, $R^2$ is selected from $C_1$-$C_6$ hydroxyalkyl, —($C_1$-$C_6$ alkylene)$_m$-N($R^4$)$_2$, $C_3$-$C_6$ monocyclic cycloalkyl, 6 to 10-membered bicyclic cycloalkyl, 3 to 7-membered monocyclic heterocycloalkyl, 6 to 10-membered bicyclic heterocycloalkyl, —($C_1$-$C_6$ alkylene)$_m$-(5 or 6-membered monocyclic heteroaryl), and 9 or 10-membered bicyclic heteroaryl, wherein said $C_3$-$C_6$ monocyclic cycloalkyl group, said 6 to 10-membered bicyclic cycloalkyl group, said 3 to 7-membered monocyclic heterocycloalkyl group, said 6 to 10-membered bicyclic heterocycloalkyl group, said 5 or 6-membered monocyclic heteroaryl group, and said 9 or 10-membered bicyclic heteroaryl group may each be optionally substituted with one or more $R^B$ groups, which can be the same or different;

In another embodiment, $R^2$ is selected from H, methyl, —$CH_2C(CH_3)_2NH_2$, $CH_2C(CH_3)_2OH$, pyrazolyl, furanyl, benzofuranyl, indolyl, pyridyl, azetidinyl, pyrrolidinyl, isoxazolyl, thiphenyl, thiazolyl, pyridizanyl, pyrimidinyl, cyclopropyl, cyclobutyl, oxazolyl, spiro[3,3]heptane, 1,2,4-oxadiazolyl, 1,3,4-thiadiazolyl,

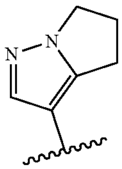,
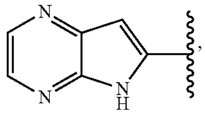,
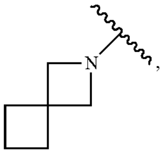,
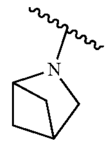, and
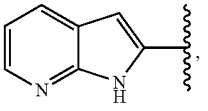, wherein said pyrazolyl, furanyl, benzofuranyl, indolyl, pyridyl, azetidinyl, pyrrolidinyl, isoxazolyl, thiphenyl, thiazolyl, pyridizanyl, pyrimidinyl, cyclopropyl, cyclobutyl, oxazolyl, spiro[3,3]heptane, 1,2,4-oxadiazolyl, 1,3,4-thiadiazolyl,

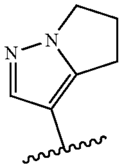,
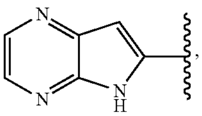,
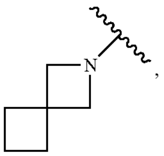,

-continued

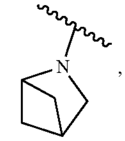, and
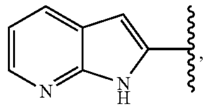, may be optionally substituted with up to three groups, which can be the same or different, and are selected from —$CHF_2$, methyl, ethyl, cyclopropyl, —OH, C(O)H, pyrazolyl, —$CH_2$-pyridyl, —$NH_2$, F, —$CF_3$, —$CH_2OH$, —$CH_2CH_2OH$, —$CH_2CH_2OCH_3$, methoxy, and —C(OH)($CH_3$)$_2$.

In still another embodiment, $R^2$ is selected from:

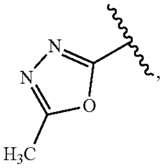,
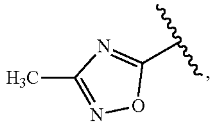,
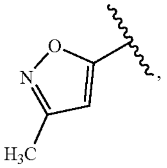,
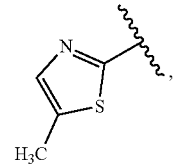,
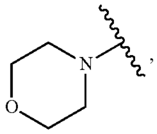,
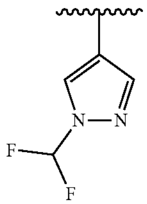,
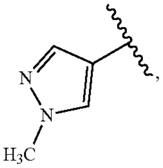,
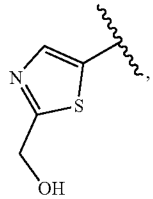,
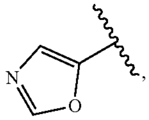, and
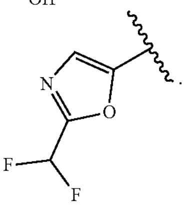.

In another embodiment, $R^2$ is:

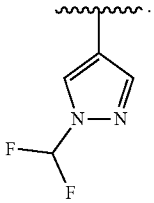

In one embodiment, $R^3$ is selected from methoxy, ethoxy, —$OCH_2CH_2OH$, —$OCH_2CH_2OCH_3$, —$OCH_2CH_2N(CH_3)_2$, —$OCH_2C(OH)(CH_3)_2$, —$OCH_2CH_2F$, —$OCH_2C(CN)(CH_3)_2$, —$OCH_2CH(CH_3)OH$, —$OCH_2CH_2CH_2N(CH_3)_2$, —$OCH_2C(CN)(CH_3)_2$, —$OCH_2CH(OH)(CH_3)$, —$OCH_2CH_2N(CH_2CH_3)_2$, —$OCH_2CH_2C(O)NH_2$,

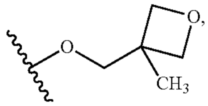 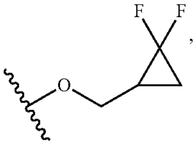

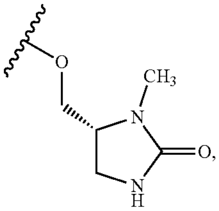 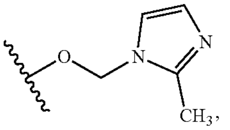

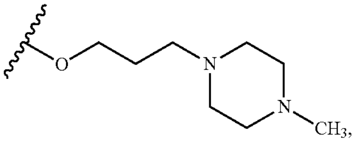 and

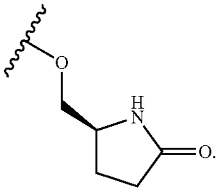

In another embodiment, $R^3$ is —O—($C_1$-$C_6$ alkyl).

In still another embodiment, $R^3$ is methoxy.

In one embodiment, $R^4$ is H, methyl, or ethyl.

In another embodiment, $R^4$ is H.

In another embodiment, $R^4$ is methyl.

In one embodiment, $R^5$ is selected from:

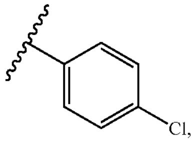 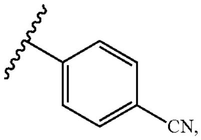

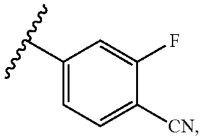 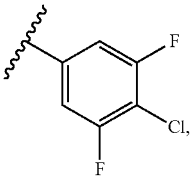

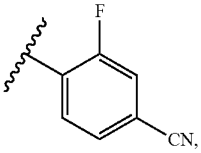 and 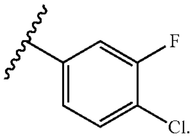

In another embodiment, $R^5$ is:

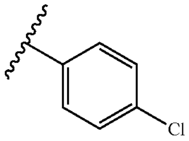 or 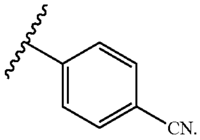

In another embodiment, $R^5$ is:

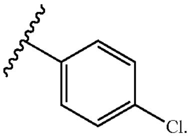 [SMILES: *c1ccc(Cl)cc1]

The compound of claim 1, or a pharmaceutically acceptable salt thereof wherein:

In one embodiment, the invention provides compounds of formula (I), and pharmaceutically acceptable salts thereof, wherein:

$R^1$ is:

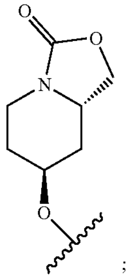 [SMILES: *O[C@H]1CCN2C(=O)OC[C@@H]2C1]

;

$R^2$ is selected from H, methyl, —$CH_2C(CH_3)_2NH_2$, $CH_2C(CH_3)_2OH$, pyrazolyl, furanyl, benzofuranyl, indolyl, pyridyl, azetidinyl, pyrrolidinyl, isoxazolyl, thiphenyl, thiazolyl, pyridizanyl, pyrimidinyl, cyclopropyl, cyclobutyl, oxazolyl, spiro[3,3]heptane, 1,2,4-oxadiazolyl, 1,3,4-thiadiazolyl,

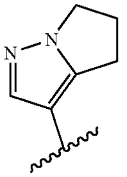, 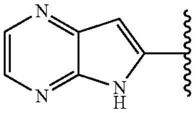, 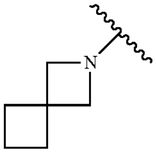,

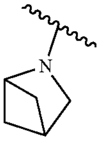, and 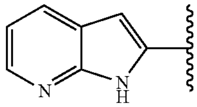, wherein said pyrazolyl, furanyl, benzofuranyl, indolyl, pyridyl, azetidinyl, pyrrolidinyl, isoxazolyl, thiphenyl, thiazolyl, pyridizanyl, pyrimidinyl, cyclopropyl, cyclobutyl, oxazolyl, spiro[3,3]heptane, 1,2,4-oxadiazolyl, 1,3,4-thiadiazolyl,

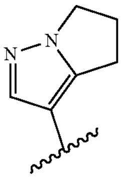, 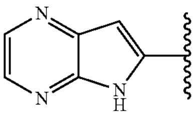, 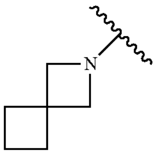,

-continued

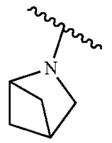

, and

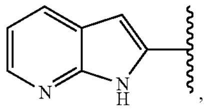

, may be optionally substituted with up to three groups, which can be the same or different, and are selected from —$CHF_2$, methyl, ethyl, cyclopropyl, —OH, C(O)H, pyrazolyl, —$CH_2$-pyridyl, —$NH_2$, F, —$CF_3$, —$CH_2OH$, —$CH_2CH_2OH$, —$CH_2CH_2OCH_3$, methoxy, and —C(OH)$(CH_3)_2$; and $R^3$ is —O—($C_1$-$C_6$ alkyl).

It is understood that the present invention includes any combination of two or more of the above embodiments.

It is understood that the present invention encompasses compounds of formula (I) in isolated and purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of anti-herpes agents and immunomodulators.

(c) The pharmaceutical composition of (b), wherein the anti-herpes agent is selected from the group consisting of herpesvirus polymerase inhibitors, and CMV terminase inhibitors.

(d) A pharmaceutical combination that is (i) a Compound of Formula (I), and (ii) a second therapeutic agent selected from the group consisting of anti-herpes agents and immunomodulators; wherein the Compound of Formula (I), and the second therapeutic agent are each employed in an amount that renders the combination effective for inhibiting herpesvirus replication, or for treating herpesvirus infection and/or reducing the likelihood or severity of symptoms of herpesvirus infection.

(e) The combination of (d), wherein the anti-herpes agent is selected from the group consisting of herpesvirus polymerase inhibitors, and CMV terminase inhibitors.

(f) A method of inhibiting herpesvirus replication in a subject in need thereof which comprises administering to the subject an effective amount of a Compound of Formula (I).

(g) A method of treating herpesvirus infection and/or reducing the likelihood or severity of symptoms of herpesvirus infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of anti-herpes agents and immunomodulators.

(i) The method of (h), wherein the anti-herpes agent is selected from the group consisting of herpesvirus polymerase inhibitors, and CMV terminase inhibitors.

(j) A method of inhibiting herpesvirus replication in a subject in need thereof which comprises administering to the subject the pharmaceutical composition of (a), (b) or (c) or the combination of (d) or (e).

(k) A method of treating herpesvirus infection and/or reducing the likelihood or severity of symptoms of herpesvirus infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine; (b) inhibiting herpesvirus replication or (c) treating herpesvirus infection and/or reducing the likelihood or severity of symptoms of herpesvirus infection. In these uses, the compounds of the present invention can optionally be employed in combination with one or more second therapeutic agents selected from anti-herpes agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (k) above are understood to include all embodiments of the compounds, including such embodiments as result from combinations of embodiments.

Non-limiting examples of the Compounds of Formula (I) include compounds 4-103, as set forth in the Examples below, and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below Alternative synthetic pathways and analogous structures will be apparent to those skilled in the art of organic synthesis.

One skilled in the art of organic synthesis will recognize that the synthesis of multicyclic heterocycle cores contained in Compounds of Formula (I) may require protection of certain functional groups (i.e., derivatization for the purpose of chemical compatibility with a particular reaction condition). Suitable protecting groups for the various functional groups of these Compounds and methods for their installation and removal are well known in the art of organic chemistry. A summary of many of these methods can be found in Greene et al., Protective Groups in Organic Synthesis, Wiley-Interscience, New York, (1999).

One skilled in the art of organic synthesis will also recognize that one route for the synthesis of the multicyclic heterocycle cores of the Compounds of Formula (I) may be more desirable depending on the choice of appendage substituents.

Additionally, one skilled in the art will recognize that in some cases the order of reactions may differ from that presented herein to avoid functional group incompatibilities and thus adjust the synthetic route accordingly.

The preparation of multicyclic intermediates useful for making the multicyclic heterocycle cores of the Compounds of Formula (I) have been described in the literature and in compendia such as "Comprehensive Heterocyclic Chemistry" editions I, II and III, published by Elsevier and edited by A. R. Katritzky & R. J K Taylor. Manipulation of the required substitution patterns have also been described in the available chemical literature as summarized in compendia such as "Comprehensive Organic Chemistry" published by Elsevier and edited by D H R. Barton and W. D. Ollis; "Comprehensive Organic Functional Group Transformations" edited by edited by A. R. Katritzky & R. J K Taylor and "Comprehensive Organic Transformation" published by Wiley-CVH and edited by R. C. Larock.

The starting materials used, and the intermediates prepared using the methods set forth in the Examples below may be isolated and purified if desired using conventional techniques, including but not limited to filtration, distillation, crystallization, chromatography and alike. Such materials can be characterized using conventional means, including physical constants and spectral data.

One skilled in the art will be aware of standard formulation techniques as set forth in the open literature as well as in textbooks such as Zheng, "Formulation and Analytical Development for Low-dose Oral Drug Products," Wiley, 2009, ISBN.

EXAMPLES

General Methods

Solvents, reagents, and intermediates that are commercially available were used as received. Reagents and intermediates that are not commercially available were prepared in the manner as described below. $^1$H NMR spectra are reported as ppm downfield from $Me_4Si$ with number of protons, multiplicities, and coupling constants in Hertz indicated parenthetically. Where LCMS data are presented, the observed parent ion is given. Flash column chromatography was performed using pre-packed normal phase silica or bulk silica, and using a gradient elution of hexanes/ethyl acetate, typically from 100% hexanes to 100% ethyl acetate.

Example 1

Preparation of Intermediate Compound Int-1

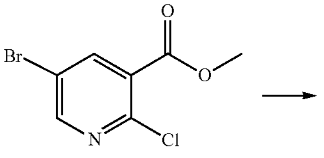

1a

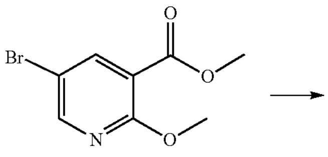

1b

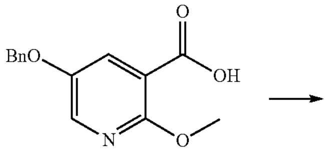

1c

-continued

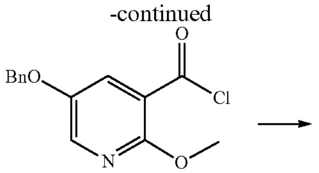

1d

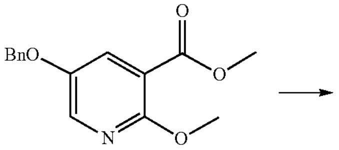

1e

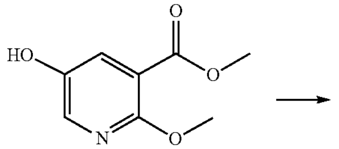

1f

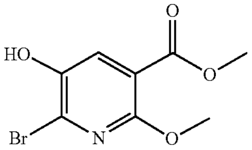

Int-1

Step A—Synthesis of Compound 1b

A 20-L, 3-necked round-bottom flask was charged with 1a (2.5 kg, 9.981 mmol), and MeOH (15 L), and the resulting solution was cooled to 0° C. Sodium methoxide in MeOH (5 N, 2.1 L) was added, and the resulting reaction was allowed to stir for 18 hours at 0° C. The reaction mixture was filtered, and the collected solids were dried in vacuo to provide compound 1b as a solid, which was used without further purification.

Step B—Synthesis of Compound 1c

A 50-L round-bottom flask (purged and maintained with an inert atmosphere of nitrogen) was charged with a mixture of compound 1b (2.2 kg, 8.9 mol) in toluene (32 L), phenyl methanol (4.8 kg, 44 mol), 1,10-phenanthroline (324 g, 1.80 mol), CuI (180 g, 0.945 mol), and $Cs_2CO_3$ (4.31 kg, 13.2 mol). The resulting reaction was heated to 110° C. and allowed to stir at this temperature for 18 hours. The reaction was then quenched with water (40 L), and the resulting solution was adjusted to pH 5 using HCl (1N). The acidified solution was extracted with ethyl acetate, and the organic extract was washed with water then brine, dried over $Na_2SO_4$, filtered, and concentrated in vacuo to provide 1c as a solid, which was used without further purification.

Step C—Synthesis of Compound 1d

A 20-L round-bottom flask, was charged with a mixture of 1c (2.2 kg, 8.5 mol) in $CH_2Cl_2$ (12 L), and the resulting solution was cooled to 0° C. Oxalyl chloride (3.2 kg, 2.5 mol) was added dropwise and the resulting reaction was allowed to stir for 4 hours at 0° C., then concentrated in vacuo to provide compound 1d as an oil, which was used without further purification.

Step D—Synthesis of Compound 1e

A 10-L round-bottom flask was charged with MeOH (8 L), and 1d (2.0 kg, 7.2 mol), and the resulting solution was allowed to stir for 2 hours at 20° C. The reaction mixture was then concentrated in vacuo, and the resulting residue was purified using silica gel chromatography, eluting with 10% EtOAc in hexanes, to provide compound 1e as an oil.

Step E—Synthesis of Compound 1f

A 3-L round-bottom flask was charged with a mixture of 1e (500 g, 1.83 mol) in MeOH (3 L). Palladium on carbon (10 wt %, 100 g) was added, and the resulting solution was allowed to stir for 5 hours at 25° C. The reaction mixture was filtered through a pad of Celite (diatomaceous earth) and the resulting filtrate was concentrated in vacuo. The resulting residue was recrystallized from PE/EA (1:1) to provide compound if as a solid.

Step F—Synthesis of Int-1

A 3-L round-bottom flask was charged with a mixture of if (185 g, 1.01 mol) in DMF (2 L), and the resulting solution was cooled to 0° C. N-bromosuccinimide (187 g, 1.05 mol) was added, and the resulting solution was stirred at 0° C. for 2 hours. The reaction mixture was diluted with water (10 L), and the resulting solution was filtered. The filtrate was concentrated in vacuo to provide Int-1 as a solid, which was used without further purification. MS: m/z 262.1/264.1=[M+H, $^{79}$Br and $^{81}$Br]. $^1$H NMR (400 MHz, DMSO-$d_6$, ppm) δ10.46 (s, 1H), 7.71 (s, 1H), 3.85 (s, 3H), 3.80 (s, 3H).

Example 2

Preparation of Intermediate Compound Int-2

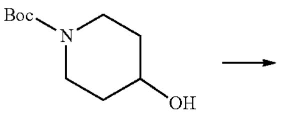

2a

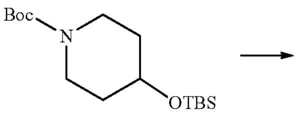

2b

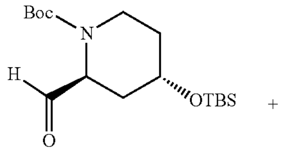

2c-1

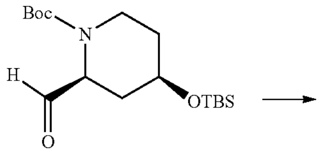

2c-2

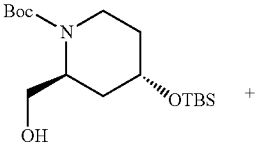

2d-1

-continued

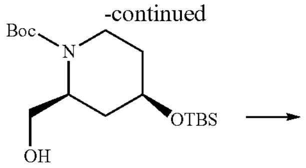

2d-2

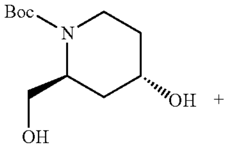

2e-1

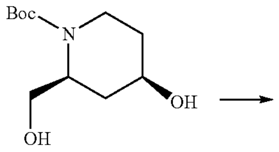

2e-2

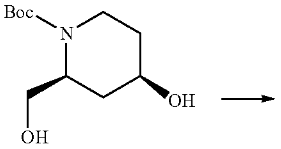

2f

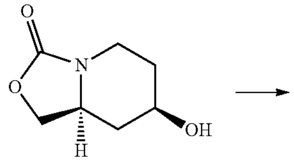

2g

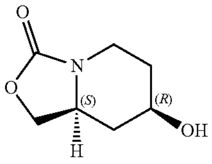

Int-2

Step A—Synthesis of Compound 2b

A 5-L, 3-necked round-bottom flask (purged and maintained with an inert atmosphere of nitrogen) was charged with 2a (120 g, 596 mmol), imidazole (81.2 g, 1.19 mmol), and $CH_2Cl_2$ (2.5 L). To the resulting solution was added tert-butyldimethylsilyl chloride (116.7 g, 774.3 mmol) in portions, and the resulting reaction was allowed to stir for 3 hours at room temperature, then was cooled to 10° C. The reaction was then quenched by the addition of saturated, aqueous $NaHCO_3$ (3 L), and the resulting solution was extracted with $CH_2Cl_2$. The organic extract was dried over $Na_2SO_4$, filtered, and concentrated in vacuo. The resulting residue was purified using silica gel chromatography, eluting with 10% EtOAc in petroleum ether, to provide compound 2b as an oil.

Step B—Synthesis of Compounds 2c-1 and 2c-2

A 10-L, 4-necked round-bottom flask (purged and maintained with an inert atmosphere of nitrogen) was charged 2b (170 g, 539 mmol), and TMEDA (138 g, 1188 mmol) in methyl tert-butyl ether (4.2 L). The resulting solution was cooled to −78° C., and sec-BuLi (1.3M in cyclohexane, 748 mL, 970 mmol) was added dropwise with stirring. The resulting solution was allowed to stir for 1 hour at −40° C. in a liquid nitrogen bath. After cooling to −78° C., DMF (395 g, 1872 mmol) was added dropwise with stirring. The resulting reaction was allowed to stir at −40° C. for 1.5 hours, then quenched by the addition of saturated, aqueous $NH_4Cl$ (2 L). The resulting solution was extracted with methyl tert-butyl ether, dried over $Na_2SO_4$, and concentrated in vacuo to provide 2c-1 and 2c-2 as an oil which was used without further purification.

Step C—Synthesis of Compounds 2d-1 and 2d-2

A 5-L, 4-necked round-bottom flask (purged and maintained with an inert atmosphere of nitrogen) was charged with 2c-1 and 2c-2 (100 g, 291 mmol) in methanol (2 L). Sodium borohydride (22 g, 582 mmol) was added in portions at 0° C., and the resulting solution was allowed to stir for 2 hours at 0° C. The reaction was quenched by the addition of water (5 L), and the resulting solution was extracted with ethyl acetate, dried over $Na_2SO_4$, and concentrated in vacuo to provide 2d-1 and 2d-2 as an oil, which was used without further purification.

Step D—Synthesis of Compounds 2e-1 and 2e-2

A 5-L, 3-necked round-bottom flask (purged and maintained with an inert atmosphere of nitrogen) was charged with 2d-1 and 2d-2 (100 g, 289 mmol), and THF (2 L), and the solution was added tetra-n-butylammonium fluoride (1 M in THF, 268 mL). The resulting solution was allowed to stir for 3 hours at room temperature. The resulting mixture was concentrated in vacuo to provide a mixture of compounds 2e-1 and 2e-2, which were separated in the following step.

Step E—Resolution of Compound 2f

A mixture of 2e-1 and 2e-2 was purified using silica gel chromatography, eluting with 90% EtOAc in petroleum ether, to provide compound 2f as an oil.

Step F—Synthesis of Compound 2g

A 3-L, 3-necked round-bottom flask (purged and maintained with an inert atmosphere of nitrogen) was charged with 2f (100 g, 432 mmol), and potassium 2-methylpropan-2-olate (29.1 g, 260 mol) in isopropanol (2 L). The resulting solution was allowed to stir for 3 hours at 70° C., then cooled to 0° C. with an ice/salt bath. HCl in MeOH (4 N) was used to adjust the pH to 6 and the resulting mixture was concentrated in vacuo. The resulting residue was diluted with $CH_2Cl_2$ (1 L), filtered, and concentrated in vacuo, and the residue obtained was purified using silica gel chromatography, eluting with 90% EtOAc in petroleum ether, to provide compound 2g as a solid.

Step G—Chiral Resolution of Int-2

Compound 2g was resolved using prep-SFC (Chiral Pak IG 5×25 cm, 5 um S90IG0SCY-VK00187455 mobile phase, 70% $CO_2$ in MeOH, 30 min, 42 bar, 160 mL/min) to provide Int-2 as a solid. MS: m/z 158=[M+H]. $^1$H NMR (400 MHz, $CDCl_3$, ppm) δ4.47 (t, 1H), 4.00-3.89 (m, 2H), 3.83-3.72 (m, 2H), 2.97-2.85 (m, 1H), 2.17-2.10 (m, 1H), 2.02-1.95 (m, 1H), 1.51-1.31 (m, 2H).

Example 3

Preparation of Intermediate Compound Int-3

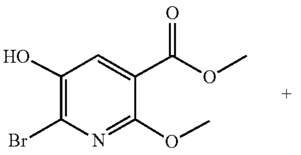

Int-1

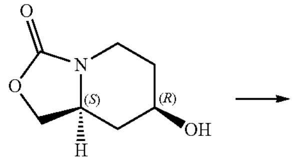

Int-2

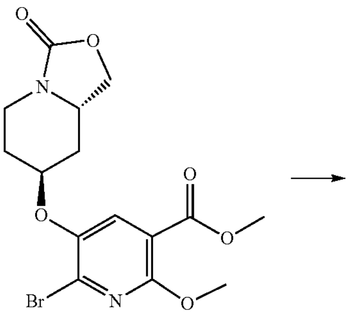

3a

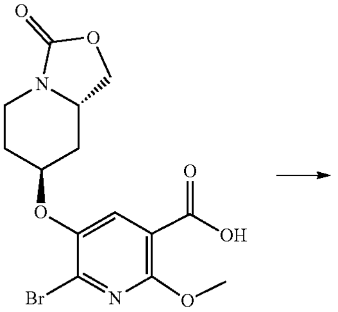

3b

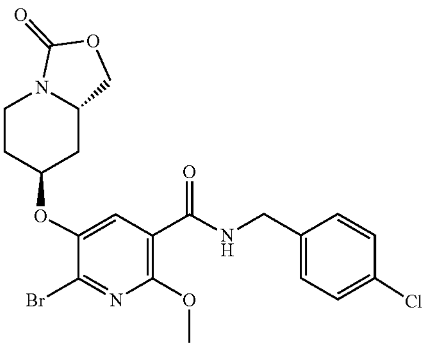

Int-3

Step A—Synthesis of Compound 3a

To a mixture of Int-1 (4.50 g, 17.2 mmol), and Int-2 (3.51 g, 22.3 mmol) in THF (114 mL) was added triphenylphosphine (6.31 g, 24.0 mmol), and DBAD (5.54 g, 24.0 mmol), and the resulting reaction was allowed to stir at room temperature for about 15 hours. Additional Int-1 (0.68 g), triphenylphosphine (0.90 g), and DBAD (0.83 g) were added, and the reaction was stirred another 48 hours, then diluted with water, and extracted with ethyl acetate. The organics were washed with brine, dried over $MgSO_4$, filtered, and concentrated in vacuo, and the residue obtained was purified using silica gel chromatography, eluting with 0-95% EtOAc in hexanes, to provide compound 3a as a solid. MS: m/z 401.3 and 403.3=[M+H, $^{79}Br$ and $^{81}Br$].

Step B—Synthesis of Compound 3b

To a mixture of 3a (8.63 g, 21.5 mmol) in dioxane (111 mL) was added sodium hydroxide (1 M, 22.2 mL), and water (32.7 mL). After being allowed to stir for 3 hours at room temperature, the reaction was concentrated in vacuo. The resulting residue was added HCl (1 M, 22.2 mL). After being allowed to stir for 1 hour, the resulting m was filtered and the filter cake was washed with water, and then dried, to provide 3b as a solid which was used without further purification. MS: m/z 387.3 and 389.3=[M+H, $^{79}Br$ and $^{81}Br$].

Step C—Synthesis of Int-3

To a mixture of 3b (8.06 g, 20.8 mmol) in $CH_2Cl_2$ (208 mL), and $Et_3N$ (7.25 ml, 52.0 mmol) was added (4-chlorophenyl)methanamine (3.04 ml, 25.0 mmol), and then dropwise 2,4,6-tripropyl-1,3,5,2,4,6-trioxatriphosphinane 2,4,6-trioxide (50 wt % in EtOAc, 15.5 mL, 26.0 mmol). The resulting reaction was allowed to stir at room temperature for 2.5 hours, then the reaction mixture was concentrated in vacuo, and the residue obtained was purified using silica gel chromatography, eluting with 0-50% (3:1 EtOAc:EtOH) in hexanes, to provide Int-3 as a solid. MS: m/z 510.4 and 512.4=[M+H, $^{79}Br$ and $^{81}Br$]. $^1H$ NMR (500 MHz, $CDCl_3$, ppm) δ8.23 (t, J=5.5 Hz, 1H), 8.12 (s, 1H), 7.34 (d, J=8.5 Hz, 2H), 7.29 (d, J=8.5 Hz, 2H), 4.89 (s, 1H), 4.63 (d, J=5.5 Hz, 2H), 4.46 (t, J=8.5 Hz, 1H), 4.22-4.28 (m, 1H), 4.08 (s, 3H), 3.93 (dd, J=8.5, 5.5 Hz, 1H), 3.81 (dd, J=13.5, 5.0 Hz, 1H), 2.20 (dd, J=14.0, 2.0 Hz, 1H), 2.02 (dd, J=22.0, 1.5 Hz, 1H), 1.74-1.81 (m, 1H), 1.69 (dt, J=12.0, 2.0 Hz, 1H).

Example 4

Preparation of Compound 4

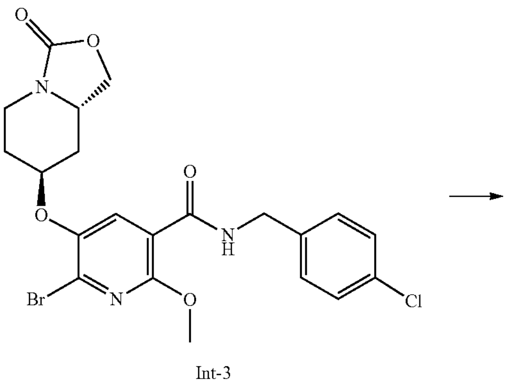

Int-3

-continued

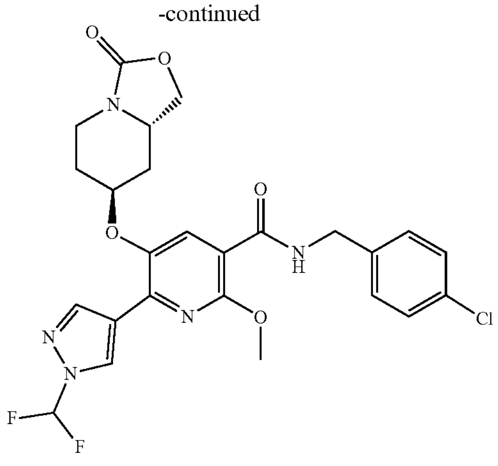

4

Step A—Synthesis of Compound 4

A solution of Int-3 (2.30 g, 4.50 mmol), 1-(difluoromethyl)-4-(4,4,5,5-tetramethyl-1,3,2-dioxaborolan-2-yl)-1H-pyrazole (1.099 g, 4.50 mmol), and aqueous potassium phosphate (1 M, 13.5 mL) in dioxane (24 mL) was purged subsurface with nitrogen. 1,1'-Bis(di-tert-butylphosphino)ferrocene palladium dichloride (0.147 g, 0.225 mmol) was added, and the reaction was purged further, then sealed and irradiated at 100° C. for 20 minutes. The reaction was diluted with ethyl acetate and the organic phase was washed with water. The aqueous wash was back-extracted with ethyl acetate, and then the combined organics were washed with brine, dried over $MgSO_4$, filtered, and concentrated in vacuo. The resulting residue was purified using preparative HPLC (reverse-phase C-18), eluting with acetonitrile/water+0.1% TFA 10-80% to provide compound 4 as a foam. MS: m/z 548.4=[M+H]. $^1H$ NMR (500 MHz, $CDCl_3$, ppm) δ8.49 (s, 1H), 8.39 (t, J=5.5 Hz, 1H), 8.35 (s, 1H), 8.23 (s, 1H), 7.35 (d, J=8.5 Hz, 2H), 7.31 (d, J=8.5 Hz, 2H), 7.28 (t, J=60.5 Hz, 1H), 5.04 (s, 1H), 4.65 (d, J=5.5 Hz, 2H), 4.44 (t, J=8.0 Hz, 1H), 4.13 (s, 3H), 3.98-4.05 (m, 1H), 3.93 (dd, J=8.0, 5.5 Hz, 1H), 3.89 (dd, J=13.5, 5.0 Hz, 1H), 3.24 (dt, J=13.5, 3.5 Hz, 1H), 2.30 (dd, J=14.0, 2.0 Hz, 1H), 2.14 (d, J=14.5 Hz, 1H), 1.88-1.92 (m 1H), 1.72-1.78 (m, 1H).

Example 5

Preparation of Compound 5

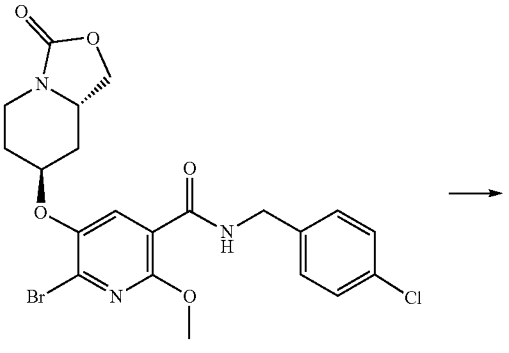

Int-3

-continued

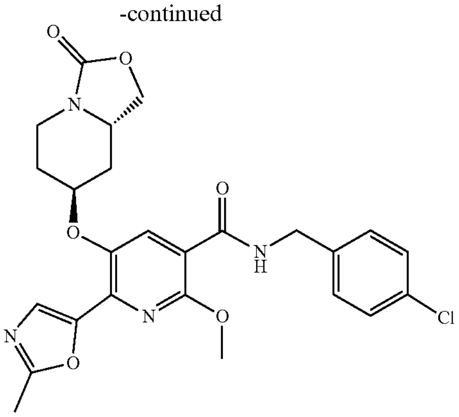

5

Step A—Synthesis of Compound 5

A solution of Int-3 (350 mg, 0.685 mmol), 2-methyl-5-(4,4,5,5-tetramethyl-1,3,2-dioxaborolan-2-yl)oxazole (150 mg, 0.720 mmol), and aqueous potassium phosphate (1 M, 2.06 mL) in dioxane (4.6 mL) was purged subsurface with nitrogen. 1,1'-Bis(di-tert-butylphosphino)ferrocene palladium dichloride (22 mg, 0.034 mmol) was added, and the reaction was purged further, then sealed and irradiated at 130° C. for 30 minutes. The reaction was diluted with ethyl acetate and the organic phase was washed with water. The aqueous wash was back-extracted with ethyl acetate, and then the combined organics were washed with brine, dried over $MgSO_4$, filtered, and concentrated in vacuo. The resulting residue was purified using silica gel chromatography, eluting with 0-80% (3:1 EtOAc:EtOH) in hexanes, and then using preparative HPLC (reverse-phase C-18), eluting with acetonitrile/water+0.1% TFA 10-65% to provide compound 5 as a foam. MS: m/z 513.5=[M+H]. $^1$H NMR (500 MHz, $CDCl_3$, ppm) δ8.39 (t, J=6.0 Hz, 1H), 8.23 (s, 1H), 7.66 (s, 1H), 7.34 (d, J=6.5 Hz, 2H), 7.31 (d, J=6.5 Hz, 2H), 5.04 (s, 1H), 4.65 (d, J=5.5 Hz, 2H), 4.44 (t, J=8.5 Hz, 1H), 4.14 (s, 3H), 4.08-4.12 (m, 1H), 3.93 (dd, J=8.5, 5.5 Hz, 1H), 3.85 (dd, J=13.5, 5.0 Hz, 1H), 3.30 (dt, J=13.5, 3.5 Hz, 1H), 2.61 (s, 3H), 2.30 (dd, J=14.0, 2.0 Hz, 1H), 2.10 (dd, J=13.0, 1.5 Hz, 1H), 1.82-1.90 (m 1H), 1.72-1.78 (m, 1H).

Example 6

Preparation of Compound 6

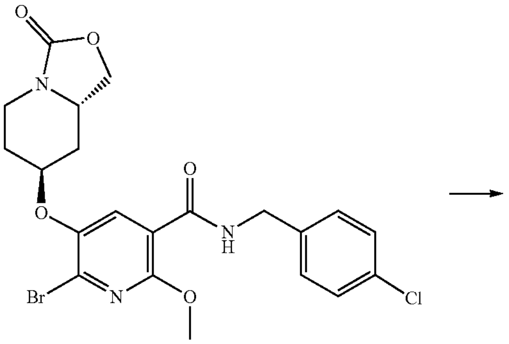

Int-3

-continued

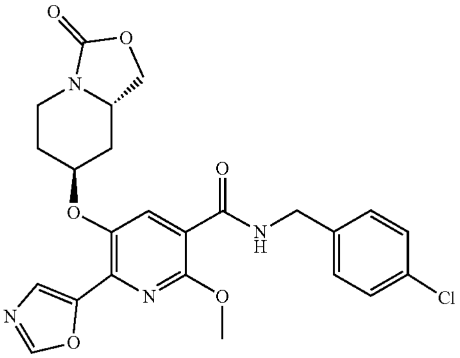

6

Step A—Synthesis of Compound 6

A solution of Int-3 (800 mg, 1.57 mmol), 5-(4,4,5,5-tetramethyl-1,3,2-dioxaborolan-2-yl)oxazole (336 mg, 1.72 mmol), and aqueous potassium phosphate (1 M, 4.70 mL) in dioxane (9.8 mL) was purged subsurface with nitrogen. 1,1'-Bis(di-tert-butylphosphino)ferrocene palladium dichloride (51 mg, 0.078 mmol) was added, and the reaction was purged further, then sealed and irradiated at 130° C. for 30 minutes. The reaction was diluted with ethyl acetate and washed with water; the aqueous phase was back-extracted with ethyl acetate, and then the combined organics were washed with brine, dried over $MgSO_4$, and concentrated in vacuo. The resulting residue was purified using preparative HPLC (reverse-phase C-18), eluting with acetonitrile/water+0.1% TFA 10-70% to provide compound 6 as a foam. MS: m/z 499.4=[M+H]. $^1$H NMR (500 MHz, $CDCl_3$, ppm) δ8.40 (t, J=6.0 Hz, 1H), 8.27 (s, 1H), 8.08 (s, 1H), 7.81 (s, 1H), 7.34 (d, J=8.5 Hz, 2H), 7.31 (d, J=8.5 Hz, 2H), 5.07 (s, 1H), 4.65 (d, J=5.5 Hz, 2H), 4.45 (t, J=8.5 Hz, 1H), 4.15 (s, 3H), 4.08-4.14 (m, 1H), 3.94 (dd, J=8.0, 5.5 Hz, 1H), 3.86 (dd, J=13.0, 5.0 Hz, 1H), 3.30 (dt, J=13.5, 3.0 Hz, 1H), 2.29 (d, J=13.5 Hz, 1H), 2.10 (d, J=14.0 Hz, 1H), 1.85-1.91 (m 1H), 1.74-1.80 (m, 1H).

Example 7

Preparation of Compound 6

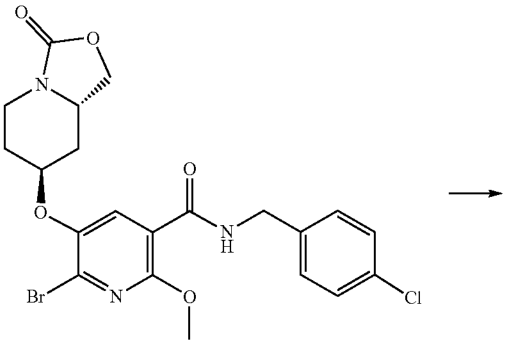

Int-3

-continued

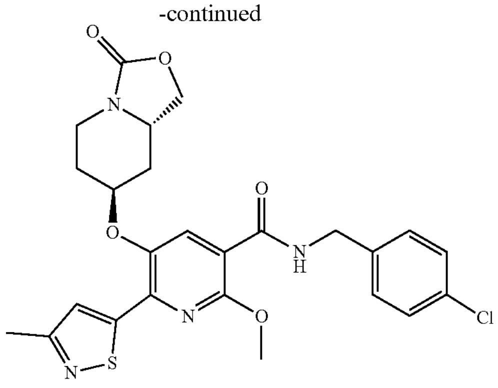

7

Step A—Synthesis of Compound 7

A solution of Int-3 (45 mg, 0.088 mmol), 3-methyl-5-(tetramethyl-1,3,2-dioxaborolan-2-yl)-1,2-thiazole (22 mg, 0.097 mmol), and aqueous potassium phosphate (1 M, 0.26 mL) in dioxane (0.63 mL) was purged subsurface with nitrogen. 1,1'-Bis(di-tert-butylphosphino)ferrocene palladium dichloride (3 mg, 0.004 mmol) was added, and the reaction was purged further, then sealed and irradiated at 130° C. for 30 minutes. The reaction was diluted with ethyl acetate and the organic phase was washed with water. The aqueous wash was back-extracted with ethyl acetate, and then the combined organics were washed with brine, dried over $MgSO_4$, filtered, and concentrated in vacuo. The resulting residue was purified using preparative HPLC (reverse-phase C-18), eluting with acetonitrile/water+0.1% TFA 10-80% to provide compound 7 as a foam. MS: m/z 529.4=[M+H]. $^1$H NMR (500 MHz, $CDCl_3$, ppm) δ8.39 (t, J=5.5 Hz, 1H), 8.29 (s, 1H), 7.83 (s, 1H), 7.35 (d, J=9.0 Hz, 2H), 7.31 (d, J=8.5 Hz, 2H), 5.13 (s, 1H), 4.66 (d, J=5.5 Hz, 2H), 4.47 (t, J=8.5 Hz, 1H), 4.27-4.33 (m, 1H), 4.15 (s, 3H), 3.95 (dd, J=8.5, 5.0 Hz, 1H), 3.89 (dd, J=13.0, 5.0 Hz, 1H), 3.45 (dt, J=13.0, 3.0 Hz, 1H), 2.59 (s, 3H), 2.31 (dd, J=14.0, 3.0 Hz, 1H), 2.15 (dd, J=14.5, 2.5 Hz, 1H), 1.88-1.95 (m 1H), 1.77-1.81 (m, 1H).

The following compounds of the present invention were made using the method described in Example 4 above, and substituting the appropriate reactants and/or reagents:

| Compound | Structure | MS [M + H] |
| --- | --- | --- |
| 8 | 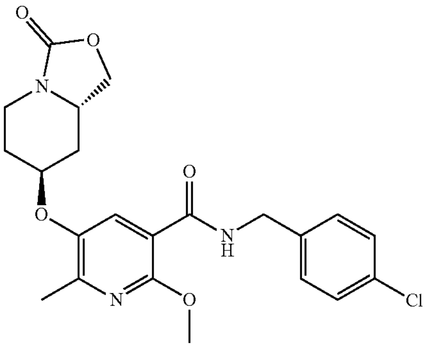 [SMILES: COc1nc(C)c(O[C@H]2CCN3C(=O)OC[C@@H]3C2)cc1C(=O)NCc1ccc(Cl)cc1] | 446.3 |
| 9 | 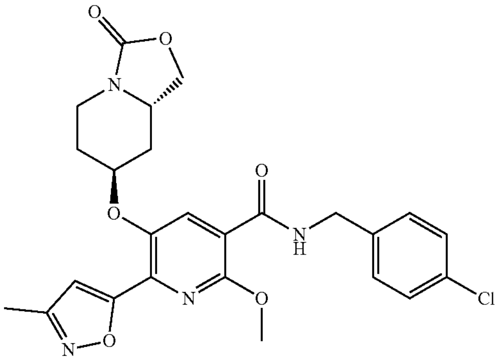 [SMILES: COc1nc(-c2cc(C)no2)c(O[C@H]2CCN3C(=O)OC[C@@H]3C2)cc1C(=O)NCc1ccc(Cl)cc1] | 513.4 |

-continued
| Compound | Structure | MS [M + H] |
|---|---|---|
| 10 | 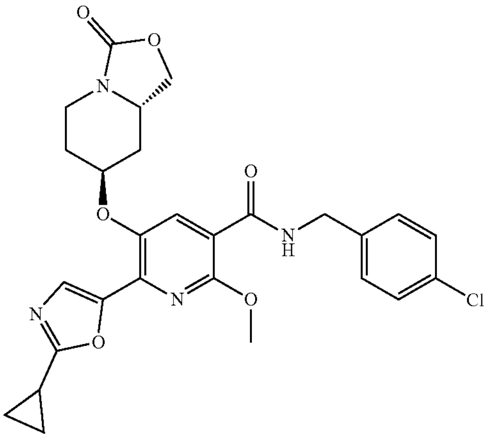 [SMILES: COc1nc(-c2cnc(C3CC3)o2)c(O[C@H]2CCN3C(=O)OC[C@@H]3C2)cc1C(=O)NCc1ccc(Cl)cc1] | 539.5 |
| 11 | 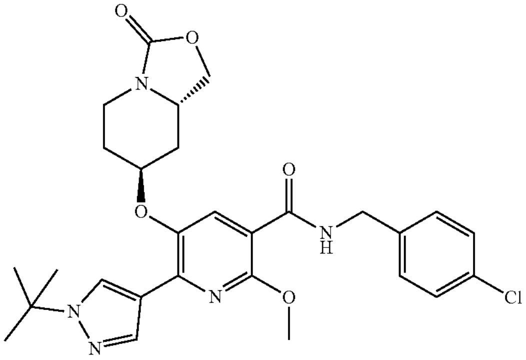 [SMILES: COc1nc(-c2cnn(C(C)(C)C)c2)c(O[C@H]2CCN3C(=O)OC[C@@H]3C2)cc1C(=O)NCc1ccc(Cl)cc1] | 554.4 |
| 12 | 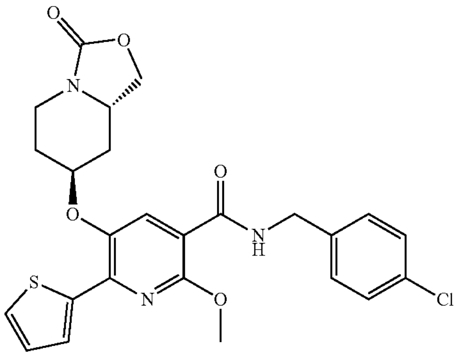 [SMILES: COc1nc(-c2cccs2)c(O[C@H]2CCN3C(=O)OC[C@@H]3C2)cc1C(=O)NCc1ccc(Cl)cc1] | 514.3 |
| 13 | 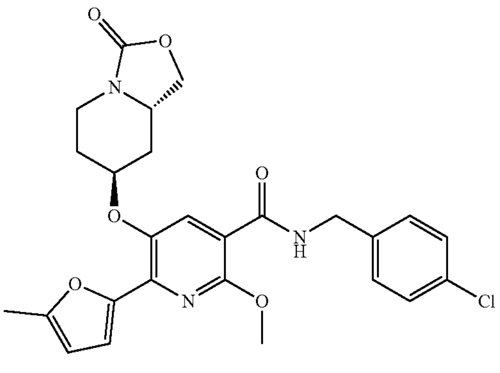 [SMILES: COc1nc(-c2ccc(C)o2)c(O[C@H]2CCN3C(=O)OC[C@@H]3C2)cc1C(=O)NCc1ccc(Cl)cc1] | 512.3 |

-continued
| Compound | Structure | MS [M + H] |
|---|---|---|
| 14 | 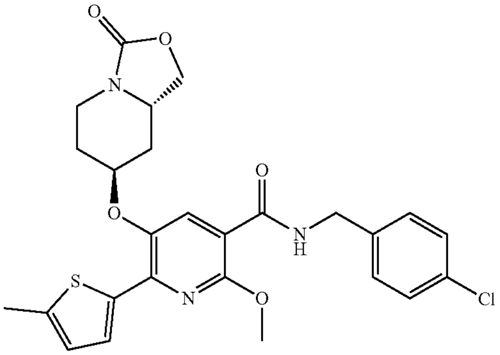 [SMILES: COc1nc(-c2ccc(C)s2)c(O[C@H]2CCN3C(=O)OC[C@@H]3C2)cc1C(=O)NCc1ccc(Cl)cc1] | 528.3 |
| 15 | 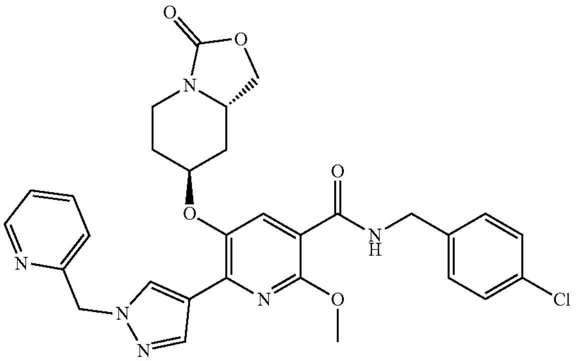 [SMILES: COc1nc(-c2cnn(Cc3ccccn3)c2)c(O[C@H]2CCN3C(=O)OC[C@@H]3C2)cc1C(=O)NCc1ccc(Cl)cc1] | 589.4 |
| 16 | 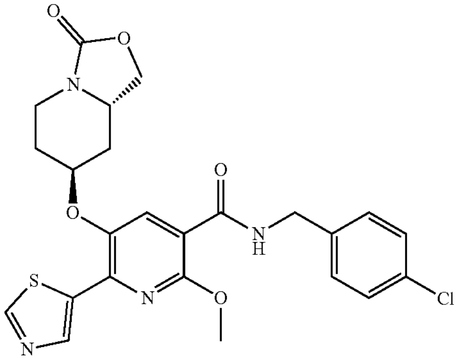 [SMILES: COc1nc(-c2cncs2)c(O[C@H]2CCN3C(=O)OC[C@@H]3C2)cc1C(=O)NCc1ccc(Cl)cc1] | 515.3 |
| 17 | 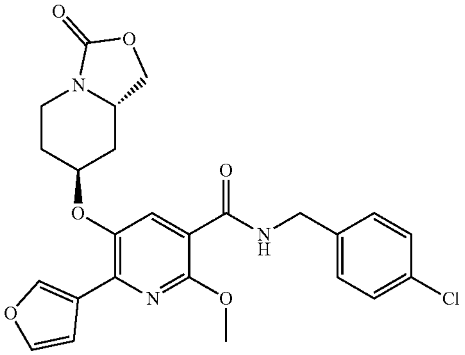 [SMILES: COc1nc(-c2ccoc2)c(O[C@H]2CCN3C(=O)OC[C@@H]3C2)cc1C(=O)NCc1ccc(Cl)cc1] | 498.3 |

-continued
| Compound | Structure | MS [M + H] |
|---|---|---|
| 18 | 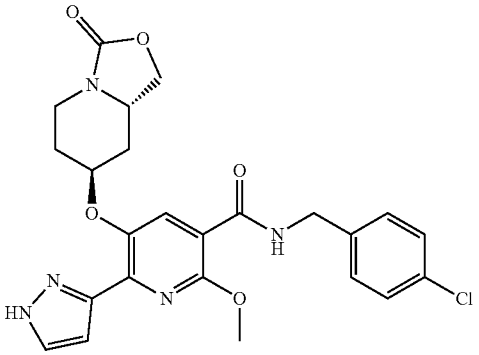 [SMILES: COc1nc(-c2cc[nH]n2)c(O[C@H]2CCN3C(=O)OC[C@@H]3C2)cc1C(=O)NCc1ccc(Cl)cc1] | 498.3 |
| 19 | 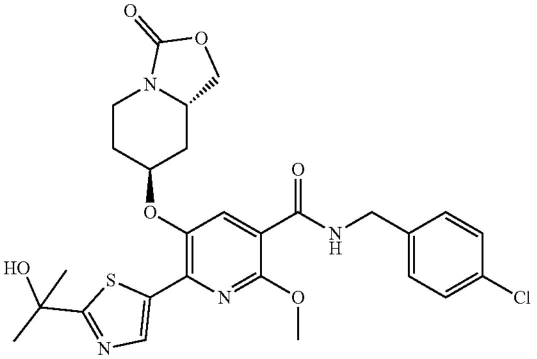 [SMILES: COc1nc(-c2cnc(C(C)(C)O)s2)c(O[C@H]2CCN3C(=O)OC[C@@H]3C2)cc1C(=O)NCc1ccc(Cl)cc1] | 573.3 |
| 20 | 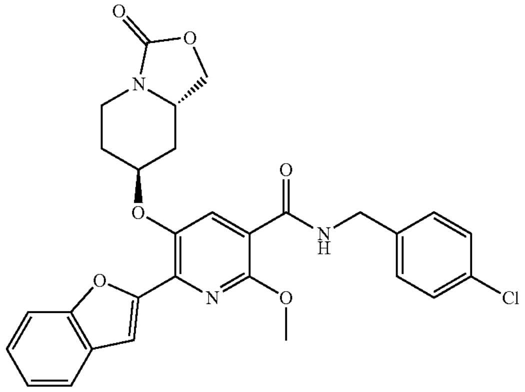 [SMILES: COc1nc(-c2cc3ccccc3o2)c(O[C@H]2CCN3C(=O)OC[C@@H]3C2)cc1C(=O)NCc1ccc(Cl)cc1] | 548.3 |
| 21 | 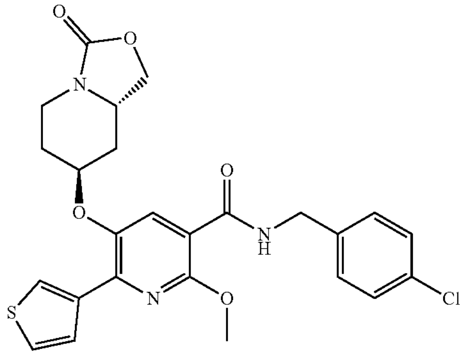 [SMILES: COc1nc(-c2ccsc2)c(O[C@H]2CCN3C(=O)OC[C@@H]3C2)cc1C(=O)NCc1ccc(Cl)cc1] | 514.2 |

-continued
| Compound | Structure | MS [M + H] |
| --- | --- | --- |
| 22 | 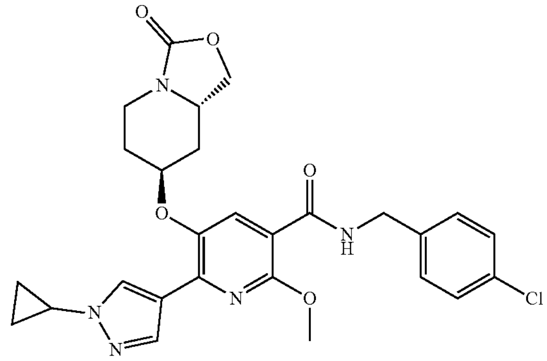 [SMILES: COc1nc(-c2cnn(C3CC3)c2)c(O[C@H]2CCN3C(=O)OC[C@@H]3C2)cc1C(=O)NCc1ccc(Cl)cc1] | 538.3 |
| 23 | 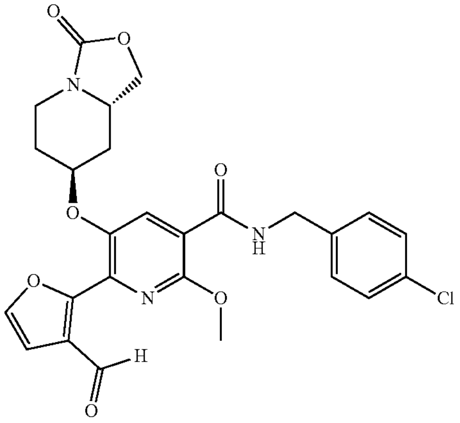 [SMILES: COc1nc(-c2occc2C=O)c(O[C@H]2CCN3C(=O)OC[C@@H]3C2)cc1C(=O)NCc1ccc(Cl)cc1] | 526.3 |
| 24 | 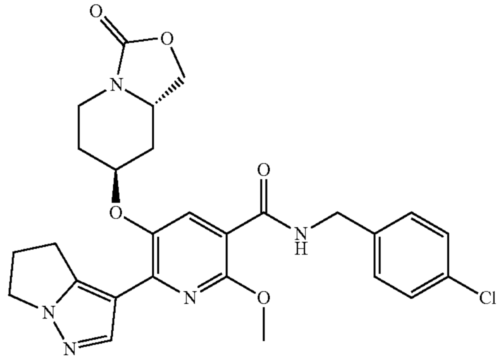 [SMILES: COc1nc(-c2cnn3c2CCC3)c(O[C@H]2CCN3C(=O)OC[C@@H]3C2)cc1C(=O)NCc1ccc(Cl)cc1] | 538.3 |
| 25 | 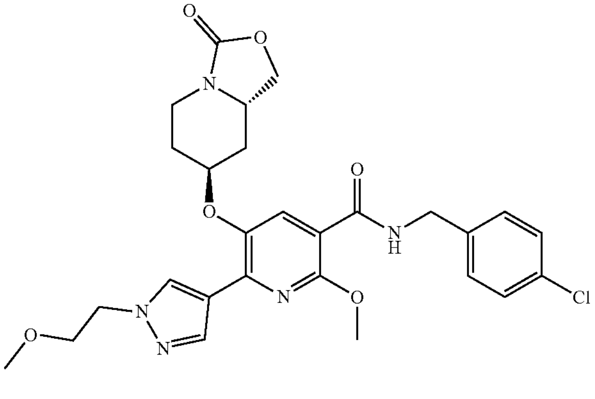 [SMILES: COCCn1cc(-c2nc(OC)c(C(=O)NCc3ccc(Cl)cc3)cc2O[C@H]2CCN3C(=O)OC[C@@H]3C2)cn1] | 556.4 |

-continued
| Compound | Structure | MS [M + H] |
|---|---|---|
| 26 | 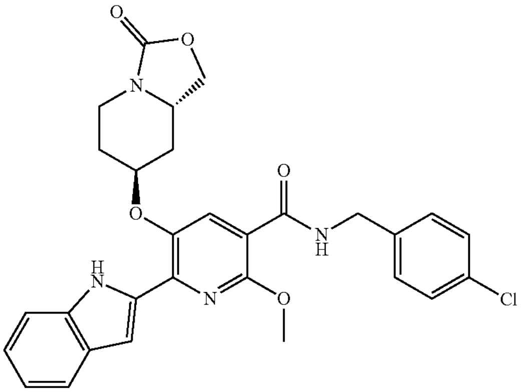 [SMILES: COc1nc(-c2cc3ccccc3[nH]2)c(O[C@H]2CCN3C(=O)OC[C@@H]3C2)cc1C(=O)NCc1ccc(Cl)cc1] | 547.4 |
| 27 | 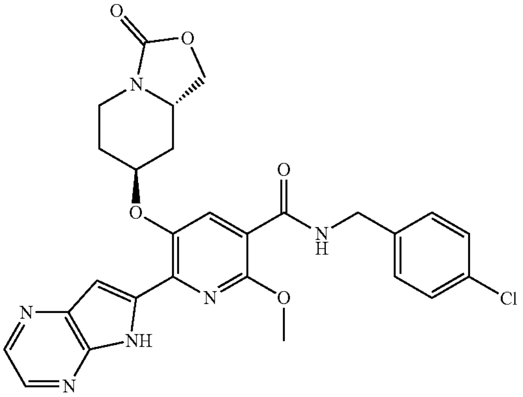 [SMILES: COc1nc(-c2cc3nccnc3[nH]2)c(O[C@H]2CCN3C(=O)OC[C@@H]3C2)cc1C(=O)NCc1ccc(Cl)cc1] | 549.3 |
| 28 | 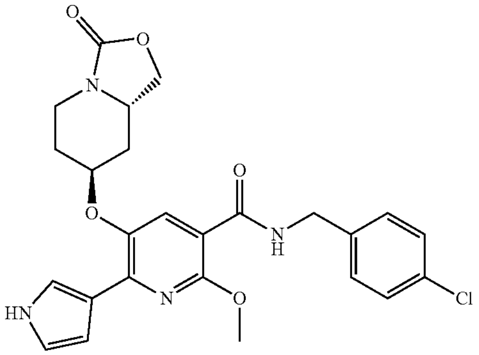 [SMILES: COc1nc(-c2cc[nH]c2)c(O[C@H]2CCN3C(=O)OC[C@@H]3C2)cc1C(=O)NCc1ccc(Cl)cc1] | 497.3 |
| 29 | 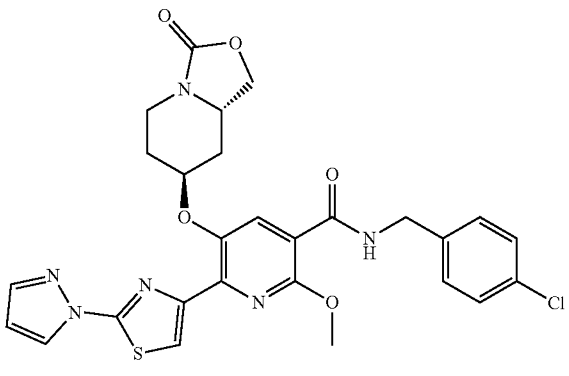 [SMILES: COc1nc(-c2csc(-n3cccn3)n2)c(O[C@H]2CCN3C(=O)OC[C@@H]3C2)cc1C(=O)NCc1ccc(Cl)cc1] | 581.3 |

-continued
| Compound | Structure | MS [M + H] |
|---|---|---|
| 30 | 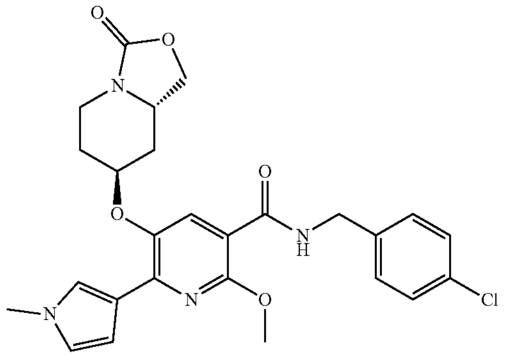 [SMILES: COc1nc(-c2ccn(C)c2)c(O[C@H]2CCN3C(=O)OC[C@@H]3C2)cc1C(=O)NCc1ccc(Cl)cc1] | 511.3 |
| 31 | 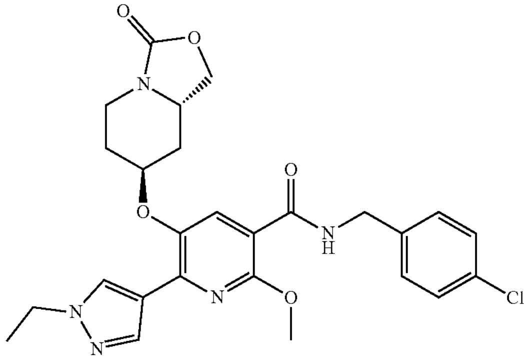 [SMILES: CCn1cc(-c2nc(OC)c(C(=O)NCc3ccc(Cl)cc3)cc2O[C@H]2CCN3C(=O)OC[C@@H]3C2)cn1] | 526.3 |
| 32 | 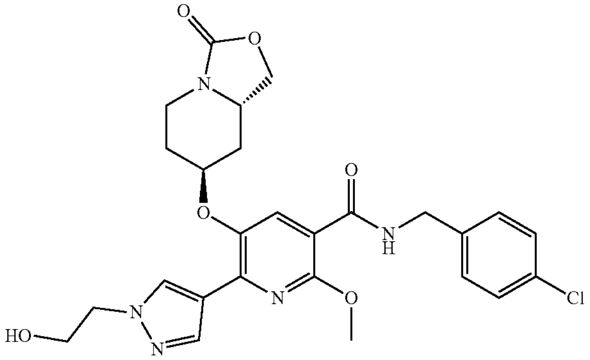 [SMILES: COc1nc(-c2cnn(CCO)c2)c(O[C@H]2CCN3C(=O)OC[C@@H]3C2)cc1C(=O)NCc1ccc(Cl)cc1] | 542.3 |
| 33 | 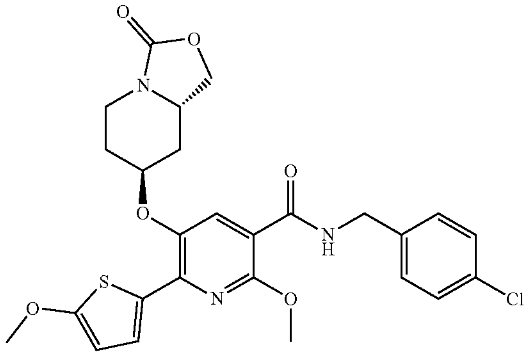 [SMILES: COc1ccc(-c2nc(OC)c(C(=O)NCc3ccc(Cl)cc3)cc2O[C@H]2CCN3C(=O)OC[C@@H]3C2)s1] | 544.3 |

-continued
| Compound | Structure | MS [M + H] |
|---|---|---|
| 34 | 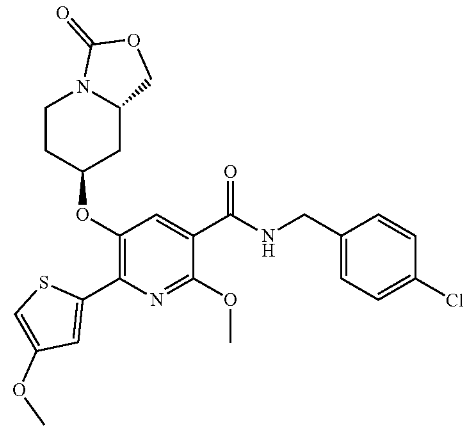 [SMILES: COc1csc(-c2nc(OC)c(C(=O)NCc3ccc(Cl)cc3)cc2O[C@H]2CCN3C(=O)OC[C@@H]3C2)c1] | 544.3 |
| 35 | 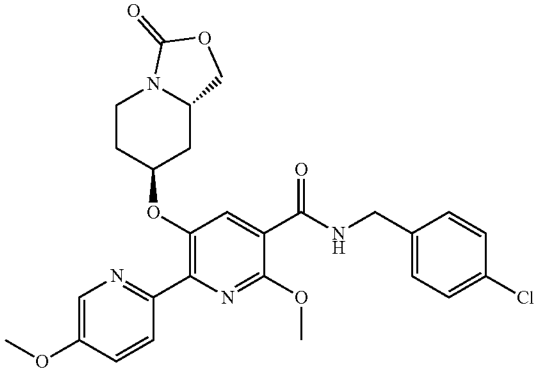 [SMILES: COc1ccc(-c2nc(OC)c(C(=O)NCc3ccc(Cl)cc3)cc2O[C@H]2CCN3C(=O)OC[C@@H]3C2)nc1] | 539.3 |
| 36 | 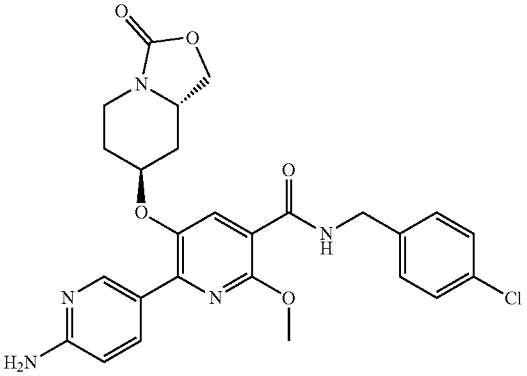 [SMILES: COc1nc(-c2ccc(N)nc2)c(O[C@H]2CCN3C(=O)OC[C@@H]3C2)cc1C(=O)NCc1ccc(Cl)cc1] | 524.3 |
| 37 | 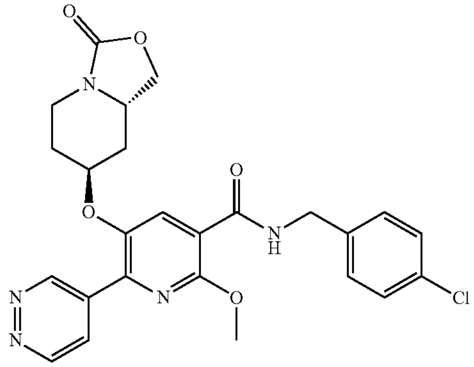 [SMILES: COc1nc(-c2ccnnc2)c(O[C@H]2CCN3C(=O)OC[C@@H]3C2)cc1C(=O)NCc1ccc(Cl)cc1] | 510.3 |

-continued
| Compound | Structure | MS [M + H] |
| --- | --- | --- |
| 38 | 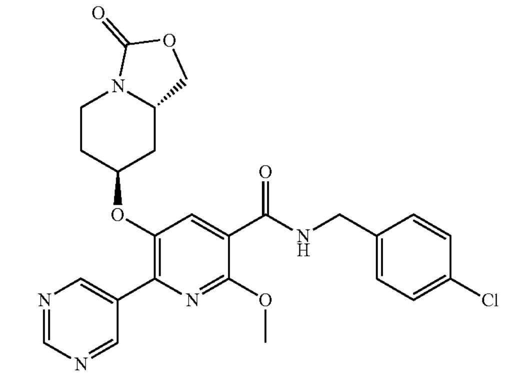 [SMILES: COc1nc(-c2cncnc2)c(O[C@H]2CCN3C(=O)OC[C@@H]3C2)cc1C(=O)NCc1ccc(Cl)cc1] | 510.3 |
| 39 | 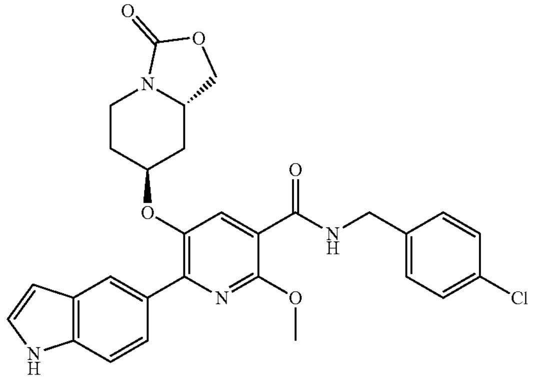 [SMILES: COc1nc(-c2ccc3[nH]ccc3c2)c(O[C@H]2CCN3C(=O)OC[C@@H]3C2)cc1C(=O)NCc1ccc(Cl)cc1] | 547.3 |
| 40 | 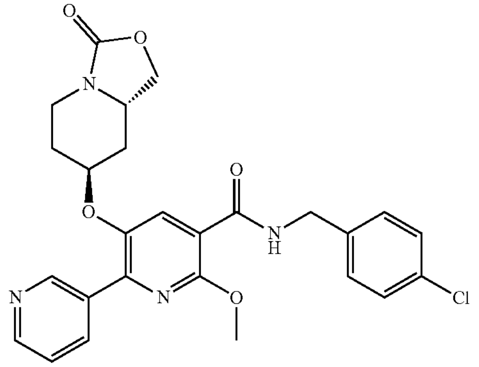 [SMILES: COc1nc(-c2cccnc2)c(O[C@H]2CCN3C(=O)OC[C@@H]3C2)cc1C(=O)NCc1ccc(Cl)cc1] | 509.3 |
| 41 | 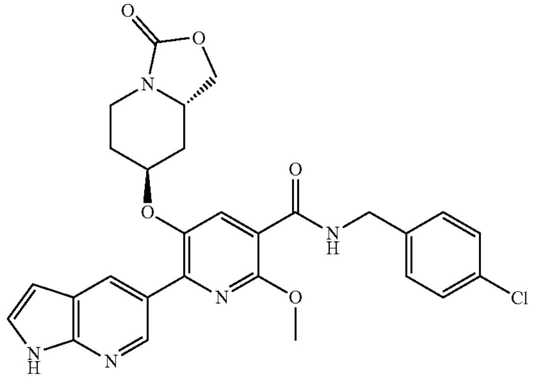 [SMILES: COc1nc(-c2cnc3[nH]ccc3c2)c(O[C@H]2CCN3C(=O)OC[C@@H]3C2)cc1C(=O)NCc1ccc(Cl)cc1] | 548.3 |

-continued
| Compound | Structure | MS [M + H] |
| --- | --- | --- |
| 42 | 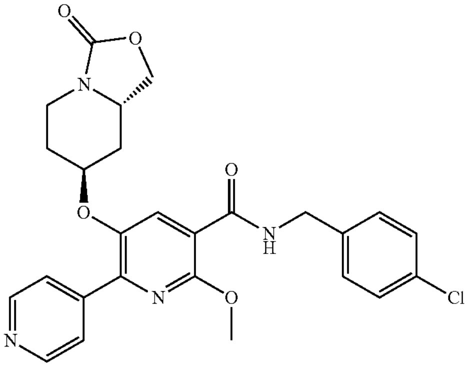 | 509.3 |
| 43 | 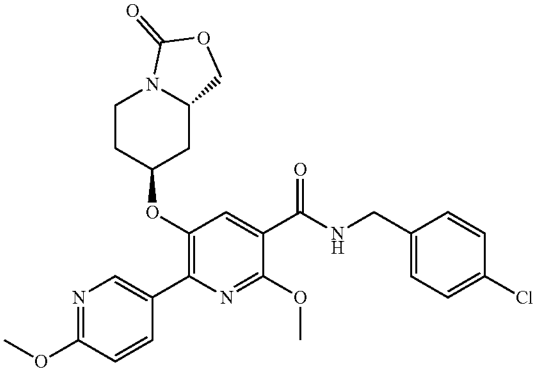 [SMILES: COc1ccc(-c2nc(OC)c(C(=O)NCc3ccc(Cl)cc3)cc2O[C@H]2CCN3C(=O)OC[C@@H]3C2)cn1] | 539.3 |
| 44 | 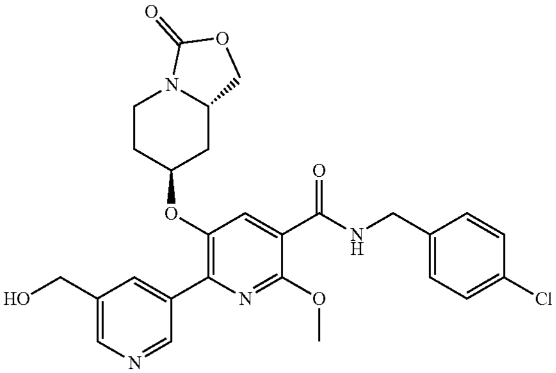 [SMILES: COc1nc(-c2cncc(CO)c2)c(O[C@H]2CCN3C(=O)OC[C@@H]3C2)cc1C(=O)NCc1ccc(Cl)cc1] | 539.3 |
| 45 | 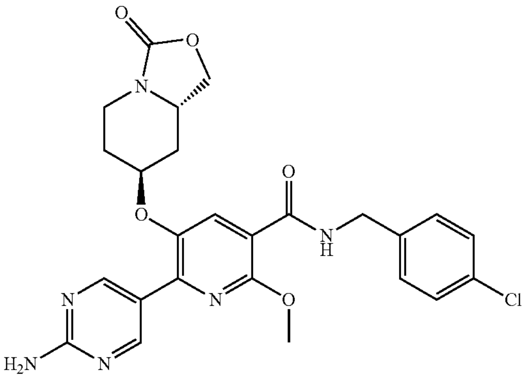 [SMILES: COc1nc(-c2cnc(N)nc2)c(O[C@H]2CCN3C(=O)OC[C@@H]3C2)cc1C(=O)NCc1ccc(Cl)cc1] | 525.3 |

-continued
| Compound | Structure | MS [M + H] |
| --- | --- | --- |
| 46 | 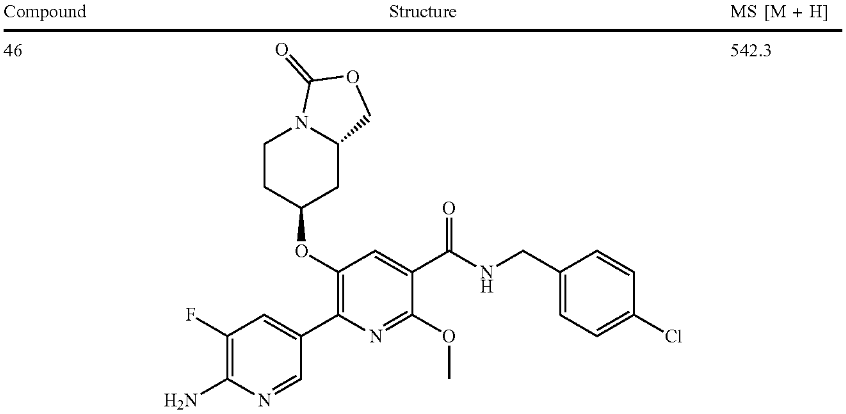 | 542.3 |
| 47 | 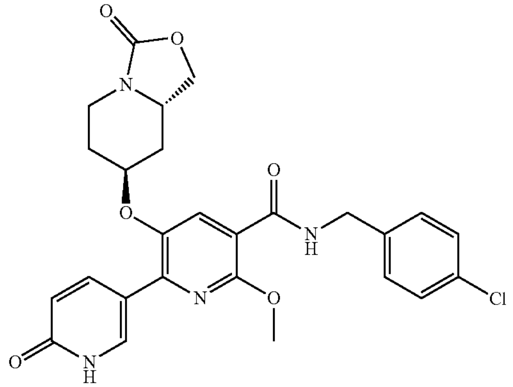 [SMILES: COc1nc(-c2ccc(=O)[nH]c2)c(O[C@H]2CCN3C(=O)OC[C@@H]3C2)cc1C(=O)NCc1ccc(Cl)cc1] | 525.3 |
| 48 | 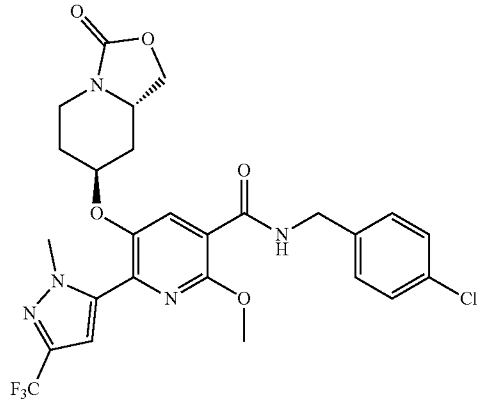 [SMILES: COc1nc(-c2cc(C(F)(F)F)nn2C)c(O[C@H]2CCN3C(=O)OC[C@@H]3C2)cc1C(=O)NCc1ccc(Cl)cc1] | 580.3 |
| 49 | 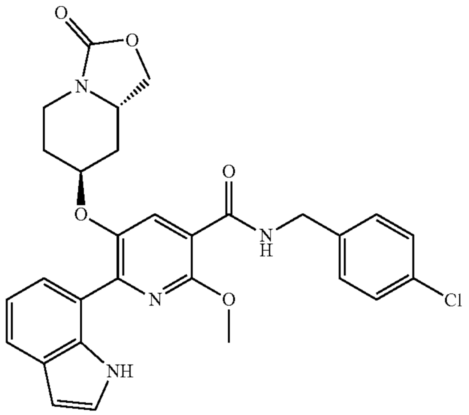 [SMILES: COc1nc(-c2cccc3cc[nH]c23)c(O[C@H]2CCN3C(=O)OC[C@@H]3C2)cc1C(=O)NCc1ccc(Cl)cc1] | 547.3 |

-continued
| Compound | Structure | MS [M + H] |
| --- | --- | --- |
| 50 | 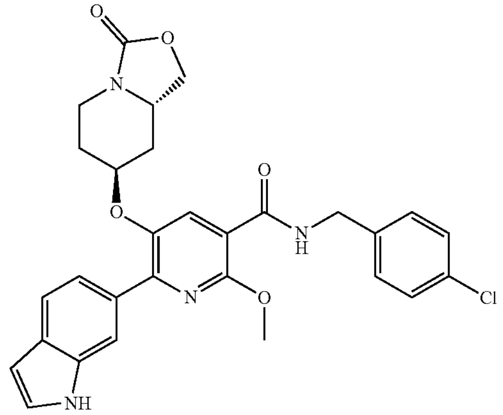 [SMILES: COc1nc(-c2ccc3cc[nH]c3c2)c(O[C@H]2CCN3C(=O)OC[C@@H]3C2)cc1C(=O)NCc1ccc(Cl)cc1] | 547.4 |
| 51 | 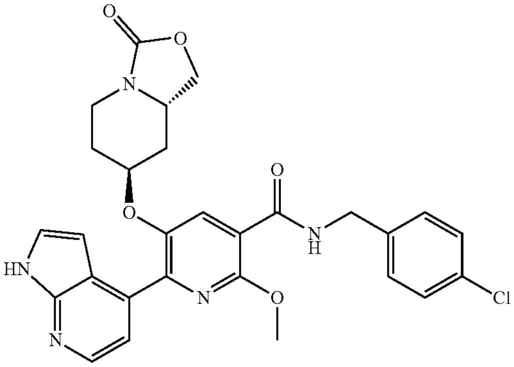 [SMILES: COc1nc(-c2ccnc3[nH]ccc23)c(O[C@H]2CCN3C(=O)OC[C@@H]3C2)cc1C(=O)NCc1ccc(Cl)cc1] | 548.3 |
| 52 | 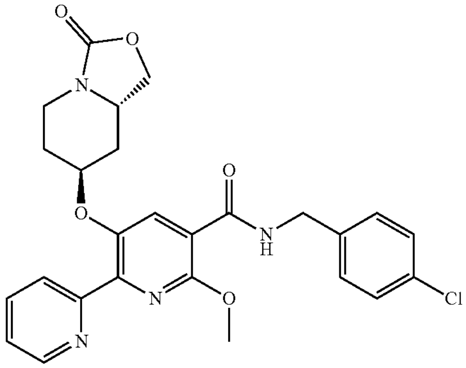 [SMILES: COc1nc(-c2ccccn2)c(O[C@H]2CCN3C(=O)OC[C@@H]3C2)cc1C(=O)NCc1ccc(Cl)cc1] | 509.3 |
| 53 | 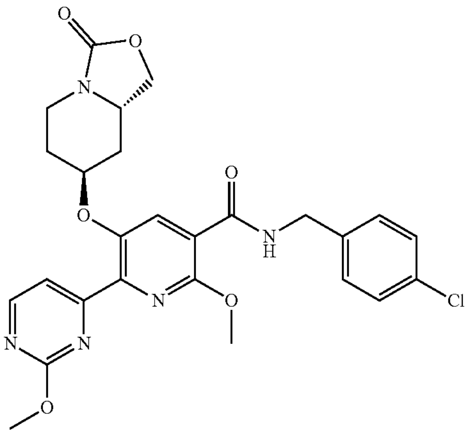 [SMILES: COc1nccc(-c2nc(OC)c(C(=O)NCc3ccc(Cl)cc3)cc2O[C@H]2CCN3C(=O)OC[C@@H]3C2)n1] | 540.3 |

-continued
| Compound | Structure | MS [M + H] |
|---|---|---|
| 54 | 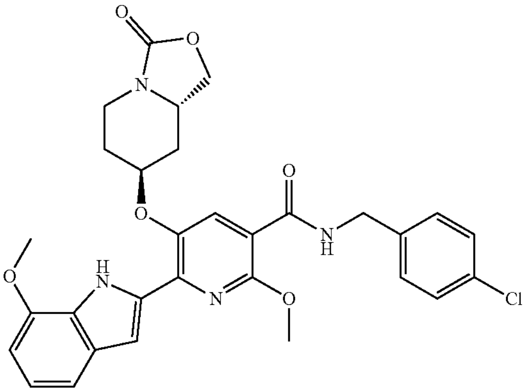 [SMILES: COc1nc(-c2cc3cccc(OC)c3[nH]2)c(O[C@H]2CCN3C(=O)OC[C@@H]3C2)cc1C(=O)NCc1ccc(Cl)cc1] | 577.4 |
The following compounds of the present invention were made using the methods described in Step C of Example 3 above, and Example 4, and substituting the appropriate reactants and/or reagents:
| Compound | Structure | MS [M + H] |
|---|---|---|
| 55 | 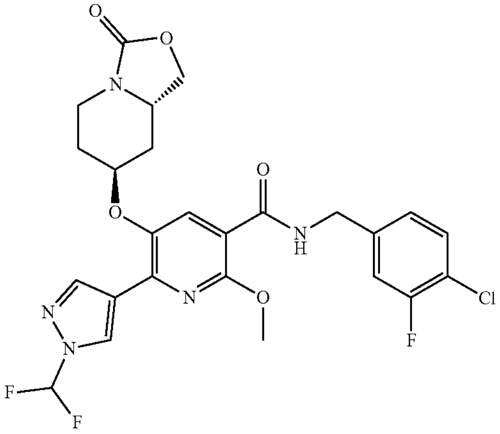 [SMILES: COc1nc(-c2cnn(C(F)F)c2)c(O[C@H]2CCN3C(=O)OC[C@@H]3C2)cc1C(=O)NCc1ccc(Cl)c(F)c1] | 566.2 |
| 56 | 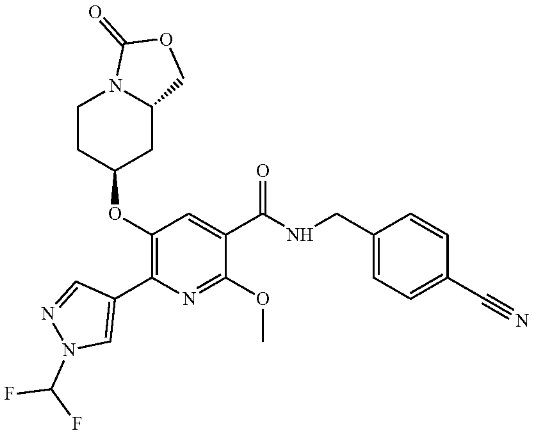 [SMILES: COc1nc(-c2cnn(C(F)F)c2)c(O[C@H]2CCN3C(=O)OC[C@@H]3C2)cc1C(=O)NCc1ccc(C#N)cc1] | 539.2 |

-continued
| Compound | Structure | MS [M + H] |
|---|---|---|
| 57 | 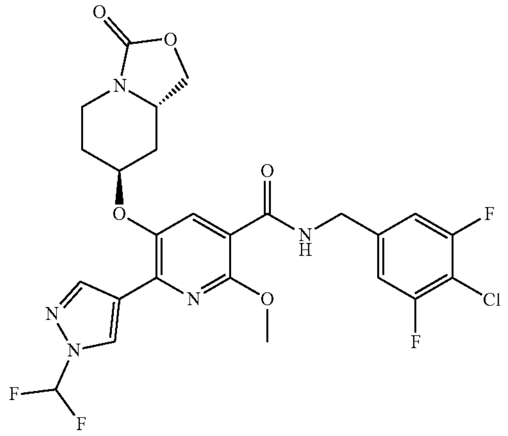 [SMILES: COc1nc(-c2cnn(C(F)F)c2)c(O[C@H]2CCN3C(=O)OC[C@@H]3C2)cc1C(=O)NCc1cc(F)c(Cl)c(F)c1] | 584.3 |
| 58 | 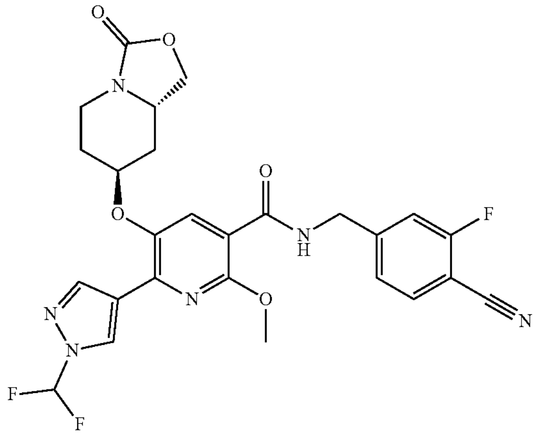 [SMILES: COc1nc(-c2cnn(C(F)F)c2)c(O[C@H]2CCN3C(=O)OC[C@@H]3C2)cc1C(=O)NCc1ccc(C#N)c(F)c1] | 557.2 |
| 59 | 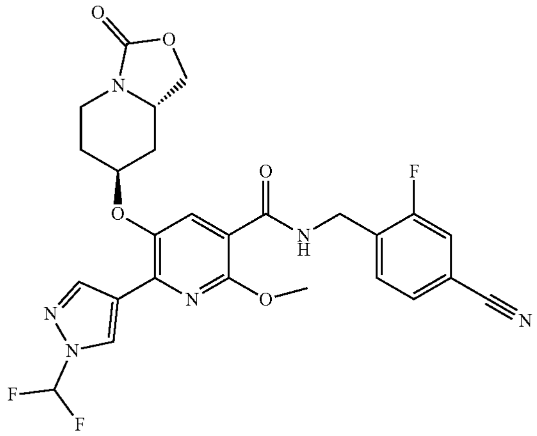 [SMILES: COc1nc(-c2cnn(C(F)F)c2)c(O[C@H]2CCN3C(=O)OC[C@@H]3C2)cc1C(=O)NCc1ccc(C#N)cc1F] | 557.3 |

Example 8

Preparation of Compound 60

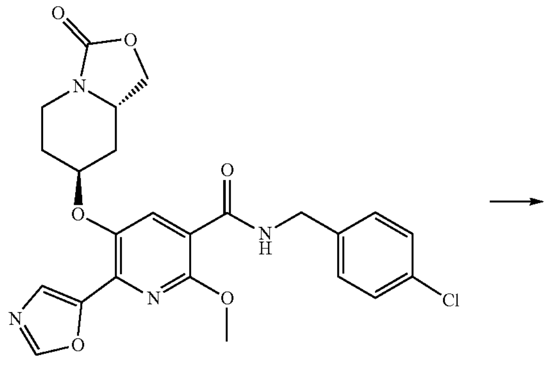

6

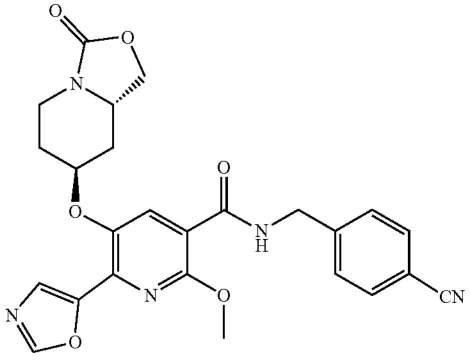

60

Step A—Synthesis of Compound 60

To a mixture of 6 (70 mg, 0.14 mmol) in DMF (0.5 mL) under nitrogen atmosphere, was added potassium phosphate (45 mg, 0.21 mmol), chloro(2-dicyclohexylphosphino-2',4',6'-tri-i-propyl-1,1'-biphenyl)(2'-amino-1,1'-biphenyl-2-yl) palladium(II) (11 mg, 0.014 mmol), and zinc cyanide (25 mg, 0.21 mmol). The resulting mixture was irradiated for 3 hours at 150° C., the reaction was quenched with water (10 mL) and extracted with ethyl acetate. The organic extract was washed with brine, dried over $Na_2SO_4$, filtered, and concentrated in vacuo. The resulting residue was purified using preparative HPLC (reverse-phase C-18), eluting with acetonitrile/water+0.1% TFA 35-55% to provide compound 60. MS: m/z 490.3=[M+H]. $^1H$ NMR (400 MHz, dimethyl sulfoxide-$d_6$, ppm): δ9.01 (t, J=6.0 Hz, 1H), 8.63 (s, 1H), 8.05 (s, 1H), 7.84-7.81 (m, 3H), 7.55-7.53 (m, 2H), 5.13 (s, 1H), 4.62-4.60 (m, 2H), 4.41-4.36 (m, 1H), 4.04 (s, 3H), 4.02-4.00 (m, 1H), 3.99-3.88 (m, 1H), 3.62-3.57 (m, 1H), 3.17-3.08 (m, 1H), 2.21-2.15 (m, 1H), 1.96-1.92 (m, 1H), 1.81-1.65 (m, 2H).

Example 9

Preparation of Compound 61

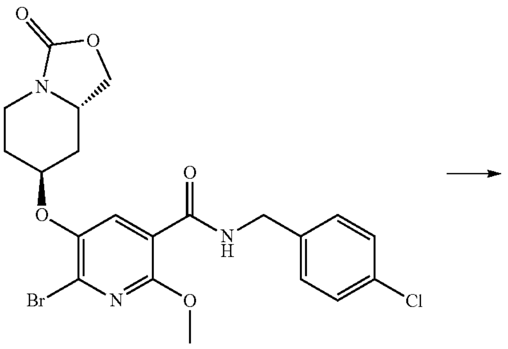

Int-3

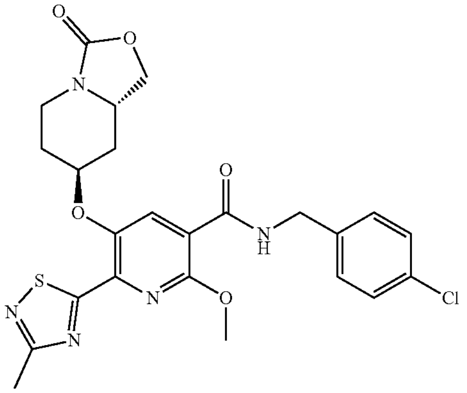

61

Step A—Synthesis of Compound 61

A solution of Int-3 (903 mg, 1.77 mmol), and 3-methyl-5-(tributylstannyl)-1,2,4-thiadiazole (679 mg, 1.75 mmol) in dioxane (11 mL) was purged subsurface with nitrogen. Tetrakis(triphenylphosphine)palladium(0) (204 mg, 0.177 mmol) was added, and the reaction was irradiated for 30 minutes at 150° C. The reaction was diluted with water, and brine, then extracted with ethyl acetate, washed with brine, dried over $MgSO_4$, and concentrated in vacuo. The resulting residue was passed through a column of 10% powdered potassium carbonate on silica gel, eluting with 60% (3:1 EtOAc:EtOH)/hexanes, to remove bulk tin byproducts. After concentrating the fractions containing the product, the residue was further purified using silica gel chromatography, eluting with 0-60% (3:1 EtOAc:EtOH) in hexanes. The collected product was then further purified using silica gel chromatography, eluting with 0-60% EtOAc in hexanes, to provide compound 61. MS: m/z 530.4=[M+H]. $^1H$ NMR (500 MHz, $CDCl_3$, ppm) δ8.39 (s, 1H), 8.38 (t, J=6.0 Hz, 1H), 7.34 (d, J=8.5 Hz, 2H), 7.28 (d, J=8.5 Hz, 2H), 5.13 (s, 1H), 4.65 (d, J=6.0 Hz, 2H), 4.37-4.46 (m, 2H), 4.18 (s, 3H), 3.94 (dd, J=8.0, 5.0 Hz, 1H), 3.83 (dd, J=8.0, 4.5 Hz, 1H), 3.51 (dt, J=13.0, 3.0 Hz, 1H), 2.77 (s, 3H), 2.29 (dd, J=13.5, 1.5 Hz, 1H), 2.10 (dd, J=14.5, 1.5 Hz, 1H), 1.83-1.90 (m, 1H), 1.74-1.79 (m, 1H).

The following compounds of the present invention were made using the methods described in Example 9 above, and substituting the appropriate reactants and/or reagents:

| Compound | Structure | MS [M + H] |
|---|---|---|
| 62 | 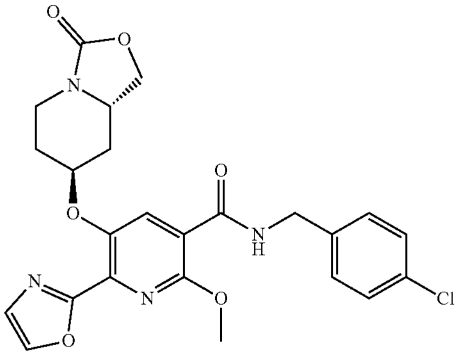 [SMILES: COc1nc(-c2ncco2)c(O[C@H]2CCN3C(=O)OC[C@@H]3C2)cc1C(=O)NCc1ccc(Cl)cc1] | 499.4 |
| 63 | 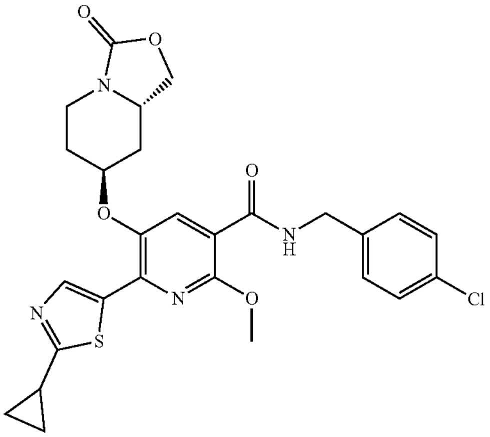 | 555.1 |
The following compounds of the present invention were made using the methods described in Step C of Example 3 above, and Example 4, and substituting the appropriate reactants and/or reagents:
| Compound | Structure | MS [M + H] |
|---|---|---|
| 64 | 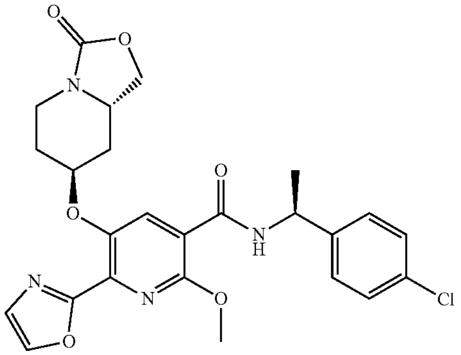 [SMILES: COc1nc(-c2ncco2)c(O[C@H]2CCN3C(=O)OC[C@@H]3C2)cc1C(=O)N[C@@H](C)c1ccc(Cl)cc1] | 513.1 |

Example 10

Preparation of Compound 65

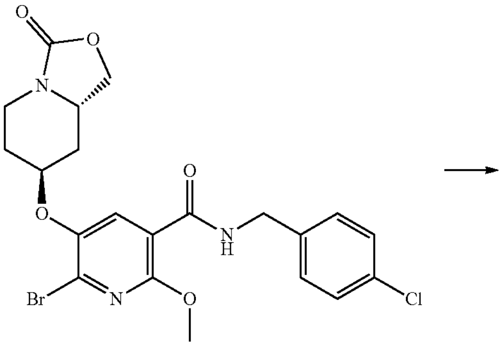

Int-3

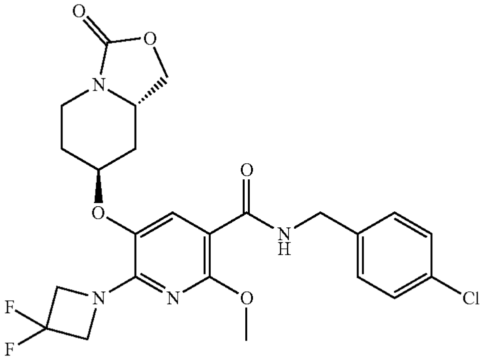

65

Step A—Synthesis of Compound 65

A solution of Int-3 (80 mg, 0.16 mmol), 3,3-difluoroazetidine hydrochloride (26.4 mg, 0.204 mmol), and cesium carbonate (179 mg, 0.548 mmol) in dioxane (1.0 mL) was purged subsurface with nitrogen. Methanesulfonato(2-dicyclohexylphosphino-2',6'-di-i-propoxy-1,1'-biphenyl)(2'-amino-1,1'-biphenyl-2-yl)palladium(II) (20 mg, 0.023 mmol) was added, and the reaction was heated to 115° C., and allowed to stir at this temperature for about 15 hours. The reaction was diluted with water, extracted with ethyl acetate, and the organic extract was washed with brine, dried over $MgSO_4$, filtered, and concentrated in vacuo. The resulting residue was purified using preparative HPLC (reverse-phase C-18), eluting with acetonitrile/water+0.1% TFA 10-80% to provide compound 65 as a foam. MS: m/z 523.4=[M+H]. $^1$H NMR (500 MHz, $CDCl_3$, ppm) δ8.15 (s, 1H), 7.90 (s, 1H), 7.32 (d, J=8.5 Hz, 2H), 7.28 (d, J=8.5 Hz, 2H), 4.81 (s, 1H), 4.62 (d, J=6.0 Hz, 2H), 4.55 (t, J=12.0 Hz, 4H), 4.46 (t, J=8.0 Hz, 1H), 3.98-4.03 (m, 1H), 3.99 (s, 3H), 3.93 (dd, J=8.5, 5.5 Hz, 1H), 3.86 (dd, J=13.0, 5.0 Hz, 1H), 3.21 (dt, J=13.5, 3.5 Hz, 1H), 2.23 (d, J=14.0 Hz, 1H), 2.05 (d, J=14.0 Hz, 1H), 1.77-1.83 (m 1H), 1.63-1.69 (m, 1H).

The following compounds of the present invention were made using the methods described in Example 10 above, and substituting the appropriate reactants and/or reagents:

| Compound | Structure | MS [M + H] |
|---|---|---|
| 66 | 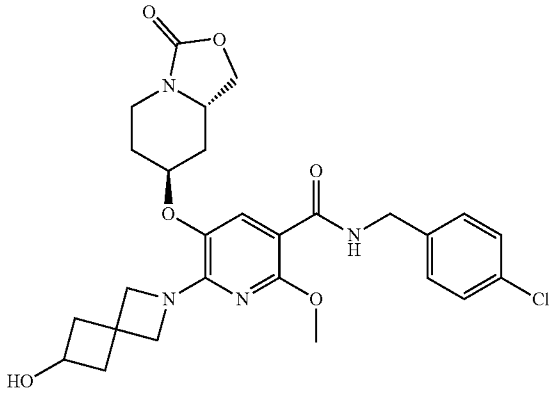 [SMILES: COc1nc(N2CC3(CC(O)C3)C2)c(O[C@H]2CCN3C(=O)OC[C@@H]3C2)cc1C(=O)NCc1ccc(Cl)cc1] | 543.3 |

-continued
| Compound | Structure | MS [M + H] |
|---|---|---|
| 67 | 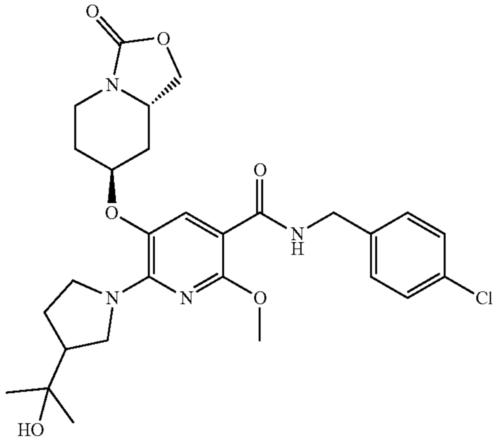 (R or S), first peak resolved by CHIRAL ART Cellulose-SB, hexane:ethanol-1:1 | 559.4 |
| 68 | 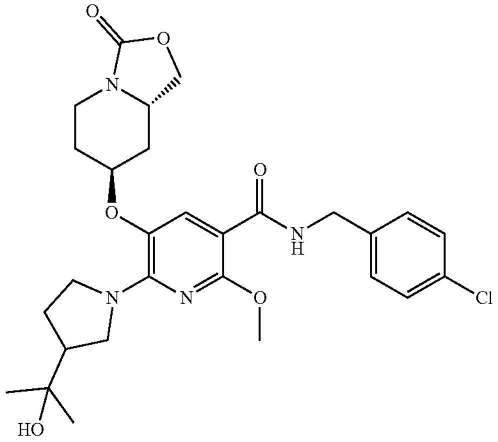 (R or S), second peak resolved by CHIRAL ART Cellulose-SB, hexane:ethanol-1:1 | 559.4 |
| 69 | 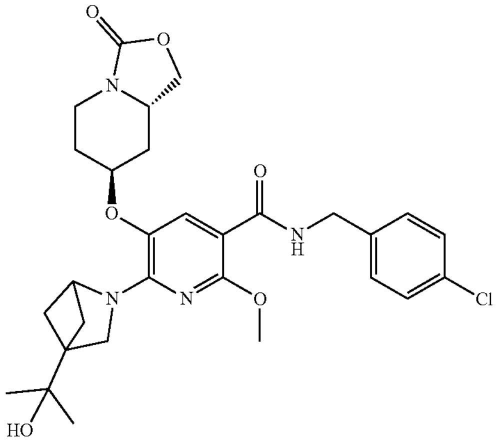 [SMILES: COc1nc(N2CC3(C(C)(C)O)CC2C3)c(O[C@H]2CCN3C(=O)OC[C@@H]3C2)cc1C(=O)NCc1ccc(Cl)cc1] | 571.2 |

-continued
| Compound | Structure | MS [M + H] |
|---|---|---|
| 70 | 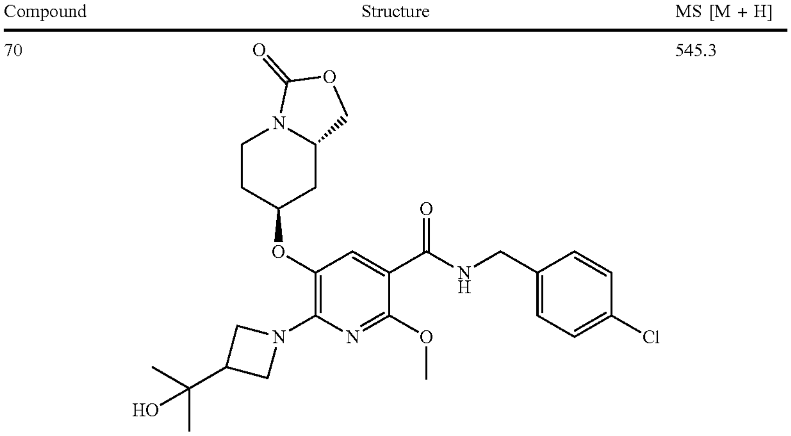 | 545.3 |
Example 11
Preparation of Compounds 71 and 72
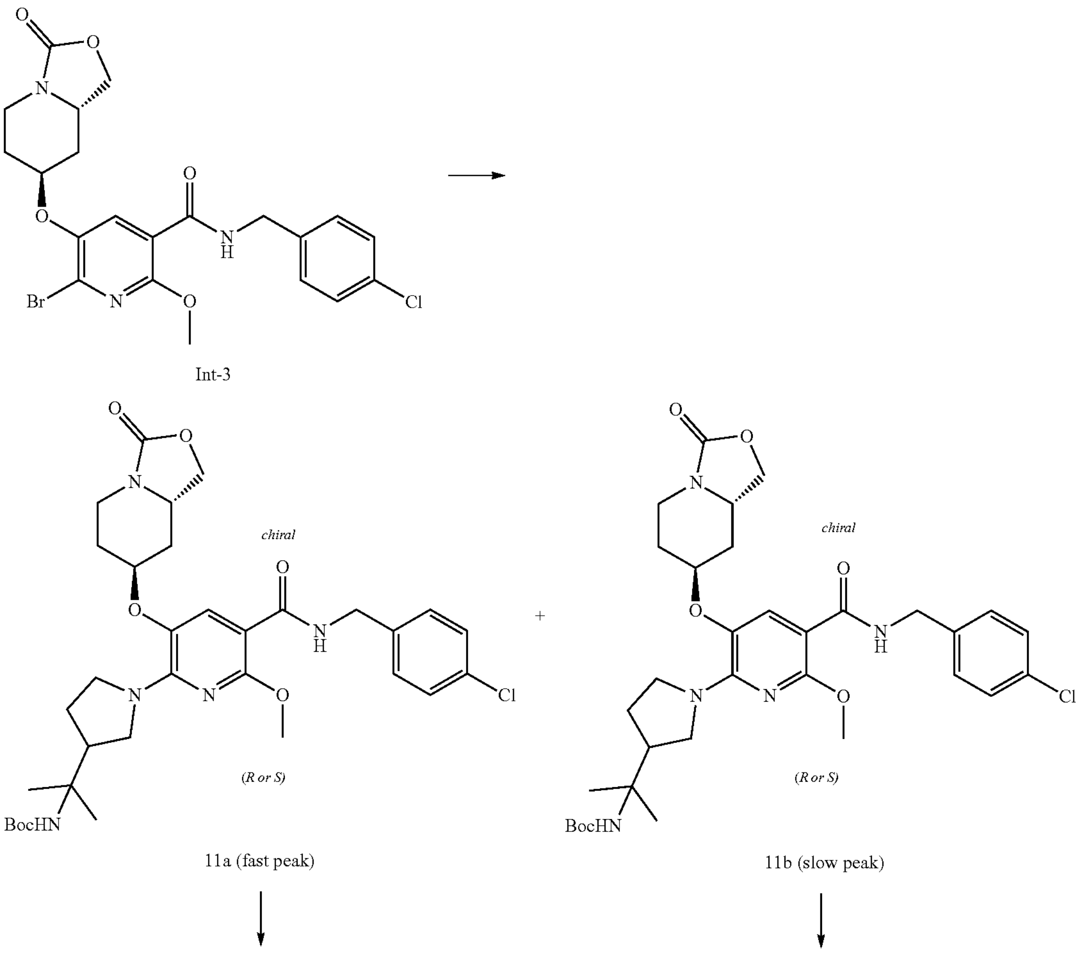
Int-3
11a (fast peak)
11b (slow peak)

-continued

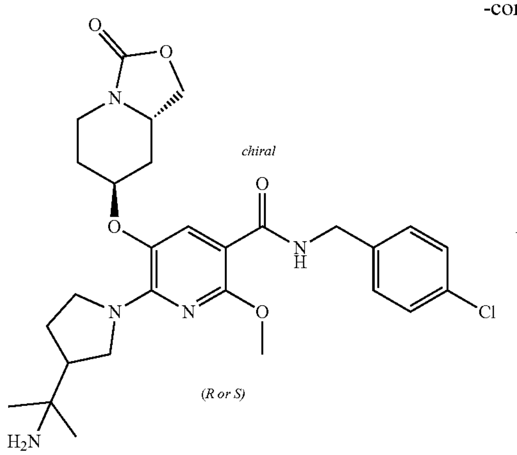

+

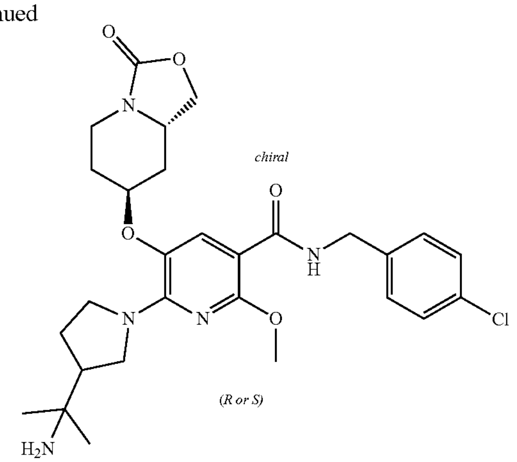

71

72

Step A—Synthesis of Compounds 11a and 11b

A mixture of cesium carbonate (191 mg, 0.587 mmol), Int-3 (150 mg, 0.294 mmol), $Ad_2$n-BuP palladacycle G2 (20 mg, 0.029 mmol), tert-butyl (2-(pyrrolidin-3-yl)propan-2-yl)carbamate (94 mg, 0.41 mmol), and 2,2'-bis(diphenylphosphino)-1,1'-binaphthalene (18 mg, 0.029 mmol) in dioxane (5 mL) was allowed to stir for 3 hours at 90° C. under nitrogen atmosphere. The reaction mixture was quenched with water (20 mL), and the mixture was extracted with ethyl acetate. The organic extract was washed with brine, dried over $Na_2SO_4$, filtered and concentrated in vacuo. The resulting residue was resolved using chiral HPLC (column: CHIRAL ART Cellulose), eluting with a gradient of hexane:dichloromethane:isopropanol—3:1:4 to provide 11a (fast peak), MS: m/z 658.3=[M+H], and 11b (slow peak), MS: m/z 658.3=[M+H].

Step B—Synthesis of Compound 71

To a mixture of 11a (52 mg, 0.079 mmol) in dichloromethane (1 mL) was added trifluoroacetic acid (1 mL). The resulting mixture was allowed to stir for 2 hours at room temperature. The reaction mixture was concentrated in vacuo, and the residue obtained was diluted with saturated sodium bicarbonate (10 mL), then extracted with ethyl acetate. The organic extract was washed with brine, dried over $Na_2SO_4$, filtered, and concentrated in vacuo to provide 71. MS: m/z 558.3=[M+H]. $^1$H NMR (400 MHz, methanol-$d_4$, ppm): δ7.68 (s, 1H), 7.31 (s, 4H), 4.72 (s, 1H), 4.55 (s, 2H), 4.45 (t, J=8.4 Hz, 1H), 4.11-4.09 (m, 1H), 4.04-3.89 (m, 6H), 3.78-3.70 (m, 2H), 3.59-3.54 (m, 1H), 3.33-3.26 (m, 1H), 2.30-2.24 (m, 2H), 2.09-2.00 (m, 2H), 1.83-1.76 (m, 2H), 1.70-1.64 (m, 1H), 1.18 (s, 6H).

Step C—Synthesis of Compound 72

Compound 72 was made from 11b, using the method described in Example 11, step B. MS: m/z 558.3=[M+H]. $^1$H NMR (400 MHz, methanol-$d_4$, ppm): δ7.68 (s, 1H), 7.33 (s, 4H), 4.72 (s, 1H), 4.57 (s, 2H), 4.49 (t, J=8.4 Hz, 1H), 4.17-4.15 (m, 1H), 4.06-3.91 (m, 6H), 3.79-3.71 (m, 2H), 3.58 (t, J=10.8 Hz, 1H), 3.33-3.25 (m, 1H), 2.30-2.28 (m, 2H), 2.07-2.02 (m, 2H), 1.82-1.67 (m, 3H), 1.20 (s, 6H).

Example 12

Preparation of Compound 73

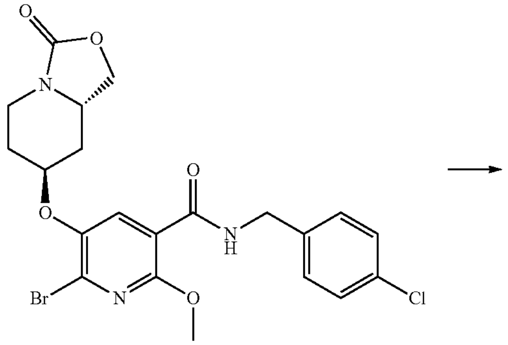

Int-3

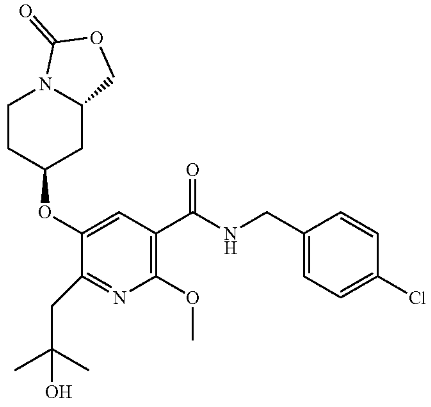

73

Step A—Synthesis of Compound 75

A mixture of 1,1,1,3,3,3-hexamethyl-2-(trimethylsilyl)trisilane (78 mg, 0.31 mmol), Int-3 (80 mg, 0.16 mmol), 1-bromo-2-methylpropan-2-ol (48 mg, 0.31 mmol), nickel (II) chloride ethylene glycol dimethyl ether complex (0.30 mg, 1.6 μmol), Ir[dF($CF_3$)ppy]$_2$(dtbbpy)$PF_6$ (3.5 mg, 3.1 μmol), 2,6-dimethylpyridine (33.6 mg, 0.314 mmol), and 4,4'-di-tert-butyl-2,2'-bipyridine (0.421 mg, 1.57 μmol) in ethylene glycol dimethyl ether (3 mL) was irradiated with blue LED (400 nm, 15 W, with active fan cooling) for 2 hours at room temperature under argon. The resulting mixture was quenched with water (10 mL) and extracted with ethyl acetate. The organic extract was washed with brine, dried over $Na_2SO_4$, filtered, and concentrated in vacuo. The resulting residue was purified using preparative HPLC (reverse-phase C-18), eluting with acetonitrile/water+10 mmol/mL ammonium bicarbonate 50-75% to provide compound 73. MS: m/z 504.2=[M+H]. $^1$H NMR (400 MHz, methanol-$d_4$, ppm): δ8.00 (s, 1H), 7.38-7.33 (m, 4H), 4.62 (s, 2H), 4.49 (t, J=8.4 Hz, 1H), 4.25-4.18 (m, 1H), 4.09 (s, 3H), 4.02-3.98 (m, 1H), 3.75 (dd, J=5.2, 13.6 Hz, 1H), 3.39-3.33 (m, 1H), 3.23 (dd, J=7.2, 14.8 Hz, 1H), 3.07 (s, 2H), 2.28-2.23 (m, 1H), 2.06 (d, J=14.4 Hz, 1H), 1.90-1.70 (m, 2H), 1.32 (s, 6H).

Example 13

Preparation of Compound 74

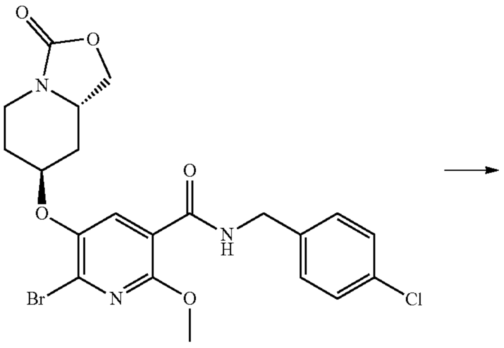

Int-3

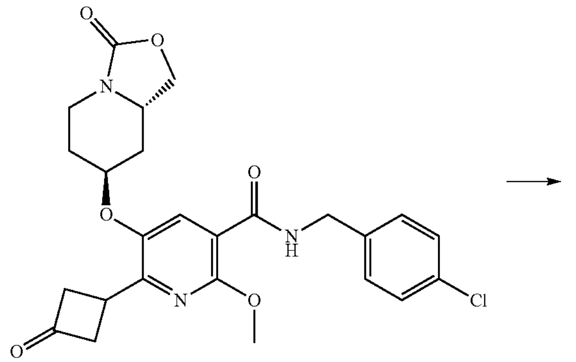

13a

-continued

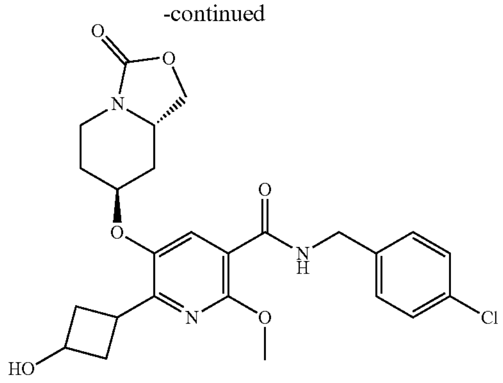

cis or trans

74

Step A—Synthesis of Compound 13a

A mixture of 3-bromocyclobutanone (117 mg, 0.783 mmol), Int-3 (200 mg, 0.392 mmol), 1,1,1,3,3,3-hexamethyl-2-(trimethylsilyl)trisilane (195 mg, 0.783 mmol), nickel (II) chloride ethylene glycol dimethyl ether complex (0.860 mg, 3.92 μmol), Ir[dF($CF_3$)ppy]$_2$(dtbbpy)$PF_6$ (8.8 mg, 78 μmol), 2,6-dimethylpyridine (83.9 mg, 7.83 mmol), and 4,4'-di-tert-butyl-2,2'-bipyridine (1.1 mg, 3.9 μmol) in ethylene glycol dimethyl ether (3 mL) was irradiated with blue LED (400 nm, 15 W), and active fan cooling for 2 hours at room temperature under argon. The resulting mixture was quenched with water (10 mL) and extracted with ethyl acetate. The organic extract was washed with brine, dried over $Na_2SO_4$, filtered, and concentrated in vacuo. The resulting residue was purified using silica gel chromatography, eluting with 0-10% MeOH in $CH_2Cl_2$ to provide 13a. MS: m/z 500.2=[M+H].

Step B—Synthesis of Compound 74

To a mixture of 13a (100 mg, 0.200 mmol) in tetrahydrofuran (4 mL) was added sodium borohydride (6.05 mg, 0.160 mmol) at 0° C. The reaction mixture was allowed to stir for 1 hour at room temperature, then quenched with saturated aqueous ammonium chloride (15 mL) and extracted with ethyl acetate. The organic extract was washed with brine, dried over $Na_2SO_4$, filtered and concentrated in vacuo, and the resulting residue was purified using preparative TLC, eluting with 5% MeOH in $CH_2Cl_2$, to provide a mixture of diastereomers, which was resolved using chiral HPLC (column: CHIRALPAK IA), eluting with a gradient of hexane: ethanol—1:1 to provide 74 (slow peak, major). MS: m/z 502.2=[M+H]. $^1$H NMR (400 MHz, methanol-$d_4$, ppm): δ7.92 (s, 1H), 7.38-7.34 (m, 4H), 4.87-4.84 (m, 1H), 4.62 (s, 2H), 4.50 (t, J=8.4 Hz, 1H), 4.32-4.21 (m, 1H), 4.18-4.14 (m, 4H), 4.02-3.97 (m, 1H), 3.76-3.71 (m, 1H), 3.51-3.47 (m, 1H), 3.45-3.37 (m, 1H), 2.67-2.60 (m, 2H), 2.40-2.32 (m, 2H), 2.26-2.23 (m, 1H), 2.06-2.02 (m, 1H), 1.85-1.71 (m, 2H).

Example 14

Preparation of Compound 75

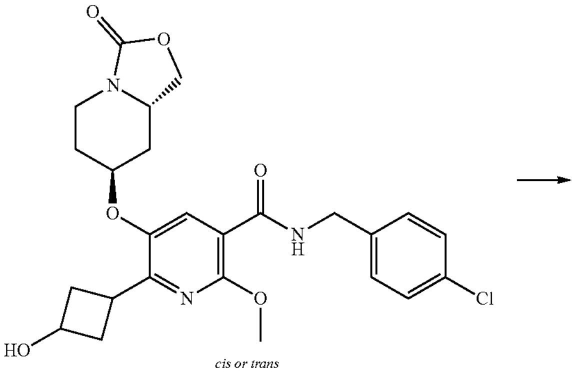

cis or trans

74

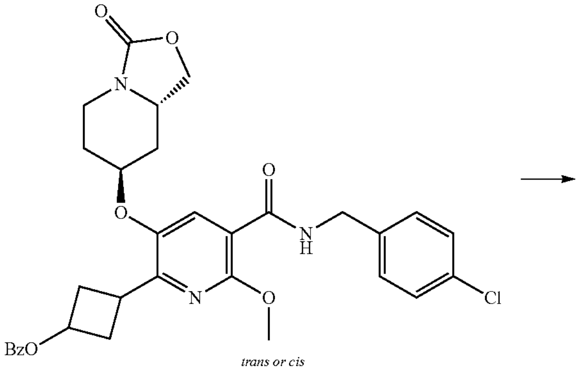

trans or cis

14a

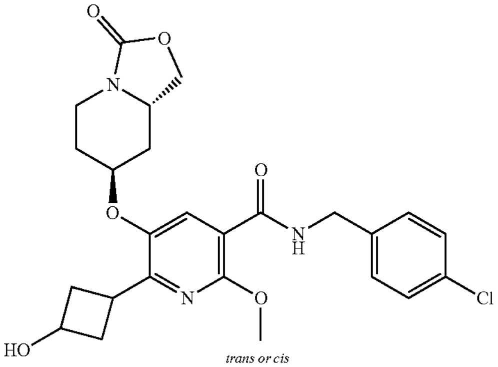

trans or cis

75

Step A—Synthesis of Compound 14a

To a mixture of triphenylphosphine (47.0 mg, 0.179 mmol) in tetrahydrofuran (2 mL), at 0° C., was added di-tert-butyl diazene-1,2-dicarboxylate (41.3 mg, 0.179 mmol). The reaction was allowed to stir for 30 minutes at 0° C., then compound 77 (30 mg, 0.060 mmol), and benzoic acid (11 mg, 0.090 mmol) were added, and the resulting reaction was allowed to stir for 2 hours at room temperature. The reaction mixture was concentrated in vacuo, and the resulting residue was purified using preparative TLC, eluting with ethyl acetate, to provide 14a. MS: m/z 606.4=[M+H].

Step B—Synthesis of Compound 75

To a mixture of 14a (25 mg, 0.041 mmol) in tetrahydrofuran (1.5 mL), methanol (0.5 mL), and water (0.5 mL) was added lithium hydroxide (1.98 mg, 0.082 mmol). The resulting reaction was allowed to stir for 16 hours at room temperature, then the reaction mixture was diluted with water (10 mL) and extracted with ethyl acetate. The organic extract was washed with brine, dried over $Na_2SO_4$, filtered, and concentrated in vacuo. The resulting residue was purified using preparative TLC, eluting with ethyl acetate to provide 75. MS: m/z 502.2=[M+H]. $^1H$ NMR (400 MHz, methanol-$d_4$, ppm): δ7.93 (s, 1H), 7.59-7.34 (m, 4H), 4.86-4.83 (m, 1H), 4.66-4.60 (m, 3H), 4.50 (t, J=8.4 Hz, 1H), 4.16-4.01 (m, 4H), 4.00-3.95 (m, 2H), 3.76-3.71 (m, 1H), 3.37-3.26 (m, 1H), 2.66-2.64 (m, 2H), 2.43-2.40 (m, 2H), 2.39-2.22 (m, 1H), 2.04-2.00 (m, 1H), 1.85-1.71 (m, 2H).

Example 15

Preparation of Compound 76

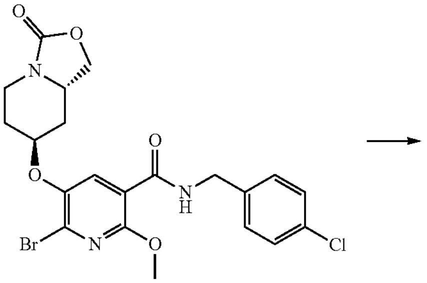

Int-3

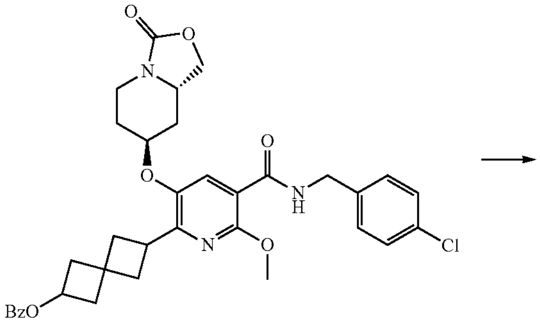

15a

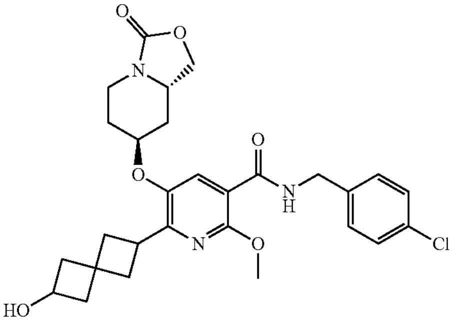

76

Step A—Synthesis of Compound 15a

A mixture of Int-3 (100 mg, 0.200 mmol), 6-bromospiro[3.3]heptan-2-yl benzoate (87 mg, 0.30 mmol), 1,1,1,3,3,3-hexamethyl-2-(trimethylsilyl)trisilane (97 mg, 0.40 mmol), nickel (II) chloride ethylene glycol dimethyl ether complex (0.40 mg, 2.0 μmol), $Ir[dF(CF_3)ppy]_2(dtbbpy)PF_6$ (4.4 mg, 3.9 μmol), sodium carbonate (42 mg, 0.40 mmol), and 4,4'-di-tert-butyl-2,2'-bipyridine (0.50 mg, 2.0 μmol) in ethylene glycol dimethyl ether (3 mL) was irradiated with blue LED (400 nm, 15 W, with active fan cooling) for 2 hours at room temperature under argon atmosphere. The reaction mixture was quenched with water (20 mL), extracted with ethyl acetate, and the organic extracted washed with brine, dried over $Na_2SO_4$, filtered, and concentrated in vacuo. The resulting residue was purified using preparative HPLC (reverse-phase C-18), eluting with 25% acetonitrile/water+10 mmol/L ammonium bicarbonate to provide compound 15a. MS: m/z 646.3=[M+H].

Step B—Synthesis of Compound 76

To a mixture of 15a (40 mg, 0.062 mmol) in tetrahydrofuran (1.5 mL), methanol (0.5 mL), and water (0.500 mL), was added lithium hydroxide (2.97 mg, 0.124 mmol), and the resulting mixture was allowed to stir for 2 hours at room temperature. The reaction mixture was quenched with water (20 mL) and extracted with ethyl acetate. The organic phase was washed with brine, dried over $Na_2SO_4$, filtered, and concentrated in vacuo, and the resulting residue was purified using preparative HPLC (reverse-phase C-18), eluting with acetonitrile/water+0.05% TFA 55-70% to provide compound 76. MS: m/z 542.2=[M+H]. $^1$H NMR (400 MHz, methanol-$d_4$, ppm): δ7.87 (s, 1H), 7.32 (s, 4H), 4.78 (s, 1H), 4.58 (s, 2H), 4.47 (t, J=8.4 Hz, 1H), 4.14-4.09 (m, 4H), 4.03-4.02 (m, 1H), 3.98-3.95 (m, 1H), 3.89-3.85 (m, 1H), 3.74-3.32 (m, 1H), 3.31-3.26 (m, 1H), 2.68-2.10 (m, 7H), 2.03-1.98 (m, 2H), 1.92-1.89 (m, 1H), 1.87-1.68 (m, 2H).

Example 16

Preparation of Compounds 77, 78, 79, and 80

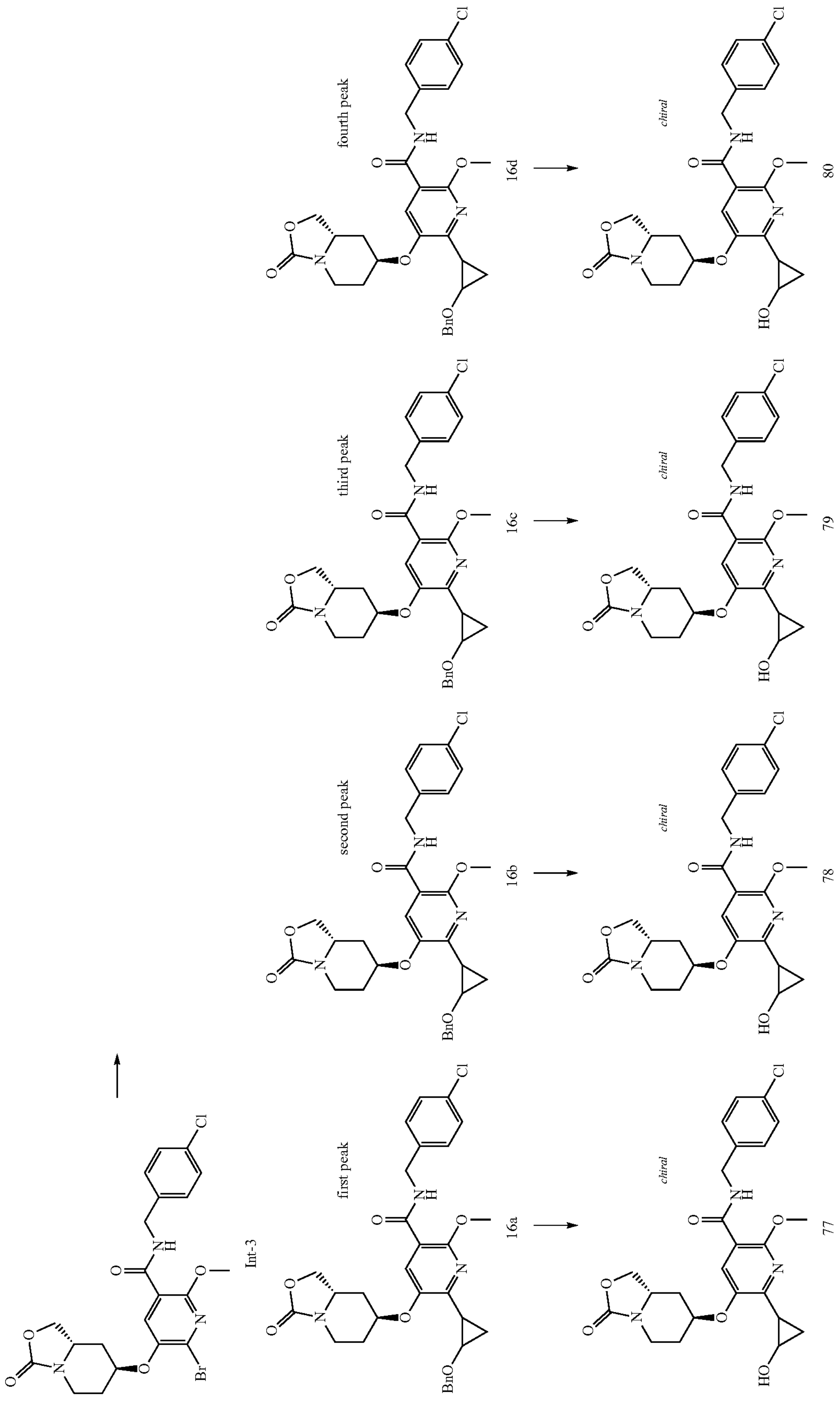
Int-3
16a
16b
16c
16d
77
78
79
80

Step A—Synthesis of Compounds 16a, 16b, 16c, and 16d

To a mixture of Int-3 (200 mg, 0.392 mmol), and potassium (2-(benzyloxy)cyclopropyl)trifluoroborate (199 mg, 0.783 mmol) in toluene (3 mL), and water (2 mL) was added cesium carbonate (383 mg, 1.18 mmol), followed by 1,1'-bis(di-tert-butylphosphino)ferrocene palladium dichloride (25.5 mg, 0.039 mmol), and the resulting reaction was put under argon atmosphere. The reaction was allowed to stir for 2 hours at 100° C., then quenched with water (20 mL), extracted with ethyl acetate. The organic phase was washed with brine, dried over $Na_2SO_4$, filtered, and concentrated in vacuo, and the resulting residue was purified using silica gel chromatography, eluting with 0-58% EtOAc in petroleum ether, to provide a mixture of 4 diastereomers. MS: m/z 578.1=[M+H]. The compounds were resolved using chiral HPLC (column: CHIRAL ART Cellulose-SB), eluting with a gradient of methyl tertiary butyl ether:isopropanol—80:20 to provide 16a, 16b, 16c, and 16d as isolated compounds.

Step B—Synthesis of Compound 77

A mixture of 16a (first eluting peak from Step A, 4.0 mg, 6.9 μmol) in trifluoroacetic acid (0.5 mL) was allowed to stir for 1 hour at 65° C. The reaction mixture was then concentrated in vacuo, and the residue obtained was directly purified using preparative HPLC (reverse-phase C-18), eluting with acetonitrile/water+10 mmol/mL ammonium bicarbonate 45-60% to provide compound 77. MS: m/z 488.1=[M+H]. $^1$H NMR (400 MHz, methanol-$d_4$, ppm) δ7.95 (s, 1H), 7.35 (s, 4H), 4.65-4.61 (m, 3H), 4.49-4.47 (m, 1H), 4.26-4.17 (m, 1H), 4.07 (s, 3H), 4.02-3.97 (m, 1H), 3.73-3.71 (m, 1H), 3.39-3.32 (m, 1H), 2.97-2.93 (m, 2H), 2.26-2.22 (m, 1H), 2.09-2.03 (m, 3H), 1.90-1.70 (m, 2H).

Step C—Synthesis of Compound 78

Compound 78 was made from compound 16b, using the method described in step B. MS: m/z 488.4=[M+H]. $^1$H NMR (400 MHz, methanol-d4, ppm) δ7.95 (s, 1H), 7.35 (s, 4H), 4.66-4.61 (m, 3H), 4.51-4.47 (m, 1H), 4.23-4.21 (m, 1H), 4.07 (s, 3H), 4.04-3.96 (m, 1H), 3.73-3.71 (m, 1H), 3.40-3.32 (m, 1H), 2.97-2.93 (m, 2H), 2.26-2.24 (m, 1H), 2.09-2.02 (m, 3H), 1.78-1.72 (m, 2H).

Step D—Synthesis of Compound 79

Compound 79 was made from compound 16c, using the method described in step B. MS: m/z 488.4=[M+H]. $^1$H NMR (400 MHz, methanol-d4, ppm) δ7.94 (s, 1H), 7.35 (s, 4H), 4.66-4.61 (m, 3H), 4.51-4.46 (m, 1H), 4.23-4.21 (m, 1H), 4.07 (s, 3H), 4.02-3.97 (m, 1H), 3.73-3.71 (m, 1H), 3.39-3.32 (m, 1H), 2.98-2.93 (m, 2H), 2.25-2.23 (m, 1H), 2.09-2.03 (m, 2H), 1.89-1.70 (m, 2H).

Step E—Synthesis of Compound 80

Compound 80 was made from compound 16d, using the method described in step B. MS: m/z 488.3=[M+H]. $^1$H NMR (400 MHz, methanol-d4, ppm) δ7.94 (s, 1H), 7.35 (s, 4H), 4.66-4.61 (m, 3H), 4.49 (t, J=8.8 Hz, 1H), 4.23-4.18 (m, 1H), 4.07 (s, 3H), 4.01-3.98 (m, 1H), 3.76-3.71 (m, 1H), 3.37-3.33 (m, 1H), 2.95-2.93 (m, 2H), 2.27-2.24 (m, 1H), 2.05-2.00 (m, 3H), 1.89-1.71 (m, 2H).

Example 17

Preparation of Compound 81

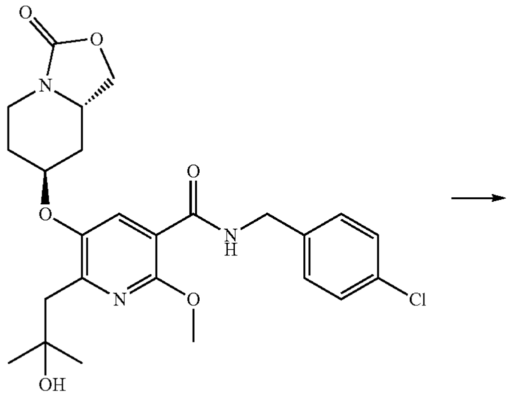

75

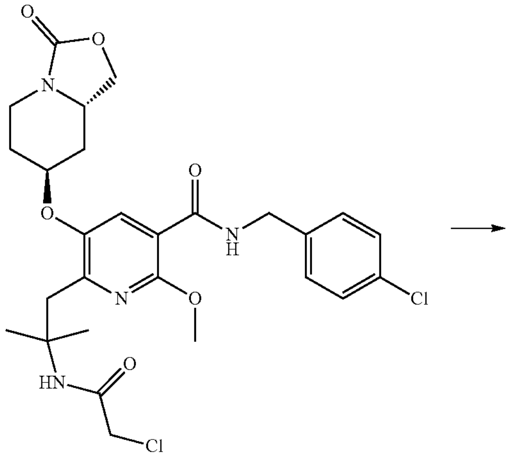

17a

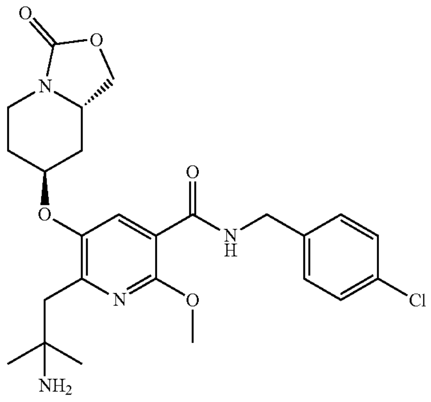

81

Step A—Synthesis of Compound 17a

A mixture of 75 (130 mg, 0.258 mmol), and chloroacetonitrile (195 mg, 2.58 mmol) in acetic acid (2 mL) was cooled to 0° C., then sulfuric acid (0.14 mL, 2.6 mmol) was added, and the mixture was heated to 80° C., and allowed to stir at this temperature for 16 hours. The reaction mixture was quenched with water (10 mL) and extracted with ethyl acetate. The organic extract was washed with brine, dried over $Na_2SO_4$, filtered, and concentrated in vacuo. The resulting residue was purified using preparative HPLC, eluting with acetonitrile/water+10 mmol/L ammonium bicarbonate 50-80% to provide 17a. MS: m/z 579.1=[M+H].

Step B—Synthesis of Compound 81

To a mixture of 17a (120 mg, 0.207 mmol) in acetic acid (100 μL), and ethanol (500 μl) was added thiourea (47 mg, 0.62 mmol). The resulting reaction was heated to 80° C., and allowed to stir at this temperature for 16 hours. The reaction was concentrated in vacuo, and the residue obtained was diluted with water (20 mL) and extracted with ethyl acetate. The organic extract was washed with brine, dried over $Na_2SO_4$, filtered, and concentrated in vacuo. The resulting residue was purified using preparative HPLC, eluting with acetonitrile/water+10 mmol/L ammonium bicarbonate 40-70% to provide 81. MS: m/z 503.3=[M+H]. $^1$H NMR (400 MHz, methanol-$d_4$, ppm): δ8.05 (s, 1H), 7.36-7.31 (m, 4H), 4.92 (s, 1H), 4.60 (s, 2H), 4.48 (t, J=8.4 Hz, 1H), 4.17-4.15 (m, 1H), 4.07 (s, 3H), 4.01-3.97 (m, 1H), 3.74 (dd, J=5.6, 13.2 Hz, 1H), 3.32-3.26 (m, 1H), 3.19 (s, 2H), 2.24 (d, J=14.0 Hz, 1H), 2.04 (d, J=14.4 Hz, 1H), 1.87-1.72 (m, 2H), 1.45 (s, 6H).

Example 18

Preparation of Compound 82

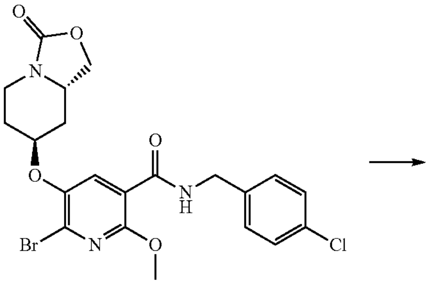

Int-3

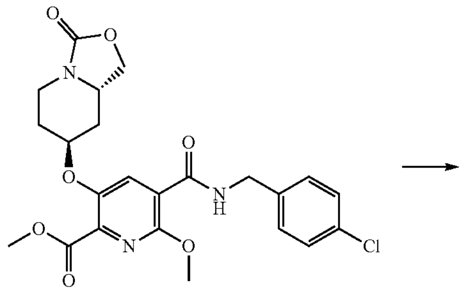

18a

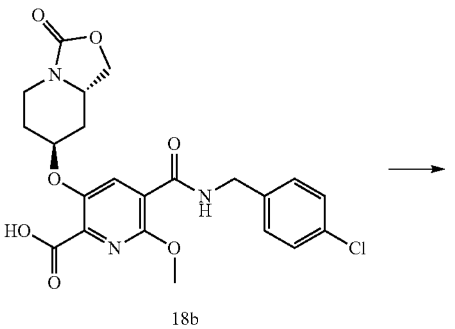

18b

-continued

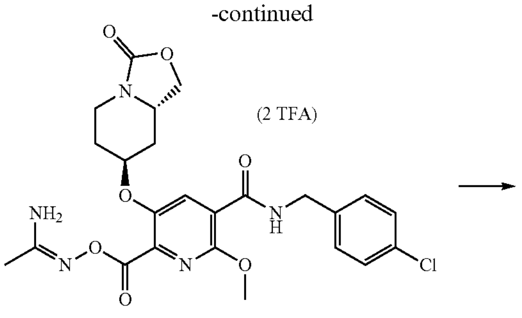

18c

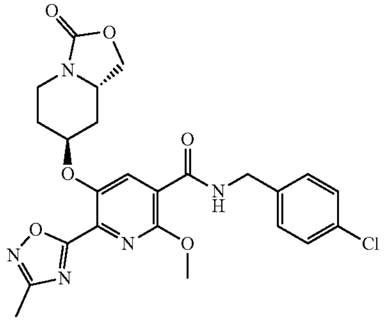

82

Step A—Synthesis of Compound 18a

To a mixture of Int-3 (600 mg, 1.18 mmol), and $PdCl_2$(dppf) (86.0 mg, 0.117 mmol) in MeOH (7.8 mL) was added DIEA (616 μl, 3.52 mmol), and the resulting reaction was heated at 80° C. under 80 psi of carbon monoxide for 14 hours. The reaction was concentrated in vacuo, and the residue obtained was purified using silica gel chromatography, eluting with 0-55% (3:1 EtOAc:EtOH) in hexanes, to provide 18a. MS: m/z 490.4=[M+H].

Step B—Synthesis of Compound 18b

To a mixture of 18a (52 mg, 0.11 mmol) in dioxane (2.5 mL) was added NaOH (1 M, 0.138 mL), and water (0.3 mL), and the resulting reaction was allowed to stir at room temperature for about 15 hours. The reaction mixture was concentrated in vacuo, and the residue obtained was taken up in acetonitrile and water, frozen, and lyophilized to provide 18b as a solid. MS: m/z 476.3=[M+H].

Step C—Synthesis of Compound 18c

To a mixture of 18b (65 mg, 0.11 mmol) in DMF (439 μL) was added carbonyl diimidazole (20.5 mg, 0.126 mmol), and the resulting solution was allowed to stir for 30 minutes, then was added a mixture of (Z)-N'-hydroxyacetimidamide (19.74 mg, 0.266 mmol) in pyridine (164 μL, 2.03 mmol), and the resulting reaction was allowed to stir at room temperature for 1 hour. The reaction mixture was concentrated in vacuo, and the resulting residue was purified using preparative HPLC (reverse-phase C-18), eluting with acetonitrile/water+0.1% TFA 10-60% to provide compound 18c as a solid. MS: m/z 532.5=[M+H].

Step D—Synthesis of Compound 22

To a mixture of 18c (44 mg, 0.058 mmol) in DMF (1.16 mL) was added triethylamine (32 μL, 0.23 mmol), and the resulting reaction was heated to 110° C., and allowed to stir at this temperature for 1 hour. Additional triethylamine (50 μL) was added, and the reaction was allowed to stir for an additional 3 hours at 110° C. The reaction was cooled to room temperature, filtered, and the filtrate weas concentrated in vacuo. The resulting residue was purified using preparative HPLC (reverse-phase C-18), eluting with acetonitrile/water+0.1% TFA 10-70% to provide compound 82 as a foam. MS: m/z 514.4=[M+H]. $^1$H NMR (500 MHz, $CDCl_3$, ppm) δ8.42 (t, J=5.5 Hz, 1H), 8.39 (s, 1H), 7.35 (d, J=8.5 Hz, 2H), 7.31 (d, J=8.5 Hz, 2H), 5.07 (s, 1H), 4.66 (d, J=5.5 Hz, 2H), 4.45 (t, J=8.5 Hz, 1H), 4.29-4.35 (m, 1H), 4.18 (s, 3H), 3.94 (dd, J=8.5, 5.5 Hz, 1H), 3.80 (dd, J=8.5, 5.0 Hz, 1H), 3.42 (dt, J=13.0, 3.0 Hz, 1H), 2.54 (s, 3H), 2.25 (d, J=12.0 Hz, 1H), 2.07 (d, J=14.5 Hz, 1H), 1.80-1.86 (m, 1H), 1.72-1.77 (m, 1H).

Example 19

Preparation of Compound 83

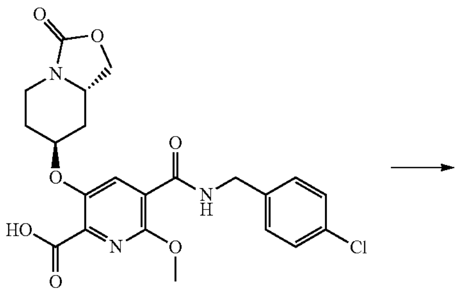

18b

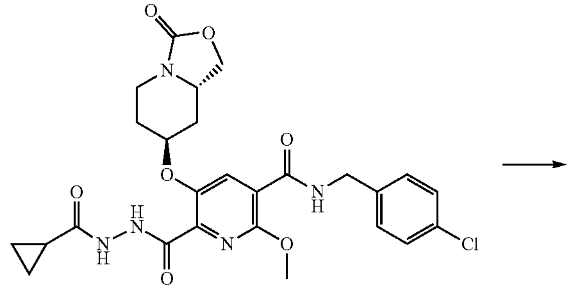

19a

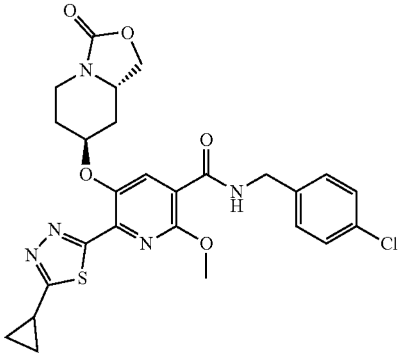

83

Step A—Synthesis of Compound 19a

To a mixture of 18b (154 mg, 0.138 mmol), and cyclopropanecarbohydrazide (19.7 mg, 0.197 mmol) in MeCN (1.19 mL) was added HATU (74.8 mg, 0.197 mmol), and triethylamine (50 μl, 0.36 mmol), and the resulting reaction allowed to stir at room temperature for several hours. The reaction was concentrated in vacuo, and the residue obtained was diluted with water, and extracted with ethyl acetate. The organic extract was washed with brine, dried over $MgSO_4$, filtered, and concentrated in vacuo to provide 19a, which was used without further purification. MS: m/z 558.5=[M+H].

Step B—Synthesis of Compound 83

To a mixture of 19a (46 mg, 0.082 mmol) in THF (1.18 mL) was added 2,4-Bis(4-methoxyphenyl)-2,4-dithioxo-1,3,2,4-dithiadiphosphetane (Lawesson's reagent) (50 mg, 0.12 mmol), and heated at 80° C. under a reflux condenser for 1.5 hours. Additional Lawesson's reagent (40 mg) was added, and heating continued for 6.5 additional hours. The reaction mixture was then concentrated in vacuo, and the residue obtained was purified using preparative HPLC (reverse-phase C-18), eluting with acetonitrile/water+0.1% TFA 10-70% to provide compound 83 as a foam. MS: m/z 556.5=[M+H]. $^1$H NMR (500 MHz, $CDCl_3$, ppm) δ8.35 (s, 1H), 8.34 (t, J=5.5 Hz, 1H), 7.35 (d, J=8.5 Hz, 2H), 7.31 (d, J=8.5 Hz, 2H), 5.07 (s, 1H), 4.66 (d, J=5.5 Hz, 2H), 4.46-4.51 (m, 2H), 4.11 (s, 3H), 3.91-3.95 (m, 1H), 3.77 (dd, J=9.0, 4.5 Hz, 1H), 3.46 (dt, J=8.0, 3.0 Hz, 1H), 2.45-2.50 (m, 1H), 2.30 (d, J=12.5 Hz, 1H), 2.07 (d, J=14.5 Hz, 1H), 1.72-1.83 (m, 2H), 1.23-1.34 (m, 4H).

Example 20

Preparation of Compound 84

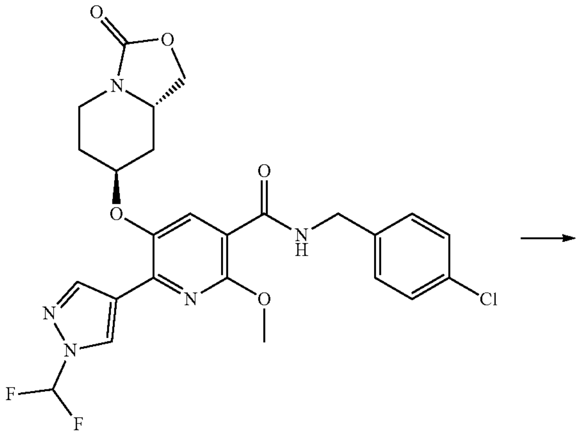

4

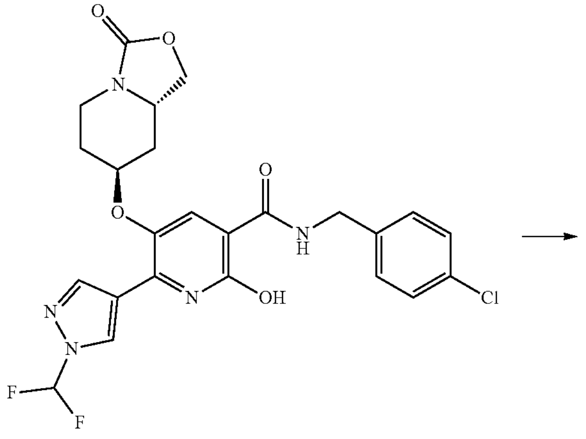

20a

-continued

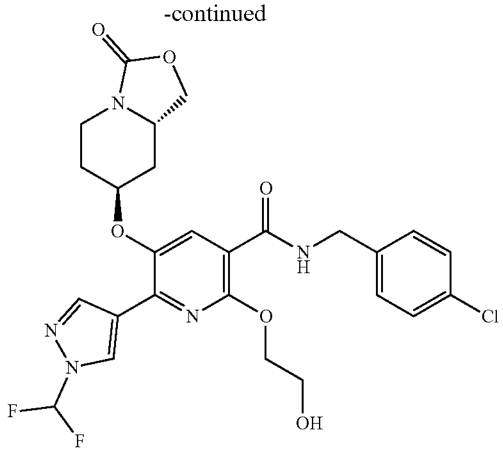

84

Step A—Synthesis of Compound 20a

To a 0° C. solution of 4 (112 mg, 0.204 mmol) in dichloromethane (2 mL) was added $BBr_3$ (1 M in dichloromethane, 0.409 mL), and the resulting reaction was allowed to stir at room temperature for about 15 hours. The reaction was then cooled to 0° C., and quenched with saturated, aqueous $NaHCO_3$, then extracted with 5% methanol in dichloromethane. The organic extract was dried over $Na_2SO_4$, filtered, and concentrated in vacuo to provide 20a as a solid, which was used without further purification. MS: m/z 534.5=[M+H].

Step B—Synthesis of Compound 84

To a mixture of 20a (65 mg, 0.12 mmol) in DMF (1 mL) was added powdered $K_2CO_3$ (50.5 mg, 0.365 mmol), and 2-bromoethan-1-ol (45.6 mg, 0.365 mmol). The resulting reaction was heated to 70° C. and allowed to stir at this temperature for about 15 hours. The reaction mixture was filtered, and the filtrated was concentrated in vacuo. The resulting residue was purified using preparative HPLC (reverse-phase C-18), eluting with acetonitrile/water+0.1% TFA 10-100% to provide compound 84 as a solid. MS: m/z 578.6=[M+H]. $^1H$ NMR (600 MHz, methanol-$d_4$, ppm) δ8.60 (s, 1H), 8.35 (s, 1H), 8.04 (s, 1H), 7.57 (t, J=60.0 Hz, 1H), 7.34 (d, J=8.4 Hz, 2H), 7.29 (d, J=8.4 Hz, 2H), 4.96 (s, 1H), 4.57 (s, 4H), 4.40 (t, J=8.4 Hz, 1H), 4.02 (br s, 1H), 3.89-3.93 (m, 3H), 3.71 (dd, J=13.2, 5.4 Hz, 1H), 3.29 (s, 1H), 3.18-3.22 (m, 1H), 2.26 (d, J=13.8 Hz, 1H), 2.05 (d, J=15.0 Hz, 1H), 1.78-1.84 (m, 1H), 1.72 (t, J=13.2 Hz, 1H).

The following compounds of the present invention were made using the methods described in Example 20 above, and substituting the appropriate reactants and/or reagents:

| Compound | Structure | MS [M + H] |
|---|---|---|
| 85 | 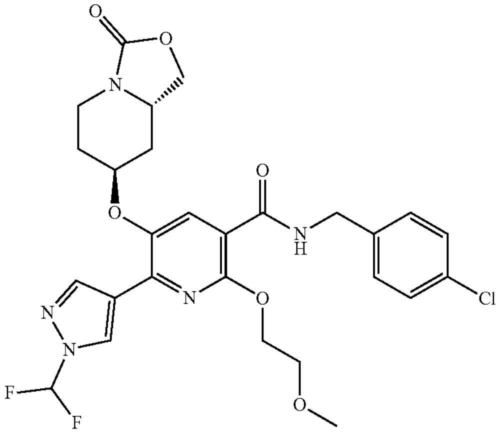 [SMILES: COCCOc1nc(-c2cnn(C(F)F)c2)c(O[C@H]2CCN3C(=O)OC[C@@H]3C2)cc1C(=O)NCc1ccc(Cl)cc1] | 592.6 |
| 86 | 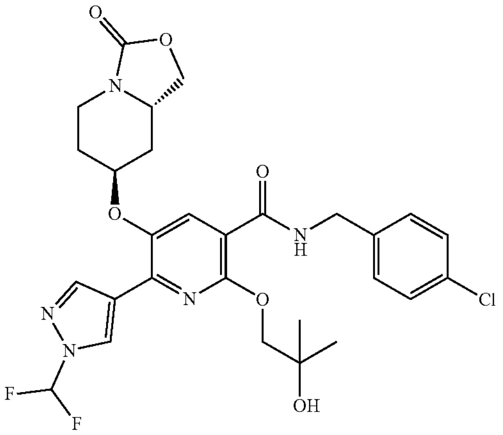 [SMILES: CC(C)(O)COc1nc(-c2cnn(C(F)F)c2)c(O[C@H]2CCN3C(=O)OC[C@@H]3C2)cc1C(=O)NCc1ccc(Cl)cc1] | 606.7 |

-continued
| Compound | Structure | MS [M + H] |
|---|---|---|
| 87 | 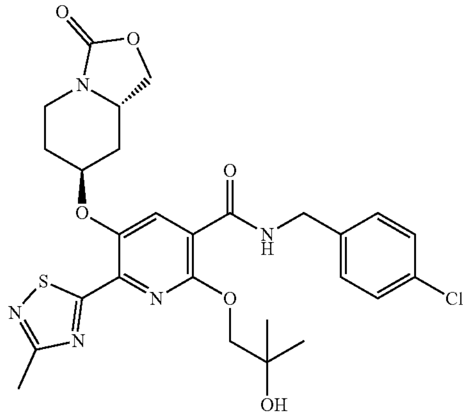 [SMILES: Cc1nsc(-c2nc(OCC(C)(C)O)c(C(=O)NCc3ccc(Cl)cc3)cc2O[C@H]2CCN3C(=O)OC[C@@H]3C2)n1] | 588.6 |
| 88 | 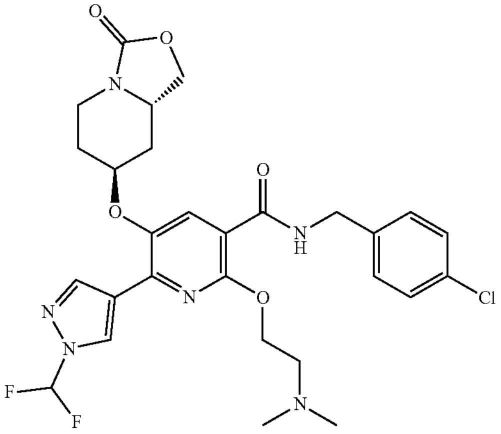 [SMILES: CN(C)CCOc1nc(-c2cnn(C(F)F)c2)c(O[C@H]2CCN3C(=O)OC[C@@H]3C2)cc1C(=O)NCc1ccc(Cl)cc1] | 605.4 |
| 89 | 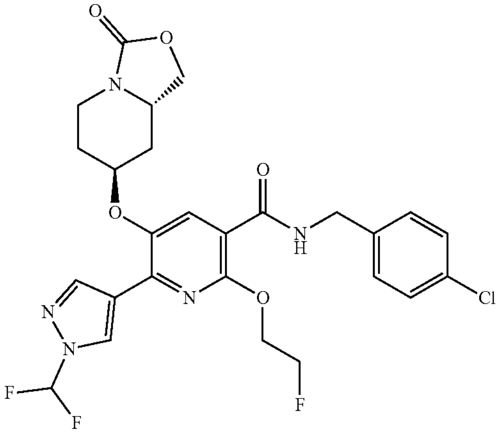 [SMILES: O=C(NCc1ccc(Cl)cc1)c1cc(O[C@H]2CCN3C(=O)OC[C@@H]3C2)c(-c2cnn(C(F)F)c2)nc1OCCF] | 580.3 |

-continued
| Compound | Structure | MS [M + H] |
| --- | --- | --- |
| 90 | 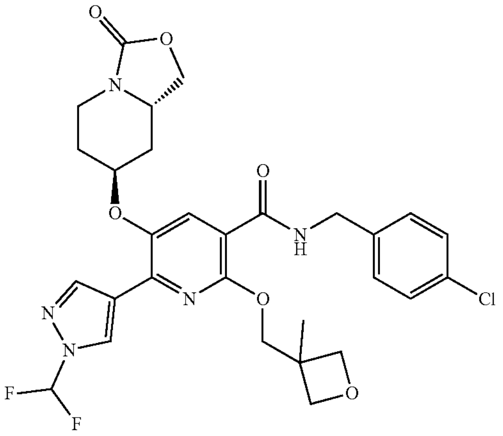 [SMILES: CC1(COc2nc(-c3cnn(C(F)F)c3)c(O[C@H]3CCN4C(=O)OC[C@@H]4C3)cc2C(=O)NCc2ccc(Cl)cc2)COC1] | 618.3 |
| 91 | 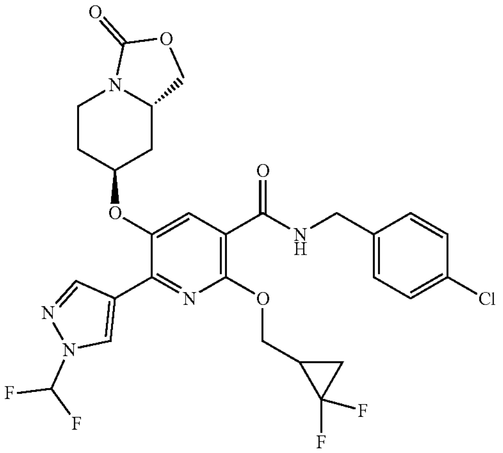 [SMILES: O=C(NCc1ccc(Cl)cc1)c1cc(O[C@H]2CCN3C(=O)OC[C@@H]3C2)c(-c2cnn(C(F)F)c2)nc1OCC1CC1(F)F] | 624.3 |
| 92 | 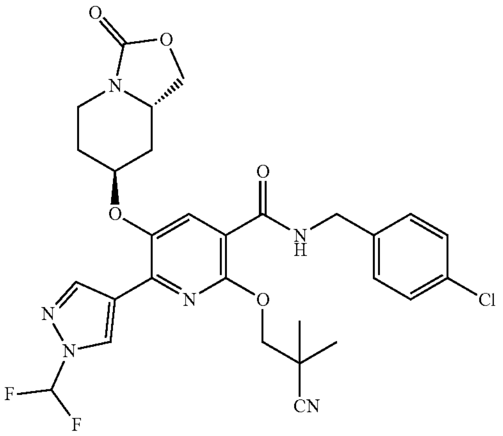 [SMILES: CC(C)(C#N)COc1nc(-c2cnn(C(F)F)c2)c(O[C@H]2CCN3C(=O)OC[C@@H]3C2)cc1C(=O)NCc1ccc(Cl)cc1] | 615.3 |

-continued
| Compound | Structure | MS [M + H] |
|---|---|---|
| 93 | 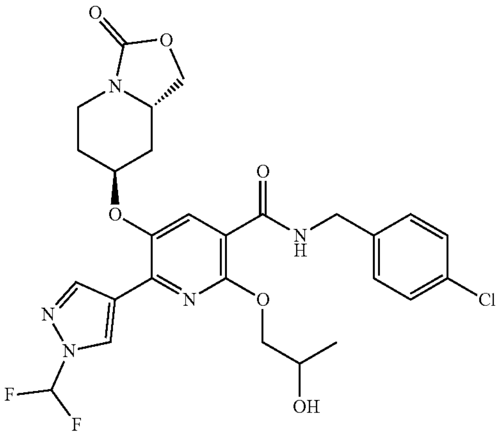 [SMILES: CC(O)COc1nc(-c2cnn(C(F)F)c2)c(O[C@H]2CCN3C(=O)OC[C@@H]3C2)cc1C(=O)NCc1ccc(Cl)cc1] | 592.3 |
| 94 | 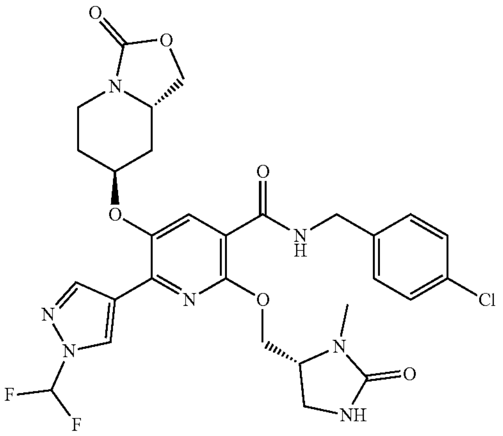 [SMILES: CN1C(=O)NC[C@@H]1COc1nc(-c2cnn(C(F)F)c2)c(O[C@H]2CCN3C(=O)OC[C@@H]3C2)cc1C(=O)NCc1ccc(Cl)cc1] | 646.3 |
| 95 | 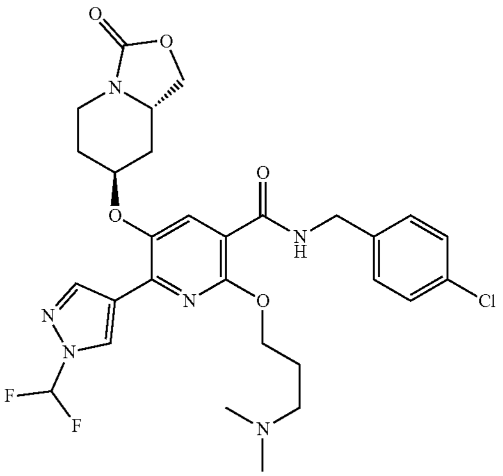 [SMILES: CN(C)CCCOc1nc(-c2cnn(C(F)F)c2)c(O[C@H]2CCN3C(=O)OC[C@@H]3C2)cc1C(=O)NCc1ccc(Cl)cc1] | 619.4 |

-continued
| Compound | Structure | MS [M + H] |
|---|---|---|
| 96 | 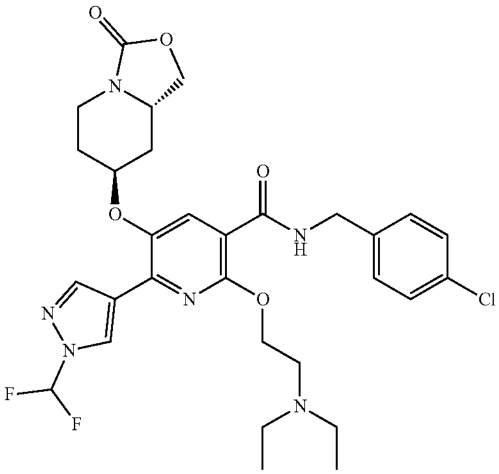 [SMILES: CCN(CC)CCOc1nc(-c2cnn(C(F)F)c2)c(O[C@H]2CCN3C(=O)OC[C@@H]3C2)cc1C(=O)NCc1ccc(Cl)cc1] | 633.4 |
| 97 | 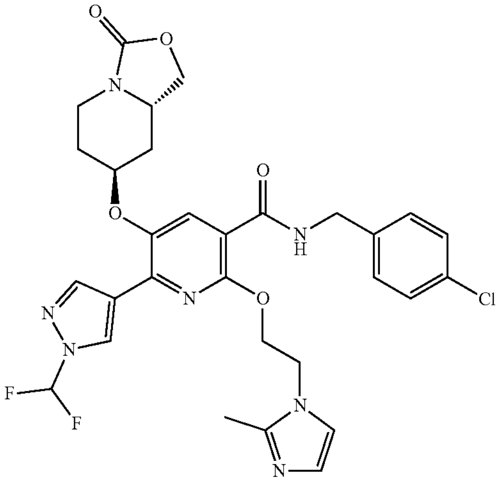 [SMILES: Cc1nccn1CCOc1nc(-c2cnn(C(F)F)c2)c(O[C@H]2CCN3C(=O)OC[C@@H]3C2)cc1C(=O)NCc1ccc(Cl)cc1] | 612.4 |
| 98 | 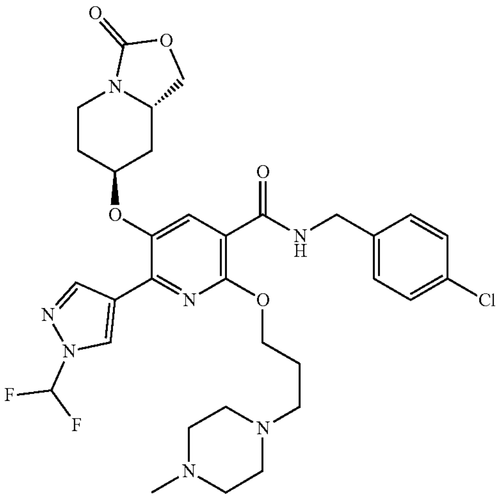 [SMILES: CN1CCN(CCCOc2nc(-c3cnn(C(F)F)c3)c(O[C@H]3CCN4C(=O)OC[C@@H]4C3)cc2C(=O)NCc2ccc(Cl)cc2)CC1] | 674.4 |

-continued
| Compound | Structure | MS [M + H] |
|---|---|---|
| 99 | 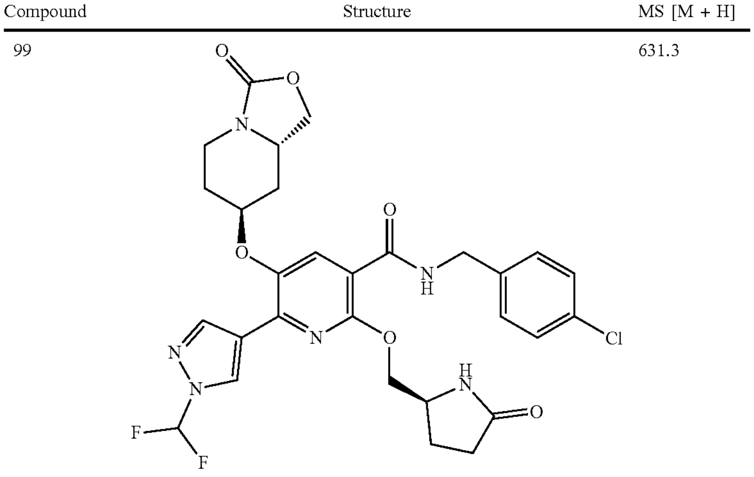 | 631.3 |
| 100 | 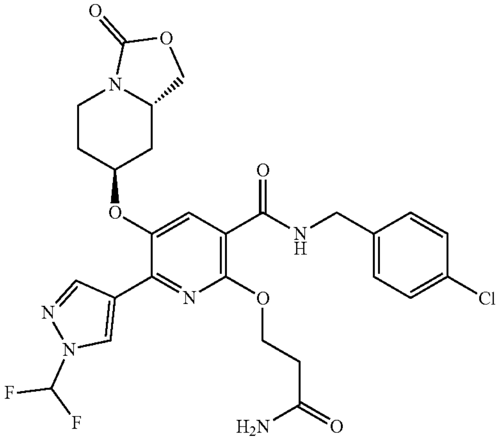 [SMILES: NC(=O)CCOc1nc(-c2cnn(C(F)F)c2)c(O[C@H]2CCN3C(=O)OC[C@@H]3C2)cc1C(=O)NCc1ccc(Cl)cc1] | 605.3 |
Example 21
Preparation of Compound 101
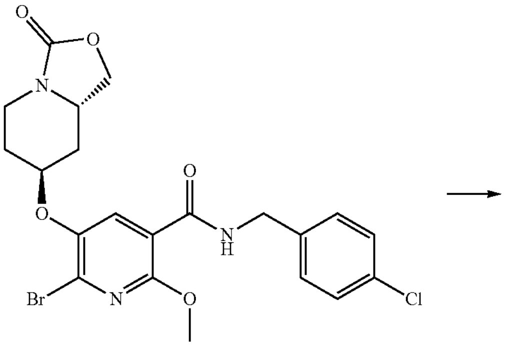
Int-3
-continued
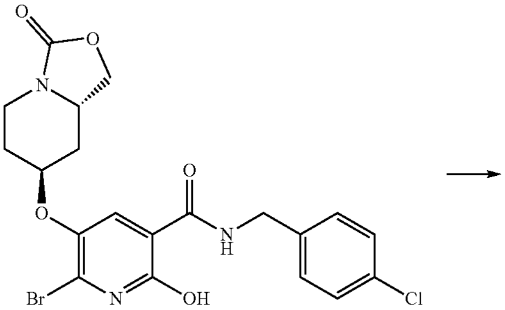
21a -continued

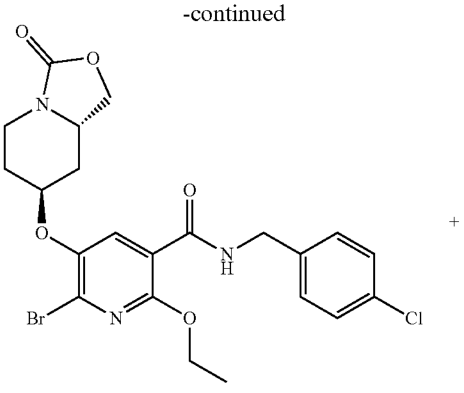

21b

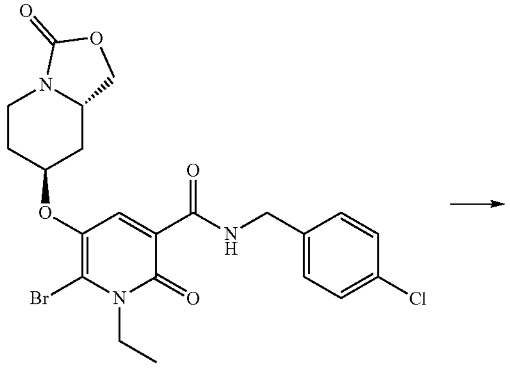

21c

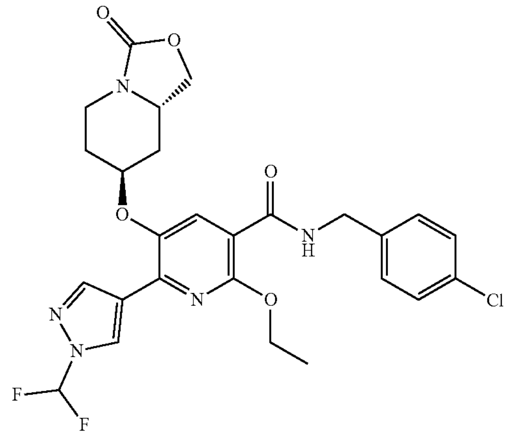

101

Step A—Synthesis of Compound 21a

To a 0° C. solution of Int-3 (56 mg, 0.11 mmol) in dichloromethane (1 mL) was added $BBr_3$ (1 M in dichloromethane, 0.219 mL), and the resulting reaction was allowed to stir at room temperature for about 15 hours. The reaction was quenched with saturated, aqueous $NaHCO_3$, then extracted with 5% methanol in dichloromethane. The organic extract was dried over $Na_2SO_4$, filtered, and concentrated in vacuo to provide 21a as a solid, which was used without further purification. MS: m/z 496.3 and 498.3=[M+H, $^{79}$Br and $^{81}$Br].

Step B—Synthesis of Compound 21b

To a mixture of 21a (43.5 mg, 0.088 mmol), and powdered $K_2CO_3$ (36.3 mg, 0.263 mmol) in DMF (1 mL) was added bromoethane (0.020 mL, 0.263 mmol), and heated at 70° C. for 3 hours. The mixture was filtered, and the crude material was concentrated under a stream of nitrogen for about 15 hours, to provide a mixture of 21b and 21c which was used without further purification. MS: m/z 524.4 and 526.4=[M+H, $^{79}$Br and $^{81}$Br] for both compounds.

Step C—Synthesis of Compound 101

A mixture of 21b and 21c (46 mg, 0.088 mmol), borate 1-(difluoromethyl)-4-(4,4,5,5-tetramethyl-1,3,2-dioxaborolan-2-yl)-1H-pyrazole (21 mg, 0.088 mmol), and 1,1'-bis(di-tert-butylphosphino)ferrocene palladium dichloride (2.86 mg, 4.38 μmol) in dioxane (14 mL) was degassed under nitrogen and then treated with $K_3PO_4$ (1M in water, 0.26 mL). The reaction was further degassed and then sealed and irradiated at 100° C. for 20 minutes. The organic phase was separated and concentrated in vacuo, and the residue obtained was purified using preparative HPLC (reverse-phase C-18), eluting with acetonitrile/water+0.1% TFA 10-100% to provide compound 101 as a solid. MS: m/z 562.5=[M+H]. $^1$H NMR (600 MHz, methanol-$d_4$, ppm) δ8.61 (s, 1H), 8.37 (s, 1H), 8.09 (s, 1H), 7.58 (t, J=60.0 Hz, 1H), 7.36 (d, J=8.4 Hz, 2H), 7.33 (d, J=8.4 Hz, 2H), 5.02 (s, 1H), 4.55-4.60 (m, 4H), 4.43 (t, J=8.4 Hz, 1H), 4.05 (br s, 1H), 3.94-3.97 (m, 1H), 3.73-3.76 (m, 1H), 3.24 (dt, J=13.2, 3.0 Hz, 1H), 2.30 (d, J=12.6 Hz, 1H), 2.09 (d, J=13.8 Hz, 1H), 1.84-1.89 (m, 1H), 1.77 (t, J=12.0 Hz, 1H), 1.39 (q, J=7.2 Hz, 3H).

Example 22

Preparation of Compound 102

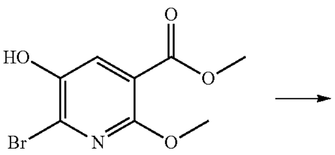

Int-1

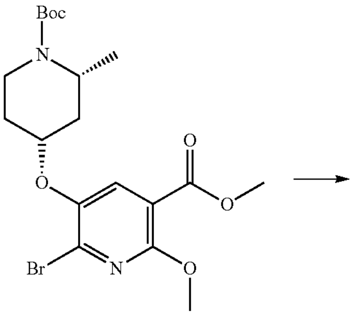

22a

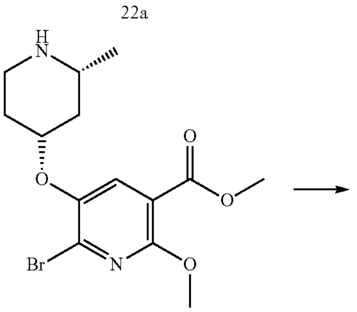

22b

-continued

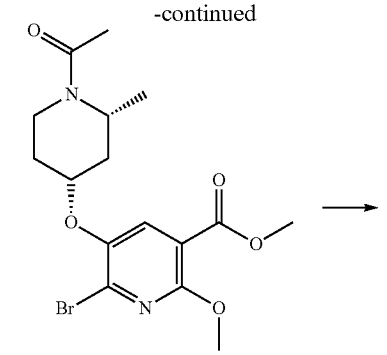

22c

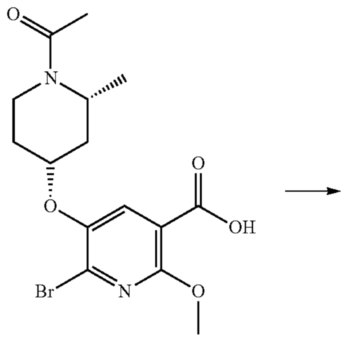

22d

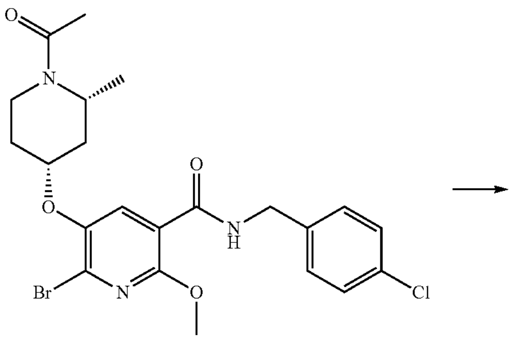

22e

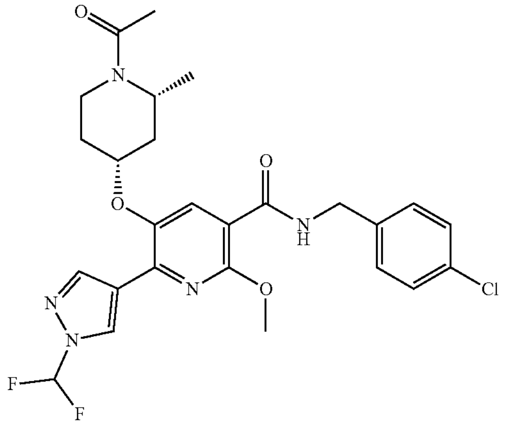

102

Step A—Synthesis of Compound 22a

A solution of triphenylphosphine (550 mg, 2.10 mmol), di-tert-butyl azodicarboxylate (483 mg, 2.099 mmol), tert-butyl (2R,4S)-4-hydroxy-2-methylpiperidine-1-carboxylate (267 mg, 1.24 mmol), and Int-1 (250 mg, 0.954 mmol) in THF (10 mL) was degassed with nitrogen and allowed to stir for about 15 hours at room temperature. The reaction mixture was diluted with water (15 mL) and extracted with ethyl acetate. The organic extract was washed with brine, dried over $Na_2SO_4$, filtered, and concentrated in vacuo, and the resulting residue was purified using silica gel chromatography, eluting with 0-100% EtOAc in hexanes, to provide 22a as an oil. MS: m/z 459.4 and 461.4=[M+H, $^{79}$Br and $^{81}$Br].

Step B—Synthesis of Compound 22b

To a mixture of 22a (220 mg, 0.479 mmol) in THF (3 mL) was added HCl (4 M in dioxane, 0.479 mL), and the resulting reaction was allowed to stir for about 15 hours at room temperature. Additional HCl (0.479 mL) was added, and the reaction was allowed to stir for an additional 48 hours at room temperature. The reaction mixture was concentrated in vacuo to provide 22b, which was used without further purification. MS: m/z 359.3 and 361.3=[M+H, $^{79}$Br and $^{81}$Br].

Step C—Synthesis of Compound 22c

To a mixture of 22b (172 mg, 0.479 mmol) in dichloromethane (4.5 mL) was added acetyl chloride (0.068 ml, 0.96 mmol), and DIEA (0.084 ml, 0.48 mmol), and the resulting reaction was allowed to stir at room temperature for 15 minutes. Additional acetyl chloride (0.034 mL) was added and stirring continued for an additional 15 minutes. The reaction was quenched with water (15 mL) and extracted with 5% methanol in $CH_2Cl_2$. The organic extract was washed sequentially with water and saturated aqueous $NaHCO_3$, dried over $MgSO_4$, filtered and concentrated in vacuo to provide 22c which was used without further purification. MS: m/z 401.3 and 403.3=[M+H, $^{79}$Br and $^{81}$Br].

Step D—Synthesis of Compound 22d

To a mixture of 22c (192 mg, 0.478 mmol) in THF (3.5 mL) was added NaOH (1 M, 1.44 mL), and the resulting reaction was allowed to stir for about 15 hours at room temperature. The reaction was acidified with HCl (6 M, 0.24 mL), and concentrated in vacuo to provide 22d as a solid which was used without further purification. MS: m/z 387.3 and 389.3=[M+H, $^{79}$Br and $^{81}$Br].

Step E—Synthesis of Compound 22e

A solution of 22d (190 mg, 0.491 mmol), HATU (243 mg, 0.638 mmol), and DIEA (0.300 mL, 1.72 mmol) in DMF (3 mL) was allowed to stir at room temperature for 10 minutes, then (4-chlorophenyl)methanamine (104 mg, 0.736 mmol) was added, and the resulting reaction was allowed to stir for about 15 hours at room temperature. The resulting reaction mixture, which contains compound 22e, was used directly in the next step without further isolation or purification. MS: m/z 510.4 and 512.4=[M+H, $^{79}$Br and $^{81}$Br].

Step F—Synthesis of Compound 102

To a mixture of 22e (200 mg, 0.392 mmol, taken directly from Step E) in DMF (2.5 mL) was added borate 1-(difluoromethyl)-4-(4,4,5,5-tetramethyl-1,3,2-dioxaborolan-2-yl)-1H-pyrazole (96 mg, 0.39 mmol), and 1,1'-bis(di-tert-butylphosphino)ferrocene palladium dichloride (13 mg, 0.020 mmol). The reaction mixture was degassed with nitrogen, then diluted with dioxane (2 mL), and degassed under nitrogen again. A solution of $K_3PO_4$ (1 M in water, 1.175 mL) that had previously been degassed under nitrogen was added, and the reaction mixture was sealed and irradiated at 100° C. for 20 minutes. The organic phase was collected, and concentrated in vacuo, and the residue obtained was purified using preparative HPLC (reverse-phase C-18), eluting with acetonitrile/water+0.1% TFA 10-100% to provide compound 102 as a solid. MS: m/z 548.5=[M+H]. $^1H$ NMR (600 MHz, methanol-$d_4$, ppm) δ8.61 (s, 1H), 8.36 (s, 1H), 7.96 (s, 1H), 7.56 (t, J=60.0 Hz, 1H), 7.31 (d, J=8.4 Hz, 2H), 7.27 (d, J=8.4 Hz, 2H), 4.93 (s, 3H), 4.73 (br s, 1H), 4.53-4.59 (m, 3H), 4.05 (s, 3H), 2.08 (s, 3H), 1.85-2.08 (m, 4H), 1.04-1.15 (m, 3H).

Example 23

Preparation of Compound 103

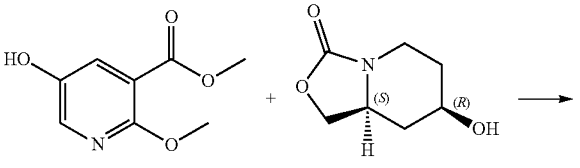

23a Int-2

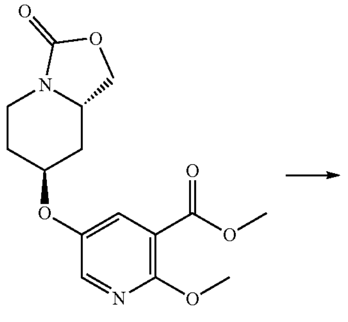

23b

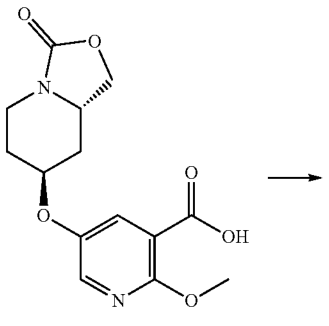

23c

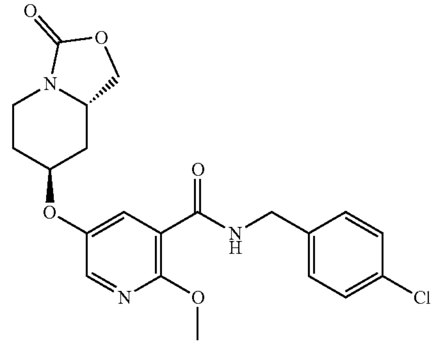

103

Step A—Synthesis of Compound 23b

To a mixture of Int-2 (39 mg, 0.25 mmol), and 23a (45.5 mg, 0.248 mmol) in THF (1654 μL) was added triphenylphosphine (78 mg, 0.30 mmol), and di-tert-butyl azodicarboxylate (68.6 mg, 0.298 mmol), and the resulting reaction was allowed to stir at room temperature for 1 hour. The reaction mixture was concentrated in vacuo, and directly purified using preparative HPLC (reverse-phase C-18), eluting with acetonitrile/water+0.1% TFA 15-95% to provide compound 23b as a solid. MS: m/z 323.1=[M+H].

Step B—Synthesis of Compound 23c

To a mixture of 23b (57 mg, 0.177 mmol) in dioxane (589 μL) was added NaOH (1 M, 354 μL), and water (250 μL), and the resulting reaction was allowed to stir at room temperature for 6 hours. HCl (1 M, 354 μL) was added, and the resulting solution was frozen and dried on a lyophilizer to provide 23c as a solid. MS: m/z 309.1=[M+H].

Step C—Synthesis of Compound 103

To a mixture of 23c (54.5 mg, 0.177 mmol), and triethylamine (61.6 μL, 0.442 mmol) in dichloromethane (1768 μL) was added (4-chlorophenyl)methanamine (25.8 μL, 0.212 mmol) followed by 2,4,6-tripropyl-1,3,5,2,4,6-trioxatriphosphinane 2,4,6-trioxide (T3P) (50 wt % in EtOAc, 132 μL, 0.221 mmol). The resulting reaction was allowed to stir at room temperature, for 1 hour, then additional T3P (40 μL) was added, and the reaction was allowed to stir for an additional 30 minutes. The reaction mixture was concentrated in vacuo, and the resulting residue was purified using silica gel chromatography, eluting with 25-50% (3:1 EtOAc:EtOH) in hexanes to provide compound 103 as a solid. MS: m/z 432.1=[M+H]. $^1H$ NMR (500 MHz, $CDCl_3$, ppm) δ8.37 (t, J=6.0 Hz, 1H), 8.17 (d, J=3.0 Hz, 1H), 7.99 (d, J=3.0 Hz, 1H), 7.33 (d, J=8.5 Hz, 2H), 7.29 (d, J=8.5 Hz, 2H), 4.79 (s, 1H), 4.64 (d, J=6.0 Hz, 2H), 4.44 (t, J=8.5 Hz, 1H), 4.12-4.18 (m, 1H), 4.05 (s, 3H), 3.92 (dd, J=8.5, 5.5 Hz, 1H), 3.81 (dd, J=13.5, 5.5 Hz, 1H), 3.31 (dt, J=13.5, 3.5 Hz, 1H), 2.20 (d, J=13.5 Hz, 1H), 2.04 (d, J=15 Hz, 1H), 1.73-1.80 (m, 1H), 1.64-1.19 (m, 1H).

Example 24

CMV and VZV Polymerase Assays

Human cytomegalovirus and varicella zoster virus DNA polymerases were expressed via baculovirus vector in SF21 cells and purified. Heterodimeric nucleic acid substrate used in the herpesvirus polymerase reactions was generated by annealing a 59-mer template to a 17-mer digoxigenin-labeled primer. Polymerase (HCMV final concentration of 0.2 nM; VZV final concentration of 0.4 nM) was combined with an inhibitor compound or DMSO in assay buffer (10 mM HEPES, pH 7.5, 25 mM KCl, 25 mM NaCl, 5 mM $MgCl_2$, 5% glycerol, 0.67 mg/ml bovine serum albumin, and 1 mM tris(2-carboxyethyl)phosphine), and this mixture was pre-incubated for 30 minutes at room temperature in 384-well microtiter plates. The polymerization reaction was initiated by the addition of template/primer substrate (final concentration: 1.6 nM), and dNTPs (final concentration: 24 nM dCTP, 24 nMdGTP, 16 nM dATP, 16 nM dTTP, and 0.8 nM biotin-dUTP). After 60 min incubation at 37° C., reactions were terminated with quench buffer (25 mM HEPES pH 7.5, 100 mM NaCl, 0.25% Tween-20, 12 mM EDTA, and 1 mg/ml bovine serum albumin). Incorporation of biotinylated UTP was detected with 2.5-5 ug/ml anti-DIG AlphaLISA acceptor beads and 5-10 ug/ml streptavidin AlphaLISA donor beads (PerkinElmer). Compound effects were normalized to the window defined by the controls (DMSO only and pre-quenched wells) and were fit using a 4-parameter algorithm to report an $IC_{50}$.

Example 25

Viral qPCR Assays

Viral qPCR Assays (V0/V1)

MRC5 cells, Vero cells, and MeWo cells were obtained from ATCC, and were maintained at 37° C./5% CO2/90% relative humidity in Minimal Essential Medium with 10% fetal bovine serum, 2.0 nM L-glutamine, 100 units/ml penicillin and 100 ug/ml streptomycin. Assay plates were prepared by dispensing compounds dissolved in DMSO into wells of 384 well collagen-coated plates using an ECHO acoustic dispenser. Each compound was tested in a 10-point, serial 3-fold dilution. Controls included uninfected cells and infected cells treated only with DMSO. Assays were initiated by mixing selected cells, in suspension, with virus, and dispensing 50 μl/well infected cells to pre-plated compounds. Plates were incubated at 37° C./5% CO2/90% relative humidity for ~72 hrs to permit genomic replication, and infected cells were lysed by the addition of an equal volume of lysis buffer (10 mM Tris-HCl, pH8, 50 mM KCl, 2 mM $MgCl_2$, 0.45% NP-40, 0.45% Tween-20, and 100 μg/ml proteinase K). An aliquot of the lysate was transferred to a 384-well PCR plate and incubated at 56° C. for 1 hour and then at 95° C. for 10 min. Levels of a viral gene and of the cellular control, PPIA (Thermo Fisher Assay ID=Hs04194521_s1), were measured in separate 10 ul qPCR assays using TaqMan® Gene Expression Master Mix (Applied Biosystems), and an 7900HT Fast Real-Time PCR System with 384-Well Block Module. 7-point, serial 10-fold dilutions of a plasmid standard were run on each plate to generate a standard curve, and genome copies numbers were calculated by plotting experimental Ct onto linear regression of the standard curve. Viral genome copy numbers were normalized by cellular control copy number, and compound effects were normalized to the window defined by the controls. Calculated % effects were fit using a 4-parameter algorithm, and $EC_{50}$ was reported.

Viral qPCR Assays (V2/V3)

MRC5 cells, Vero cells, and MeWo cells were obtained from ATCC, and were maintained at 37° C./5% CO2/90% relative humidity in Minimal Essential Medium with 10% fetal bovine serum, 2.0 nM L-glutamine, 100 units/ml penicillin and 100 ug/ml streptomycin. Assay plates were prepared by dispensing compounds dissolved in DMSO into wells of 384 well collagen-coated plates using an ECHO acoustic dispenser. Each compound was tested in a 10-point, serial 3-fold dilution. Controls included uninfected cells and infected cells treated only with DMSO. Assays were initiated by mixing selected cells, in suspension, with virus, and dispensing 50 μl/well infected cells to pre-plated compounds. Plates were incubated at 37° C./5% CO2/90% relative humidity for ~72 hrs to permit genomic replication, and infected cells were lysed by the addition of an equal volume of lysis buffer (10 mM Tris-HCl, pH 8, 50 mM KCl, 2 mM $MgCl_2$, 0.45% NP-40, 0.45% Tween-20, and 100 μg/ml proteinase K). An aliquot of the lysate was transferred to a 384-well PCR plate and incubated at 56° C. for 1 hour and then at 95° C. for 10 min. Levels of a viral gene were measured in 10 ul qPCR assays using TaqMan® Gene Expression Master Mix (Applied Biosystems), and an 7900HT Fast Real-Time PCR System with 384-Well Block Module. 7-point, serial 10-fold dilutions of a plasmid standard were run on each plate to generate a standard curve, and genome copies numbers were calculated by plotting experimental Ct onto linear regression of the standard curve. Compound effects on viral genome copy number were normalized to the window defined by the controls. Calculated % effects were fit using a 4-parameter algorithm, and $EC_{50}$ was reported.

HCMV: Strain AD169 Street was assayed in MRC-5 cells and was used at 0.05-0.1 pfu/cell. The assays were performed in either growth media or in the same media with 50% fetal bovine serum. Primer-probe set was Thermo Fisher Assay ID=AIFATFK.

VZV: Strain Street was maintained as an infected cell stock in MRC-5 cells. It was assayed in MeWo or MRC5 cells and was used at 0.04-0.1 pfu/cell. The assays were performed in growth medium. Primer-probe set was Thermo Fisher Assay ID=AIPAEXQ.

HSV-1: Strain F Street was assayed in Vero or MRC5 cells and was used at 0.0005-0.004 pfu/cell in growth medium. Primer-probe set was Thermo Fisher Assay ID=AIBJZIB Illustrative compounds of the present invention were tested in one or more of the above assays and results are provided in the table below:

| Compound | CMV[a] ($IC_{50}$) | VZV[a] ($IC_{50}$) | CMV Cell[b] ($EC_{50}$) | VZV Cell[b] ($EC_{50}$) | HSV1 Cell[b] ($EC_{50}$) |
|---|---|---|---|---|---|
| Int-3 | 55.9 nM | 21.3 nM | 822 nM | 651 nM | 832 nM |
| 4 | 7.52 nM | 0.715 nM | 146 nM | 141 nM | 105 nM |
| 5 | 4.11 nM | 0.161 nM | 71.4 nM | 107 nM | 80.1 nM |
| 6 | 1.05 nM | 0.0674 nM | 77 nM | 110 nM | 87.5 nM |
| 7 | 1.32 nM | 0.223 nM | 82.6 nM | 129 nM | 72.6 nM |
| 8 | 37.9 nM | 15 nM | 415 nM | 841 nM | 866 nM |
| 9 | 4.87 nM | 1.71 nM | 111 nM | 98.4 nM | 85.7 nM |
| 10 | 11.3 nM | 0.508 nM | 134 nM | 131 nM | 150 nM |
| 11 | 20.3 nM | N/A | 653 nM | 1270 nM | 456 nM |
| 12 | 9.27 nM | N/A | 313 nM | 235 nM | 187 nM |
| 13 | 16.2 nM | N/A | 457 nM | 307 nM | 229 nM |
| 14 | 19.2 nM | N/A | 1020 nM | 2570 nM | 824 nM |
| 15 | 12 nM | 12.9 nM | 144 nM | 355 nM | 233 nM |
| 16 | 2.07 nM | 0.63 nM | 137 nM | N/A | N/A |
| 17 | 10.7 nM | N/A | 317 nM | 244 nM | 186 nM |
| 18 | 19.6 nM | N/A | 1200 nM | N/A | N/A |
| 19 | 5.55 nM | 2.91 nM | 157 nM | 204 nM | 96.9 nM |
| 20 | 25.3 nM | N/A | 587 nM | 1870 nM | 1440 nM |
| 21 | 20.9 nM | N/A | 500 nM | 417 nM | 377 nM |
| 22 | 3.69 nM | 4.84 nM | 170 nM | 129 nM | 93 nM |
| 23 | 18 nM | N/A | 140 nM | 117 nM | 87.4 nM |
| 24 | 7.58 nM | 4.03 nM | 200 nM | 390 nM | 195 nM |
| 25 | 6.77 nM | N/A | 159 nM | 186 nM | 146 nM |
| 26 | 5.8 nM | N/A | 372 nM | 208 nM | 174 nM |
| 27 | 33.6 nM | N/A | 556 nM | 859 nM | 648 nM |
| 28 | 5.36 nM | N/A | 200 nM | 196 nM | 103 nM |
| 29 | 31.2 nM | N/A | 514 nM | 368 nM | 246 nM |
| 30 | 14.5 nM | N/A | 462 nM | 187 nM | 202 nM |
| 31 | 5.13 nM | N/A | 175 nM | 102 nM | 103 nM |
| 32 | 0.705 nM | N/A | 103 nM | 106 nM | 52 nM |
| 33 | 11 nM | N/A | 901 nM | 679 nM | 144 nM |
| 34 | 8.26 nM | N/A | 421 nM | 1920 nM | 260 nM |
| 35 | 79.5 nM | N/A | 1940 nM | N/A | N/A |
| 36 | 3.38 nM | N/A | 175 nM | 92.3 nM | 82 nM |
| 37 | 8.81 nM | 8.24 nM | 180 nM | 178 nM | 144 nM |
| 38 | 9.81 nM | 5.86 nM | 111 nM | 150 nM | 83.1 nM |
| 39 | 81.5 nM | N/A | 886 nM | 1360 nM | 658 nM |
| 40 | 15.9 nM | 10.2 nM | 206 nM | 200 nM | 123 nM |
| 41 | 17 nM | N/A | 606 nM | 418 nM | 494 nM |
| 42 | 10.4 nM | N/A | 194 nM | 130 nM | 79.8 nM |
| 43 | 22.3 nM | N/A | 422 nM | 298 nM | 169 nM |
| 44 | 20 nM | N/A | 326 nM | 585 nM | 263 nM |
| 45 | 2.3 nM | N/A | 111 nM | 141 nM | 50 nM |
| 46 | 4.69 nM | 1.53 nM | 165 nM | 121 nM | 51.6 nM |
| 47 | 4.87 nM | N/A | 1300 nM | 2320 nM | 654 nM |
| 48 | 192.7 nM | N/A | 2007 nM | N/A | N/A |
| 49 | 131 nM | N/A | 2740 nM | N/A | N/A |
| 50 | 80.7 nM | N/A | 2760 nM | N/A | N/A |
| 51 | 133 nM | N/A | 3340 nM | N/A | N/A |
| 52 | 120 nM | N/A | 3480 nM | N/A | N/A |
| 53 | 164 nM | N/A | 3990 nM | N/A | N/A |
| 54 | 23.7 nM | N/A | 5260 nM | N/A | N/A |

-continued

| Compound | CMV[a] ($IC_{50}$) | VZV[a] ($IC_{50}$) | CMV Cell[b] ($EC_{50}$) | VZV Cell[b] ($EC_{50}$) | HSV1 Cell[b] ($EC_{50}$) |
|---|---|---|---|---|---|
| 55 | 3.16 nM | 5.38 nM | 161 nM | 178 nM | 102 nM |
| 56 | 2.08 nM | 6.48 nM | 102 nM | 123 nM | 36.3 nM |
| 57 | 6.13 nM | N/A | 538 nM | 364 nM | 207 nM |
| 58 | 2.95 nM | 0.259 nM | 59.3 nM | 103 nM | 63.4 nM |
| 59 | 3.25 nM | N/A | 324 nM | 160 nM | 80.6 nM |
| 60 | 6.32 nM | 0.351 nM | 29.8 nM | 90.4 nM | 65 nM |
| 61 | 1.44 nM | 0.0412 nM | 60.1 nM | 70.8 nM | 49 nM |
| 62 | 4.3 nM | 0.252 nM | 73 nM | 157 nM | 129 nM |
| 63 | 8.74 nM | N/A | 164 nM | 167 nM | 148 nM |
| 64 | 69.3 nM | N/A | 911 nM | 1560 nM | 597 nM |
| 65 | 16.4 nM | 5.28 nM | 376 nM | 758 nM | 877 nM |
| 66 | 5.23 nM | N/A | 146 nM | 648 nM | 262 nM |
| 67 | 22.9 nM | N/A | 368 nM | 2270 nM | 568 nM |
| 68 | 28.7 nM | N/A | 265 nM | 661 nM | 654 nM |
| 69 | 53.9 nM | N/A | 1480 nM | N/A | N/A |
| 70 | 15 nM | 14.5 nM | 194 nM | 409 nM | 278 nM |
| 71 | 22.8 nM | 3.54 nM | 221 nM | 468 nM | 396 nM |
| 72 | 45.5 nM | 12.4 nM | 276 nM | 665 nM | 559 nM |
| 73 | 20.9 nM | N/A | 339 nM | 828 nM | 575 nM |
| 74 | 31.6 nM | N/A | 356 nM | 709 nM | 271 nM |
| 75 | 18 nM | N/A | 380 nM | 657 nM | 420 nM |
| 76 | 32.1 nM | N/A | 519 nM | 778 nM | 293 nM |
| 77 | 31.5 nM | N/A | 872 nM | N/A | N/A |
| 78 | 49 nM | N/A | 616 nM | 1850 nM | 644 nM |
| 79 | 28.7 nM | N/A | 337 nM | 463 nM | 518 nM |
| 80 | 98.9 nM | N/A | 3210 nM | N/A | N/A |
| 81 | 88.6 nM | N/A | 558 nM | 3650 nM | 2880 nM |
| 82 | 8.36 nM | 0.0532 nM | 83.5 nM | 103 nM | 73.9 nM |
| 83 | 11.7 nM | 6.05 nM | 153 nM | 110 nM | 83.5 nM |
| 84 | 3.33 nM | 0.627 nM | 116 nM | 140 nM | 113 nM |
| 85 | 15.6 nM | 1.47 nM | 187 nM | 342 nM | 143 nM |
| 86 | 8.84 nM | 2.96 nM | 213 nM | 232 nM | 130 nM |
| 87 | 5.13 nM | N/A | 108 nM | 207 nM | 140 nM |
| 88 | 3.16 nM | N/A | 32.5 nM | 317 nM | 257 nM |
| 89 | 12.1 nM | N/A | 195 nM | 246 nM | 203 nM |
| 90 | 9.83 nM | N/A | 131 nM | 286 nM | 180 nM |
| 91 | 18.5 nM | N/A | 271 nM | 569 nM | 346 nM |
| 92 | 7.31 nM | N/A | 137 nM | 417 nM | 229 nM |
| 93 | 4.62 nM | N/A | 204 nM | 250 nM | 59.1 nM |
| 94 | 5.15 nM | N/A | 520 nM | 2180 nM | 773 nM |
| 95 | 1.46 nM | N/A | 151 nM | 463 nM | 141 nM |
| 96 | 2.72 nM | N/A | 75.9 nM | 400 nM | 148 nM |
| 97 | 6.9 nM | N/A | 394 nM | 1570 nM | 663 nM |
| 98 | 14.1 nM | N/A | 115 nM | 617 nM | 290 nM |
| 99 | 4.67 nM | N/A | 282 nM | 1310 nM | 493 nM |
| 100 | 3.17 nM | N/A | 47.4 nM | 451 nM | 213 nM |
| 101 | 42.6 nM | N/A | 524 nM | 578 nM | 320 nM |
| 102 | 14.5 nM | N/A | 344 nM | 887 nM | 601 nM |
| 103 | 249 nM | 110 nM | 4690 nM | 5500 nM | N/A |

N/A = not available
[a]data generated using the assay described in Example 24
[b]data generated using the assay described in Example 25

Uses of the Amido-Substituted Pyridyl Compounds

The Amido-Substituted Pyridyl Compounds are useful in human and veterinary medicine for treating or preventing a viral infection in a patient. In one embodiment, the Amido-Substituted Pyridyl Compounds can be inhibitors of viral replication. In another embodiment, the Amido-Substituted Pyridyl Compounds can be inhibitors of herpesvirus replication. Accordingly, the Amido-Substituted Pyridyl Compounds are useful for treating viral infections, such as herpesvirus. In accordance with the invention, the Amido-Substituted Pyridyl Compounds can be administered to a patient in need of treatment or prevention of a viral infection.

Accordingly, in one embodiment, the invention provides methods for treating or preventing a viral infection in a patient comprising administering to the patient an effective amount of at least one Amido-Substituted Pyridyl Compound or a pharmaceutically acceptable salt thereof.

Treatment or Prevention of Herpesvirus Infection

The Amido-Substituted Pyridyl Compounds are useful in the inhibition of herpesvirus replication, the treatment of herpesvirus infection and/or reduction of the likelihood or severity of symptoms of herpesvirus infection and the inhibition of herpesvirus viral replication and/or herpesvirus viral production in a cell-based system. For example, the Amido-Substituted Pyridyl Compounds are useful in treating infection by herpesvirus after suspected past exposure to herpesvirus by such means as blood transfusion, exchange of body fluids, bites, accidental needle stick, or exposure to patient blood during surgery or other medical procedures. Accordingly, in one embodiment, the invention provides a method for treating herpesvirus infection in a patient, the method comprising administering to the patient an effective amount of at least one Amido-Substituted Pyridyl Compound or a pharmaceutically acceptable salt thereof.

In one embodiment, the herpesvirus being treated or prevented is of the family α-herpesviridae. Herpesviruses of the family α-herpesviridae include, but are not limited to, herpes simplex virus 1 (HSV-1), herpes simplex 2 (HSV-2), and varicella zoster virus (VZV).

In another embodiment, the herpesvirus being treated or prevented is of the family β-herpesviridae. Herpesviruses of the family β-herpesviridae include, but are not limited to, human cytomegalovirus (CMV), human herpesvirus 6 (HHV6), and human herpesvirus 7 (HHV7).

In another embodiment, the herpesvirus being treated or prevented is of the family γ-herpesviridae. Herpesviruses of the family γ-herpesviridae include, but are not limited to, Epstein-Barr virus (EBV), human herpesvirus 4 (HHV4), and Kaposi's sarcoma-associated herpesvirus (KHSV), also known as human herpesvirus 8 (HHV8).

In one embodiment, the herpesvirus being treated or prevented is HSV-1.

In another embodiment, the herpesvirus being treated or prevented is HSV-2.

In another embodiment, the herpesvirus being treated or prevented is VZV.

In still another embodiment, the herpesvirus being treated or prevented is CMV.

In another embodiment, the herpesvirus being treated or prevented is HHV6.

In yet another embodiment, the herpesvirus being treated or prevented is HHV7.

In another embodiment, the herpesvirus being treated or prevented is EBV.

In a further embodiment, the herpesvirus being treated or prevented is HHV4.

In another embodiment, the herpesvirus being treated or prevented is KSHV.

In a specific embodiment, the amount administered is effective to treat or prevent infection by herpesvirus in the patient. In another specific embodiment, the amount administered is effective to inhibit herpesvirus viral replication and/or viral production in the patient.

The Amido-Substituted Pyridyl Compounds are also useful in the preparation and execution of screening assays for antiviral compounds. Furthermore, the Amido-Substituted Pyridyl Compounds are useful in establishing or determining the binding site of other antivirals to the herpesvirus polymerase.

The compositions and combinations of the present invention can be useful for treating a patient suffering from infection related to any herpesvirus infection. Herpesvirus types may differ in their antigenicity, level of viremia, severity of disease produced, and response to therapy. See Poole et al., Clinical Therapeutics, 40:8 (2018), 1282-1298.

Combination Therapy

In another embodiment, the present methods for treating or preventing herpesvirus infection can further comprise the administration of one or more additional therapeutic agents which are not Amido-Substituted Pyridyl Compounds.

In one embodiment, the additional therapeutic agent is an antiviral agent. In another embodiment, the additional therapeutic agent is an anti-herpes agent.

Anti-herpes agents useful in the present compositions and methods include, but are not limited to, nucleoside polymerase inhibitors, such as acyclovir, valaciclovir, famciclovir, penciclovir, cidofovir, brincidofovir (CMX-001), valmanciclovir, ganciclovir, valganciclovir, and N-methanocarbathymidine (N-MCT); pyrophosphate polymerase inhibitors, such as foscarnet; CMV terminase inhibitors, such as letermovir; viral kinase inhibitors, such as maribavir; and helicase-primase inhibitors, such as pritelivir (AIC-316), and amenamevir (ASP-2151).

In another embodiment, the additional therapeutic agent is an immunomodulatory agent, such as an immunosuppressive agent. Immunosuppressant agents useful in the present compositions and methods include, but are not limited to, cytotoxic agents, such as cyclophosphamide and cyclosporin A; corticosteroids, such as hydrocortisone and dexamethasone, and non-steroidal anti-inflammatory agents (NSAID).

Accordingly, in one embodiment, the present invention provides methods for treating a herpesvirus infection in a patient, the method comprising administering to the patient: (i) at least one Amido-Substituted Pyridyl Compound, or a pharmaceutically acceptable salt thereof, and (ii) at least one additional therapeutic agent that is other than an Amido-Substituted Pyridyl Compound, wherein the amounts administered are together effective to treat or prevent the herpesvirus infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, an Amido-Substituted Pyridyl Compound and an additional therapeutic agent may be present in fixed amounts (dosage amounts) in a single dosage unit (e.g., a capsule, a tablet and the like).

In one embodiment, the at least one Amido-Substituted Pyridyl Compound is administered during a time when the additional therapeutic agent(s) exert their prophylactic or therapeutic effect, or vice versa.

In another embodiment, the at least one Amido-Substituted Pyridyl Compound and the additional therapeutic agent(s) are administered in doses commonly employed when such agents are used as monotherapy for treating a herpesvirus infection.

In another embodiment, the at least one Amido-Substituted Pyridyl Compound and the additional therapeutic agent(s) are administered in doses lower than the doses commonly employed when such agents are used as monotherapy for treating a herpesvirus infection.

In still another embodiment, the at least one Amido-Substituted Pyridyl Compound and the additional therapeutic agent(s) act synergistically and are administered in doses lower than the doses commonly employed when such agents are used as monotherapy for treating a herpesvirus infection.

In one embodiment, the at least one Amido-Substituted Pyridyl Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

The at least one Amido-Substituted Pyridyl Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Amido-Substituted Pyridyl Compound and the additional therapeutic agent(s) may inhibit the resistance of a herpesvirus infection to these agents.

The doses and dosage regimen of the other agents used in the combination therapies of the present invention for the treatment or prevention of herpesvirus infection can be determined by the attending clinician, taking into consideration the approved doses and dosage regimen in the package insert; the age, sex and general health of the patient; and the type and severity of the viral infection or related disease or disorder. When administered in combination, the Amido-Substituted Pyridyl Compound(s), and the other agent(s) can be administered simultaneously (i.e., in the same composition or in separate compositions one right after the other) or sequentially. This is particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

In one embodiment, one or more compounds of the present invention are administered with one or more additional therapeutic agents selected from: an immunomodulator, an anti-herpes agent, a viral replication inhibitor, an antisense agent, a therapeutic vaccine, a virion production inhibitor, a viral entry inhibitor, a viral assembly inhibitor, an antibody therapy (monoclonal or polyclonal), and any agent useful for treating any type of herpesvirus infection.

Compositions and Administration

Due to their activity, the Amido-Substituted Pyridyl Compounds are useful in veterinary and human medicine. As described above, the Amido-Substituted Pyridyl Compounds are useful for treating or preventing herpesvirus infection in a patient in need thereof.

Accordingly, in one embodiment, the present invention provides pharmaceutical compositions comprising an effective amount of a compound of formula (I), or a pharmaceutically acceptable salt thereof, and a pharmaceutically acceptable carrier.

In another embodiment, the present invention provides pharmaceutical compositions comprising (i) an effective amount of a compound of formula (I), or a pharmaceutically acceptable salt thereof, and a pharmaceutically acceptable carrier; and (ii) one or more additional therapeutic agents, wherein said additional therapeutic agents are selected from anti-herpes agents and immunomodulators.

When administered to a patient, the Amido-Substituted Pyridyl Compounds can be administered as a component of a composition that comprises a pharmaceutically acceptable carrier or vehicle. The present invention provides pharmaceutical compositions comprising an effective amount of at least one Amido-Substituted Pyridyl Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms), and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral or intravenous injection.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate-controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Amido-Substituted Pyridyl Compounds are administered orally.

In another embodiment, the one or more Amido-Substituted Pyridyl Compounds are administered intravenously.

In still another embodiment, the one or more Amido-Substituted Pyridyl Compounds are administered sublingually.

In one embodiment, a pharmaceutical preparation comprising at least one Amido-Substituted Pyridyl Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Amido-Substituted Pyridyl Compound(s) by weight or volume. In various embodiments, the present compositions can contain, in one embodiment, from about 1% to about 70% or from about 5% to about 60% of the Amido-Substituted Pyridyl Compound (s) by weight or volume.

The amount and frequency of administration of the Amido-Substituted Pyridyl Compounds will be regulated according to the judgment of the attending clinician considering such factors as age, condition and size of the patient as well as severity of the symptoms being treated. Generally, a total daily dosage of the at least one Amido-Substituted Pyridyl Compound(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Amido-Substituted Pyridyl Compound or a pharmaceutically acceptable salt thereof; (ii) one or more additional therapeutic agents that are not an Amido-Substituted Pyridyl Compound; and (iii) a pharmaceutically acceptable carrier, wherein the amounts in the composition are together effective to treat herpesvirus infection.

In one embodiment, the present invention provides compositions comprising a Compound of Formula (I), and a pharmaceutically acceptable carrier.

In another embodiment, the present invention provides compositions comprising a Compound of Formula (I), a pharmaceutically acceptable carrier, and a second therapeutic agent selected from the group consisting of anti-herpes agents and immunomodulators.

In another embodiment, the present invention provides compositions comprising a Compound of Formula (I), a pharmaceutically acceptable carrier, and two additional therapeutic agents, each of which are independently selected from the group consisting of anti-herpes agents and immunomodulators.

Kits

In one aspect, the present invention provides a kit comprising a therapeutically effective amount of at least one Amido-Substituted Pyridyl Compound, or a pharmaceutically acceptable salt, solvate, ester or prodrug of said compound and a pharmaceutically acceptable carrier, vehicle or diluent.

In another aspect the present invention provides a kit comprising an amount of at least one Amido-Substituted Pyridyl Compound, or a pharmaceutically acceptable salt, solvate, ester or prodrug of said compound and an amount of at least one additional therapeutic agent listed above, wherein the amounts of the two or more active ingredients result in a desired therapeutic effect. In one embodiment, the one or more Amido-Substituted Pyridyl Compounds and the one or more additional therapeutic agents are provided in the same container. In one embodiment, the one or more Amido-Substituted Pyridyl Compounds and the one or more additional therapeutic agents are provided in separate containers.

What is claimed is:

1. A compound of formula (I):

(I)

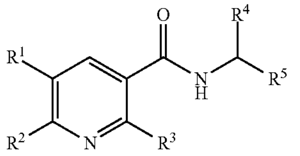

or a pharmaceutically acceptable salt thereof, wherein:

$R^1$ is —O-(5 or 6-membered monocyclic heterocycloalkyl), or —O-(9 or 10-membered bicyclic heterocycloalkyl), wherein said 5 or 6-membered monocyclic heterocycloalkyl group, and said 9 or 10-membered bicyclic heterocycloalkyl group, may each be optionally substituted with one or more $R^A$ groups, which can be the same or different;

$R^2$ is selected from H, $C_1$-$C_6$ alkyl, $C_1$-$C_6$ hydroxyalkyl, —($C_1$-$C_6$ alkylene)$_m$-N($R^4$)$_2$, $C_3$-$C_6$ monocyclic cycloalkyl, 6 to 10-membered bicyclic cycloalkyl, 3 to 7-membered monocyclic heterocycloalkyl, 6 to 10-membered bicyclic heterocycloalkyl, —($C_1$-$C_6$ alkylene)$_m$-(5 or 6-membered monocyclic heteroaryl), and 9 or 10-membered bicyclic heteroaryl, wherein said $C_3$-$C_6$ monocyclic cycloalkyl group, said 6 to 10-membered bicyclic cycloalkyl group, said 3 to 7-membered monocyclic heterocycloalkyl group, said 6 to 10-membered bicyclic heterocycloalkyl group, said 5 or 6-membered monocyclic heteroaryl group, and said 9 or 10-membered bicyclic heteroaryl group may each be optionally substituted with one or more $R^B$ groups, which can be the same or different, or $R^2$ is:

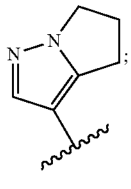;

$R^3$ is —O—($C_1$-$C_6$ alkyl), —($C_1$-$C_6$ alkylene)-O—($C_1$-$C_6$ alkyl), —O—($C_1$-$C_6$ hydroxyalkyl), —O—($C_1$-$C_6$ cyanoalkyl), —O—($C_1$-$C_6$ alkylene)-($C_3$-$C_7$ cycloalkyl), —O—($C_1$-$C_6$ alkylene)-N($R^4$)$_2$, —O—($C_1$-$C_6$ alkylene)-C(O)N($R^4$)$_2$, —O—($C_1$-$C_6$ haloalkyl), —O—($C_1$-$C_6$ alkylene)-(3 to 7-membered monocyclic heterocycloalkyl), —O—($C_1$-$C_6$ alkylene)-(5 or 6-membered monocyclic heteroaryl), wherein said 3 to 7-membered monocyclic heterocycloalkyl group, said 5 or 6-membered monocyclic heteroaryl group, and said 3 to 7 membered cycloalkyl group may each be optionally substituted with one or more $R^D$ groups, which can be the same or different;

each occurrence of $R^4$ is independently H or $C_1$-$C_6$ alkyl;

$R^5$ is phenyl, which may be optionally substituted with one or more $R^C$ groups, which can be the same or different;

each occurrence of $R^A$ is independently selected from $C_1$-$C_6$ alkyl, oxo, and —C(O)—$C_1$-$C_6$ alkyl;

each occurrence of $R^B$ is independently selected from $C_1$-$C_6$ alkyl, —O—($C_1$-$C_6$ alkyl), —OH, oxo, halo, —C(O)H, $C_1$-$C_6$ haloalkyl, $C_1$-$C_6$ hydroxyalkyl, $C_3$-$C_6$ monocyclic cycloalkyl, —($C_1$-$C_6$ alkylene)$_m$-(5 or 6-membered monocyclic heteroaryl), —($C_1$-$C_6$ alkylene)$_m$-N($R^4$)$_2$, —($C_1$-$C_6$ alkylene)$_m$-C(O)N($R^4$)$_2$, and —($C_1$-$C_6$ alkylene)-O—($C_1$-$C_6$ alkyl);

$R^C$ represents up to 3 one or more optional phenyl group substituents, which can be the same or different, and are each independently selected from $C_1$-$C_6$ alkyl, halo, —$C_1$-$C_6$ haloalkyl, and —CN;

each occurrence of $R^D$ is independently selected from $C_1$-$C_6$ alkyl, oxo, halo, —$C_1$-$C_6$ haloalkyl, and —CN; and each occurrence of m is independently 0 or 1.

2. The compound of claim 1, or a pharmaceutically acceptable salt thereof, wherein $R^1$ is selected from:

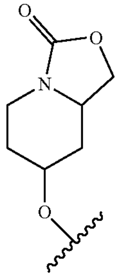,

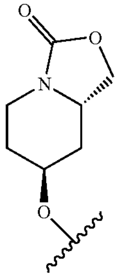,

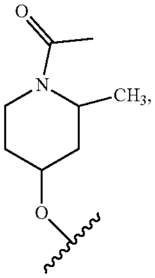

and

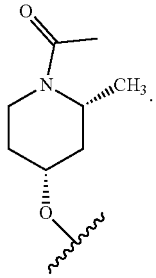.

3. The compound of claim 2, or a pharmaceutically acceptable salt thereof, wherein $R^1$ is:

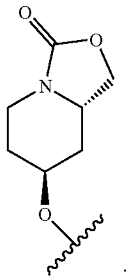 [SMILES: *O[C@H]1CCN2C(=O)OC[C@@H]2C1]

.

4. The compound of claim 1, or a pharmaceutically acceptable salt thereof, wherein $R^5$ is selected from:

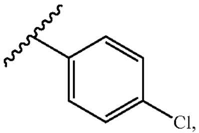
Cl,
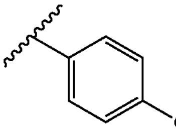
CN,
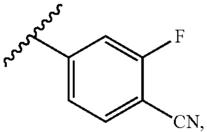
CN,
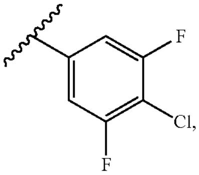
Cl,
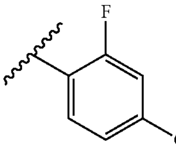
CN, and
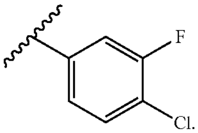
Cl.

5. The compound of claim 4, or a pharmaceutically acceptable salt thereof, wherein $R^5$ is:

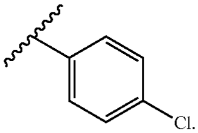 [SMILES: *c1ccc(Cl)cc1]
Cl.

6. The compound of claim 1, or a pharmaceutically acceptable salt thereof, wherein $R^4$ is H.

7. The compound of claim 1, wherein $R^2$ is selected from H, methyl, $-CH_2C(CH_3)_2NH_2$, $CH_2C(CH_3)_2OH$, pyrazolyl, furanyl, benzofuranyl, indolyl, pyridyl, azetidinyl, pyrrolidinyl, isoxazolyl, thiphenyl, thiazolyl, pyridizanyl, pyrimidinyl, cyclopropyl, cyclobutyl, oxazolyl, spiro[3,3]heptane, 1,2,4-oxadiazolyl, 1,3,4-thiadiazolyl,

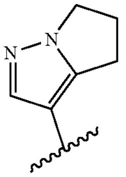
,
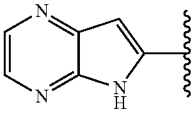
,
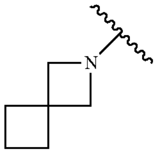
,

-continued

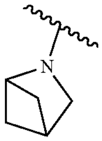
, and
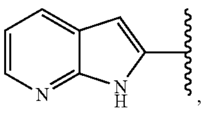
, wherein said pyrazolyl, furanyl, benzofuranyl, indolyl, pyridyl, azetidinyl, pyrrolidinyl, isoxazolyl, thiophenyl, thiazolyl, pyridizanyl, pyrimidinyl, cyclopropyl, cyclobutyl, oxazolyl, spiro[3,3]heptane, 1,2,4-oxadiazolyl, 1,3,4-thiadiazolyl,

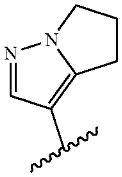
,
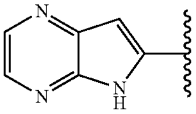
,
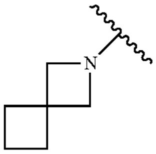
,
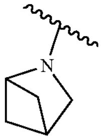
, and
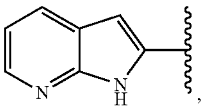
, may be optionally substituted with up to three groups, which can be the same or different, and are selected from $-CHF_2$, methyl, ethyl, cyclopropyl, —OH, C(O)H, pyrazolyl, $-CH_2$-pyridyl, $-NH_2$, F, $-CF_3$, $-CH_2OH$, $-CH_2CH_2OH$, $-CH_2CH_2OCH_3$, methoxy, and $-C(OH)(CH_3)_2$.

8. The compound of claim 7, or a pharmaceutically acceptable salt thereof, wherein $R^2$ is:

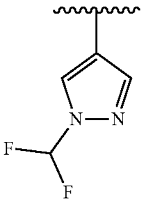

.

9. The compound of claim 1, or a pharmaceutically acceptable salt thereof, wherein $R^3$ is selected from methoxy, ethoxy, $-OCH_2CH_2OH$, $-OCH_2CH_2OCH_3$, $-OCH_2CH_2N(CH_3)_2$, $-OCH_2C(OH)(CH_3)_2$, $-OCH_2CH_2F$, $-OCH_2C(CN)(CH_3)_2$, $-OCH_2CH(CH_3)OH$, $-OCH_2CH_2CH_2N(CH_3)_2$, $-OCH_2C(CN)(CH_3)_2$, $-OCH_2CH(OH)(CH_3)$, $-OCH_2CH_2N(CH_2CH_3)_2$, $-OCH_2CH_2C(O)NH_2$,

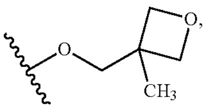
,
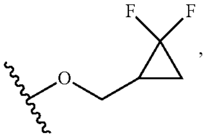
,

-continued
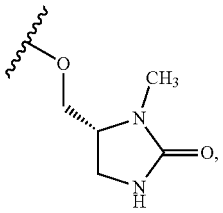
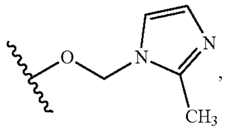
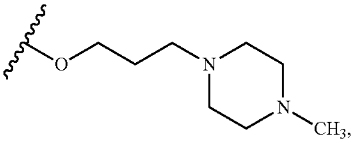
and
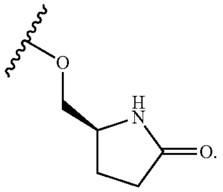
10. The compound of claim 9, or a pharmaceutically acceptable salt thereof, wherein $R^3$ is methoxy.
11. The compound of claim 7, or a pharmaceutically acceptable salt thereof wherein:
$R^1$ is:
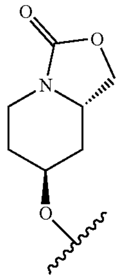
;
and
$R^3$ is —O—($C_1$-$C_6$ alkyl).
12. A compound having the structure:
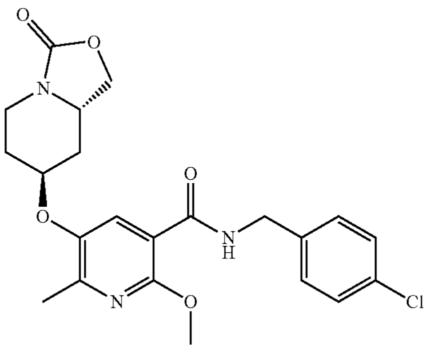
-continued
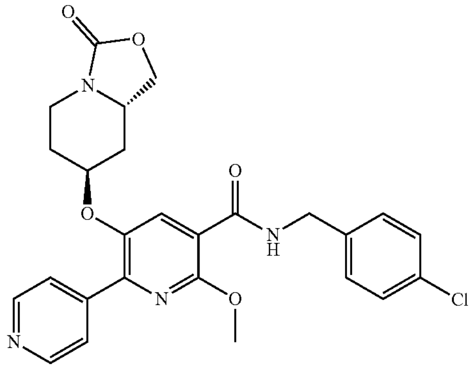
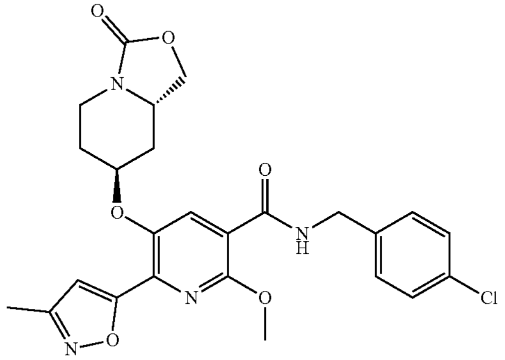
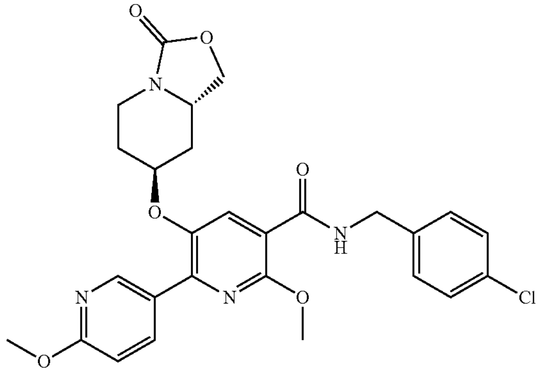
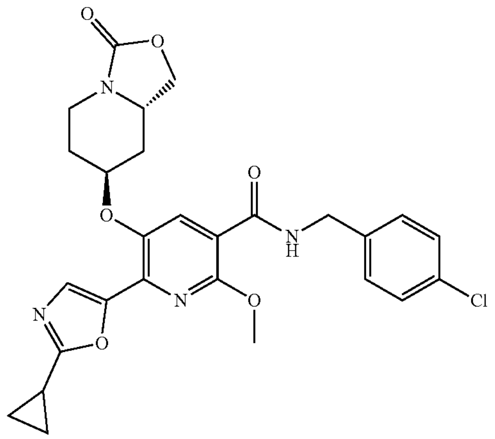

-continued
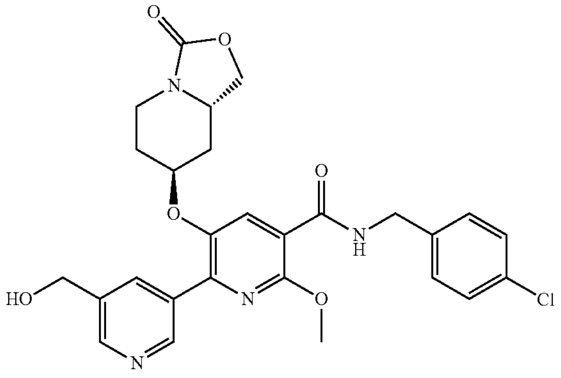
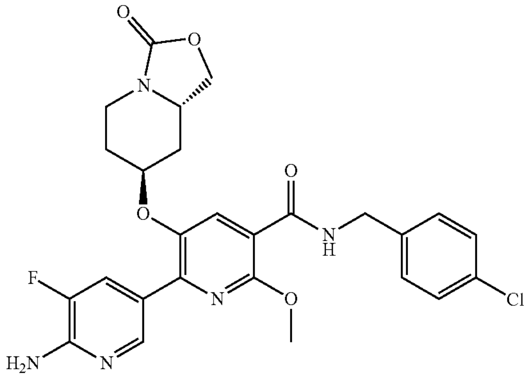
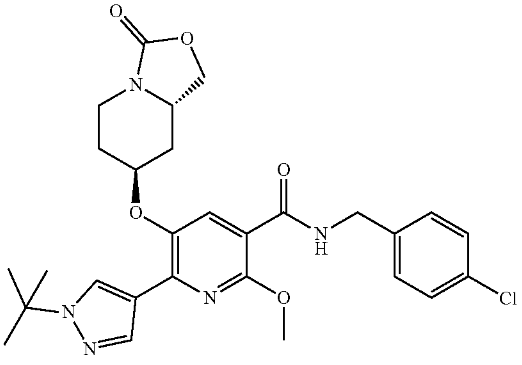
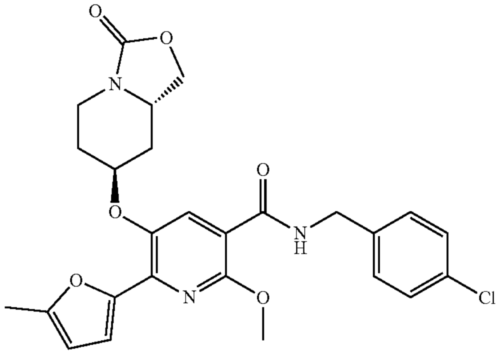
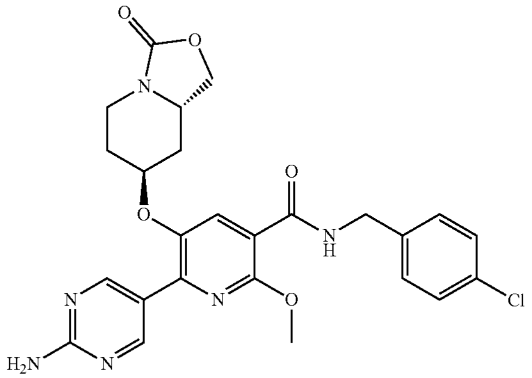
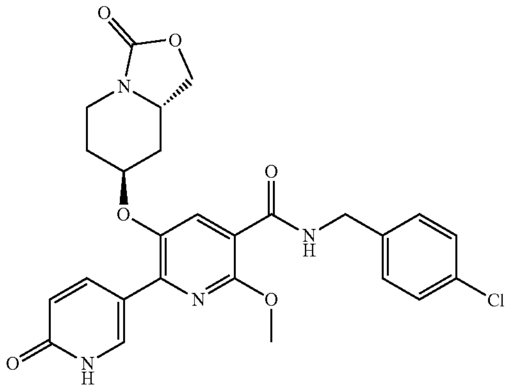
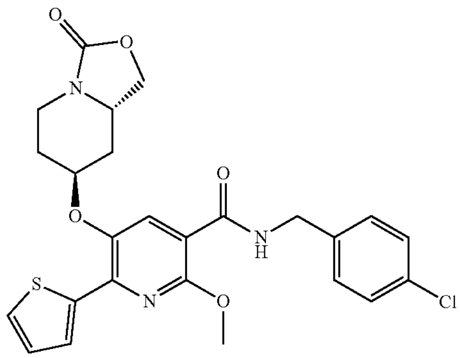
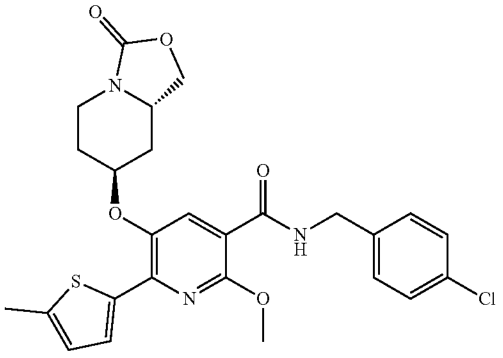
-continued -continued
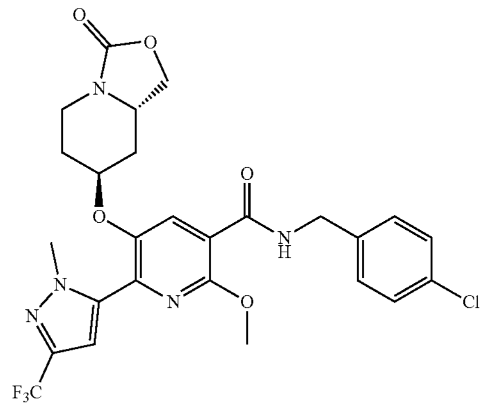
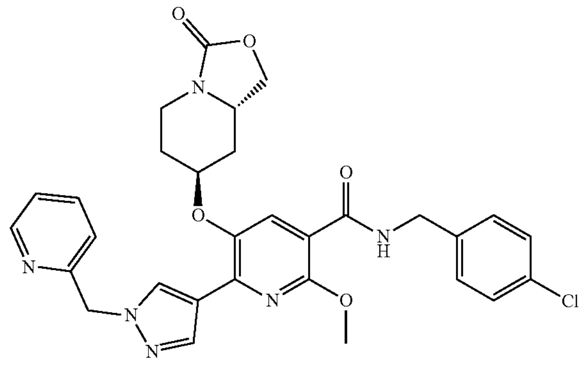
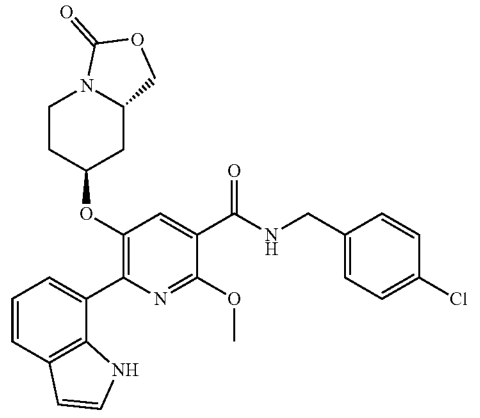
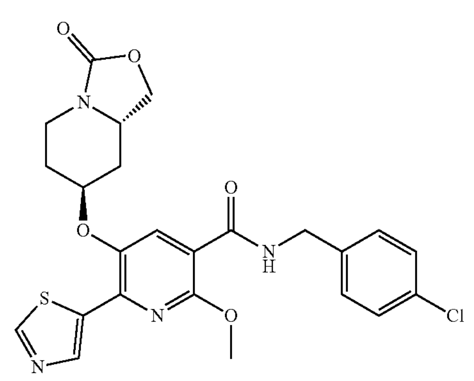
-continued
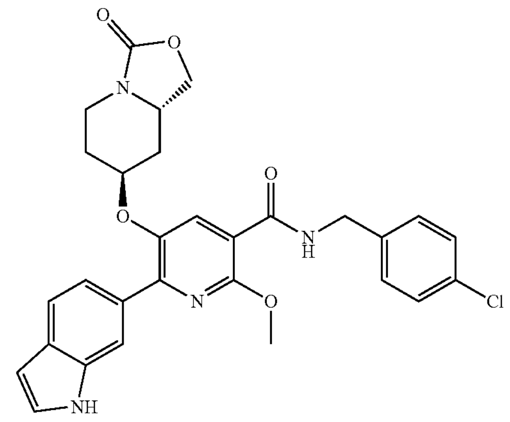
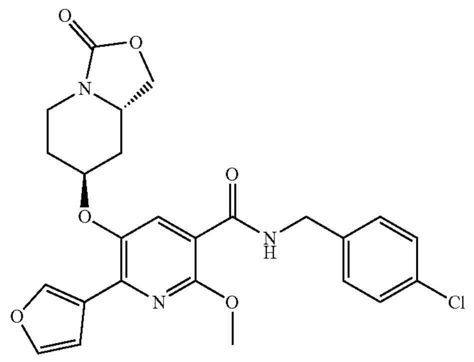
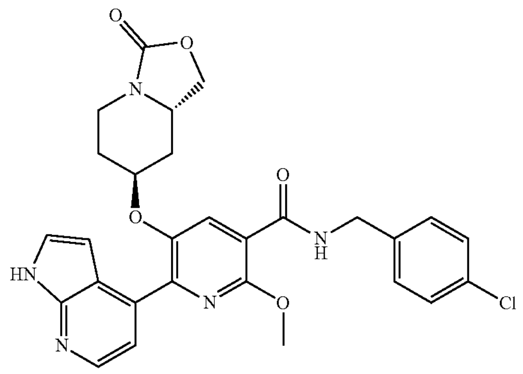
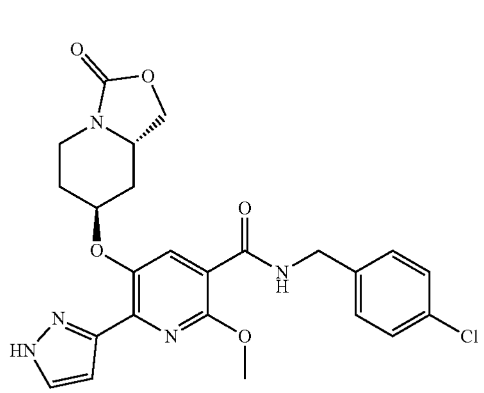

-continued
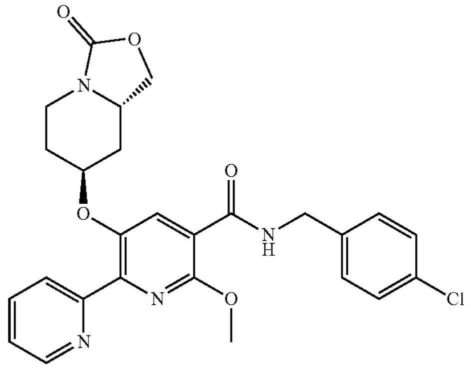
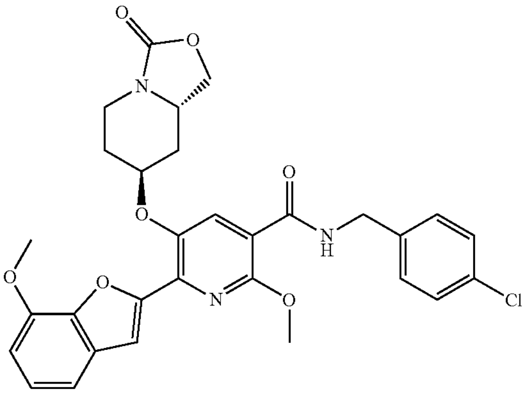
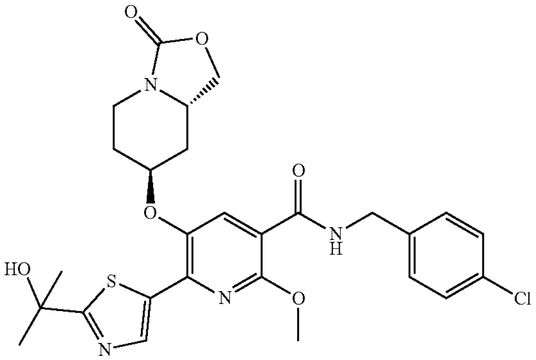
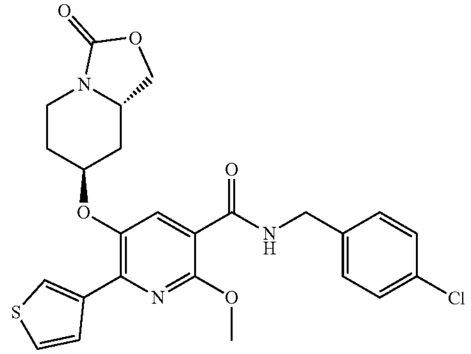
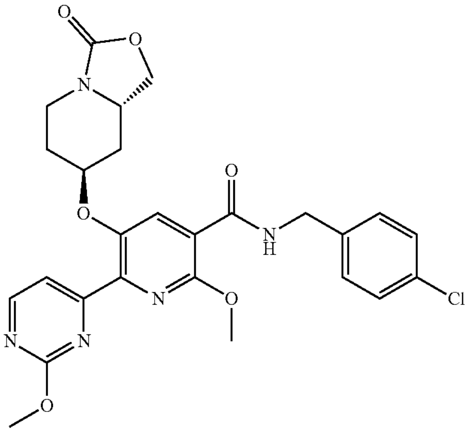
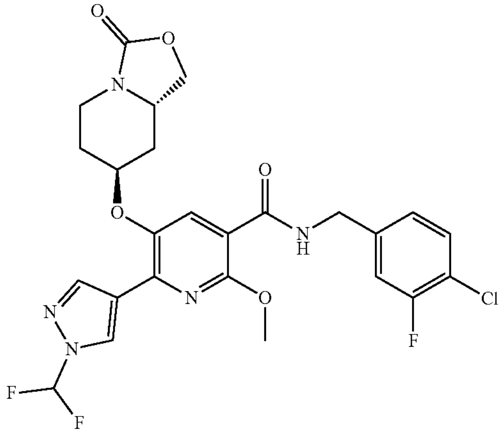
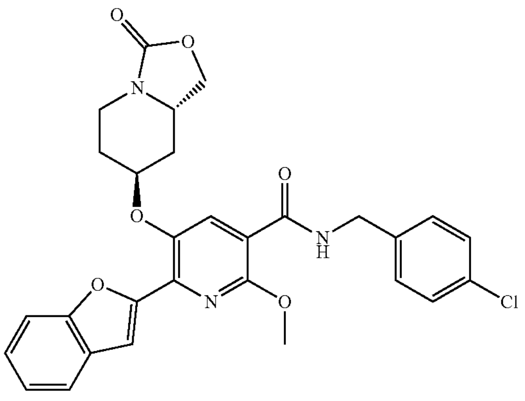
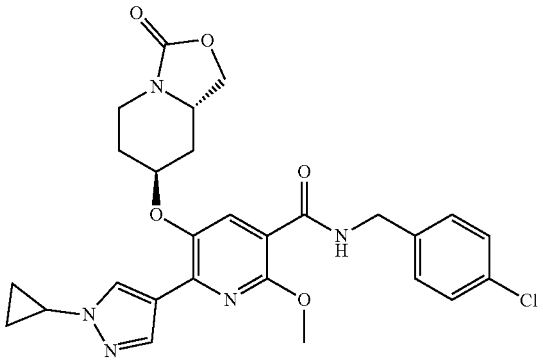

-continued
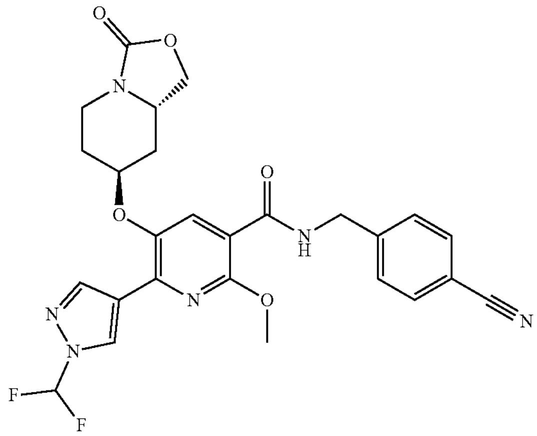
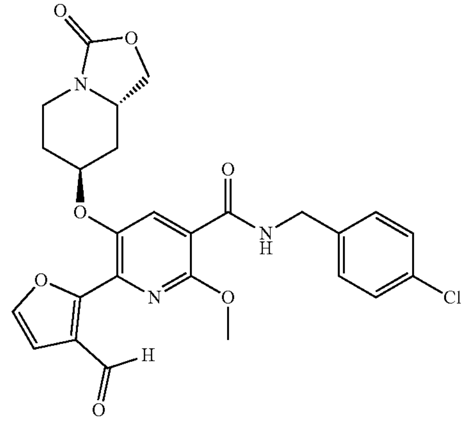
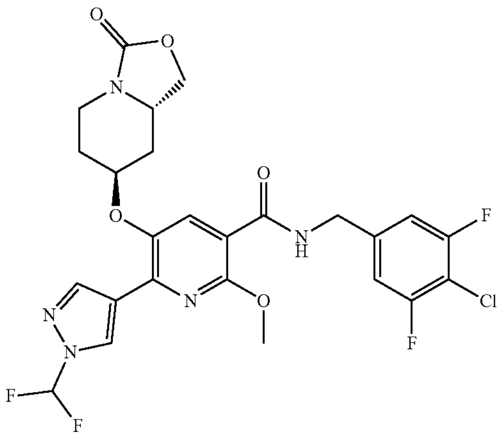
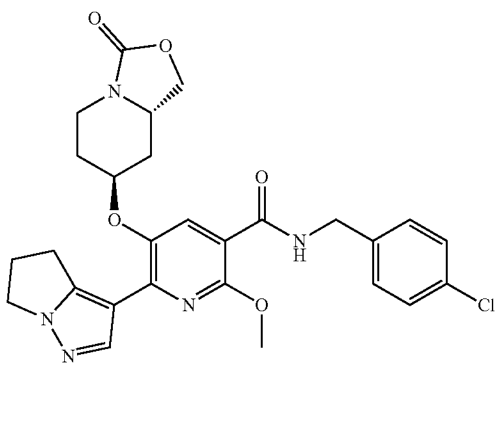
-continued
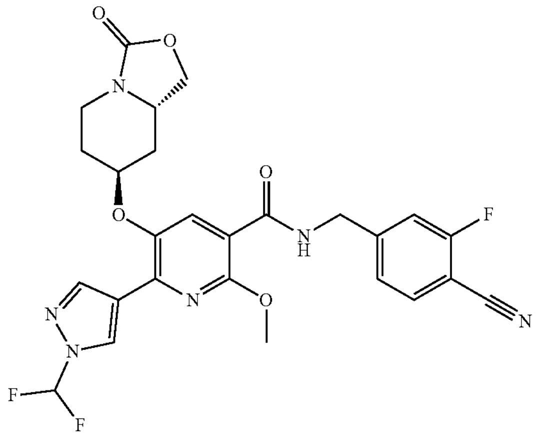
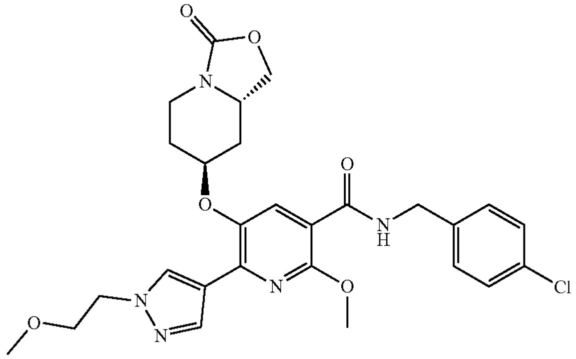
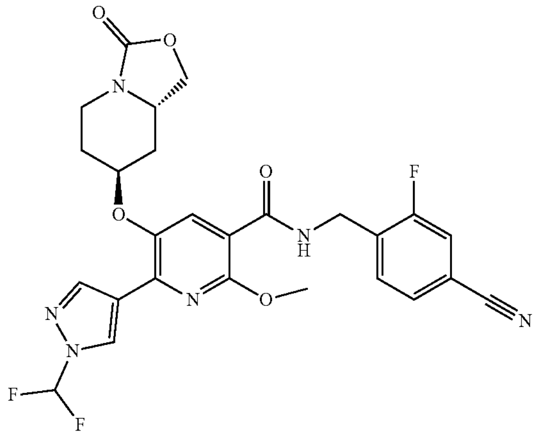
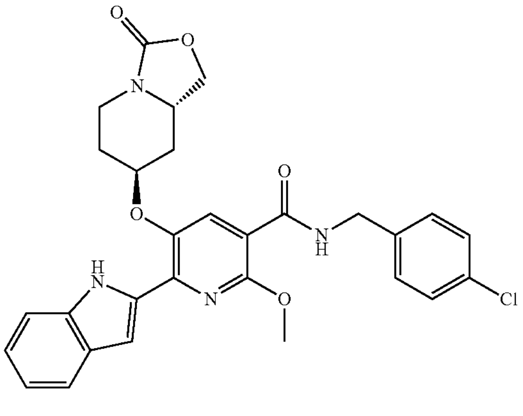

-continued
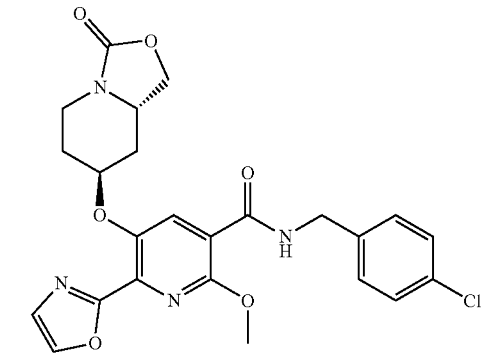
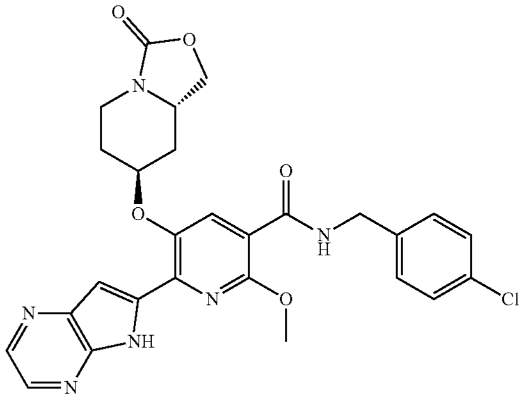
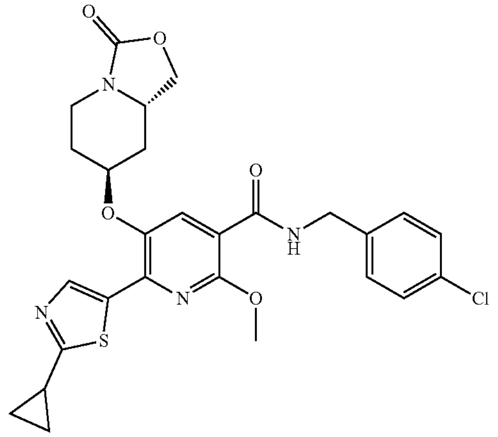
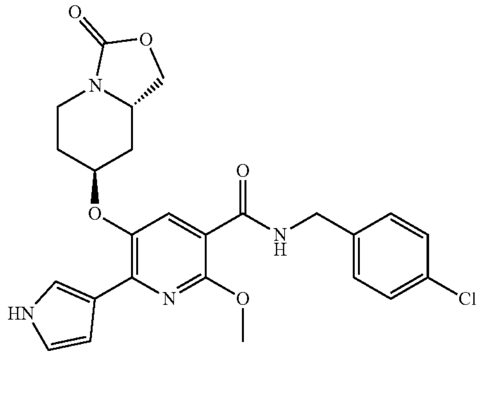
-continued
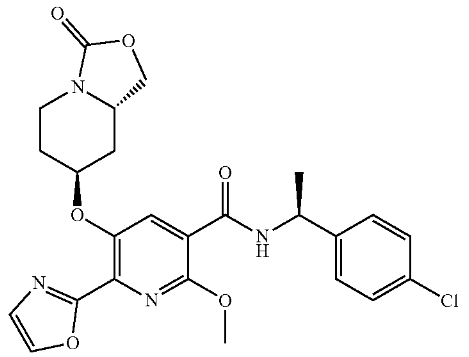
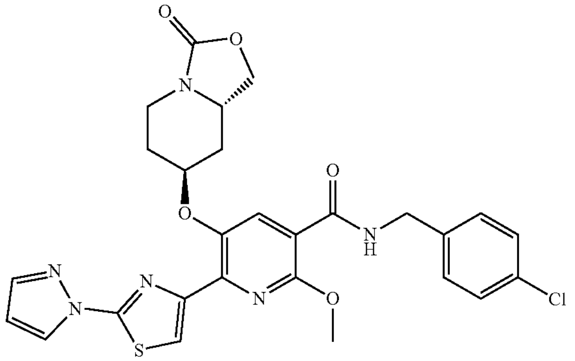
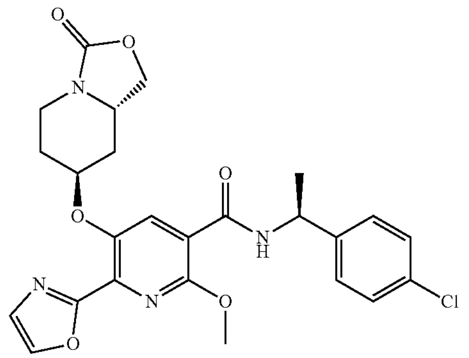
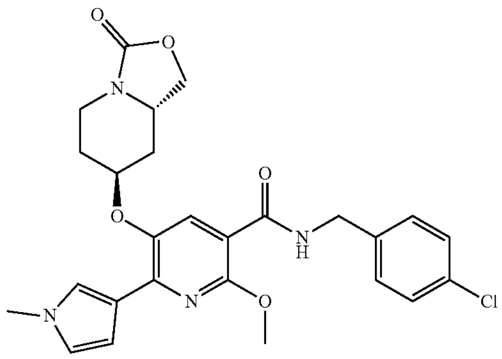

-continued
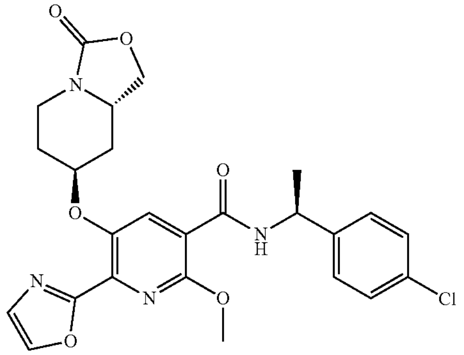
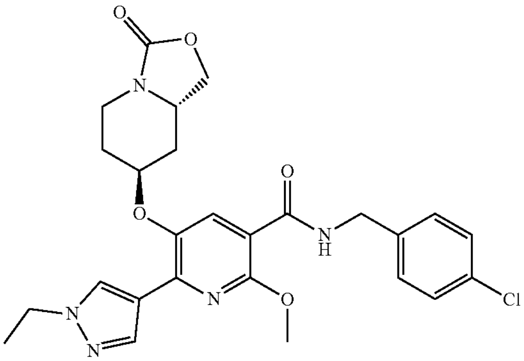
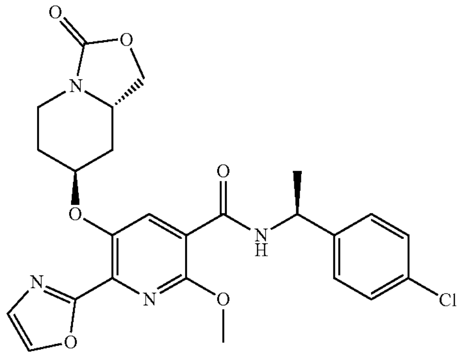
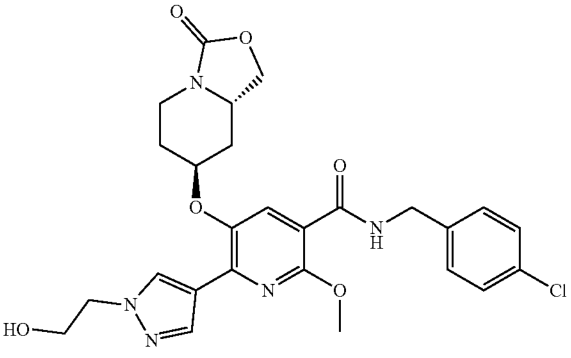
-continued
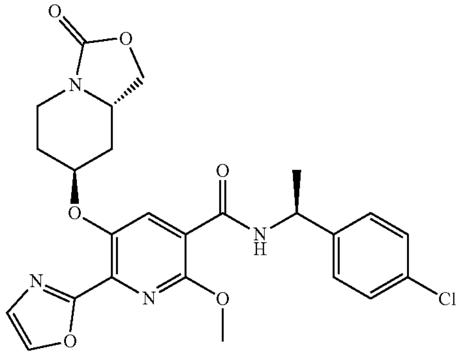
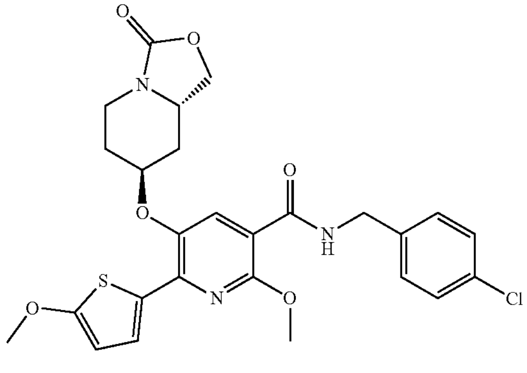
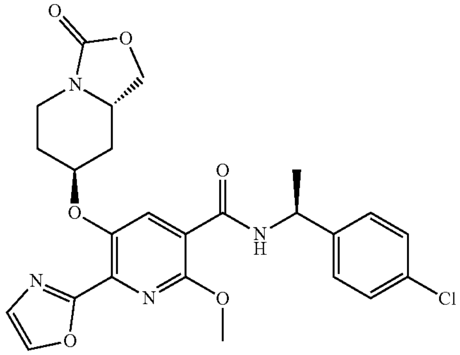
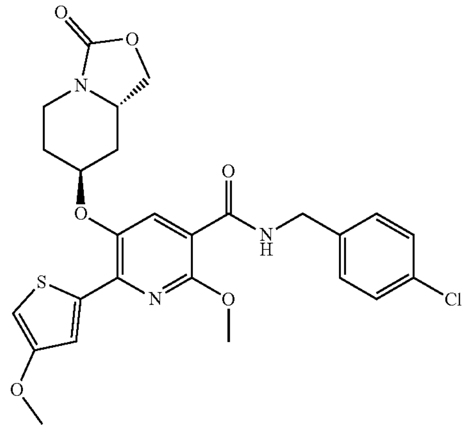

-continued
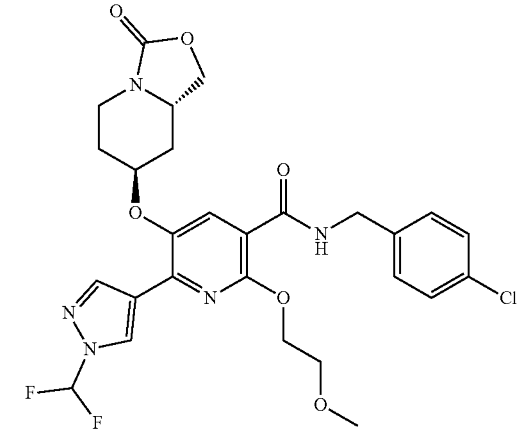
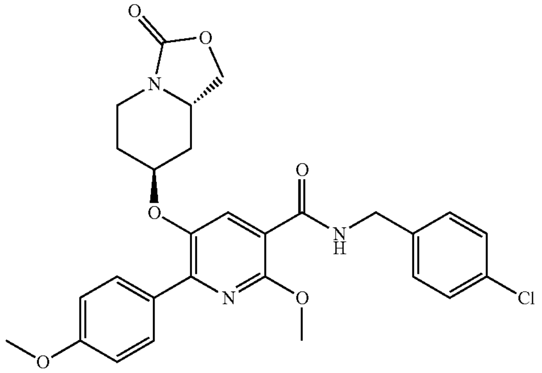
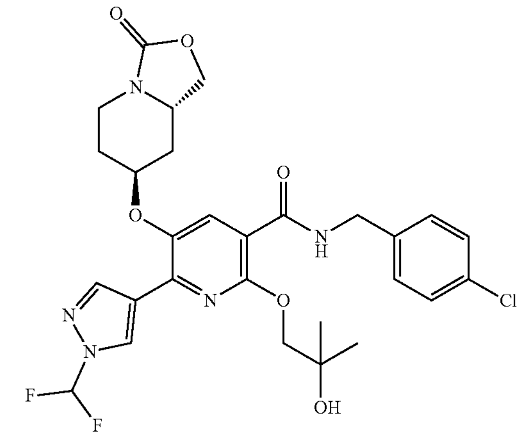
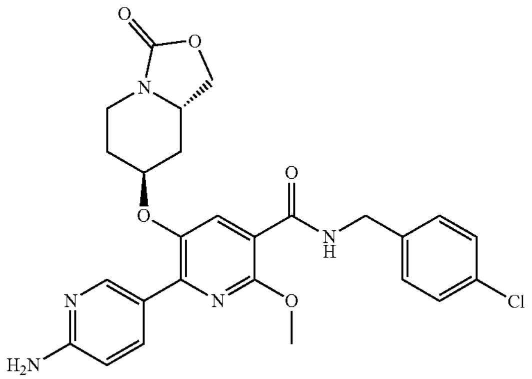
-continued
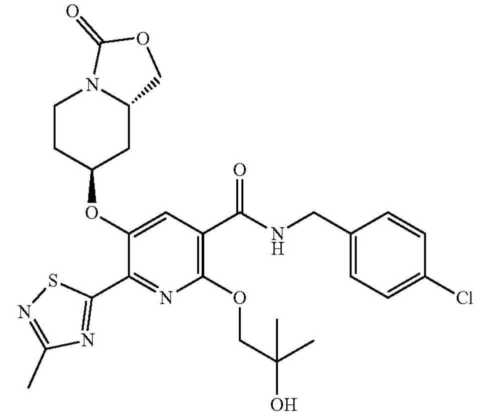
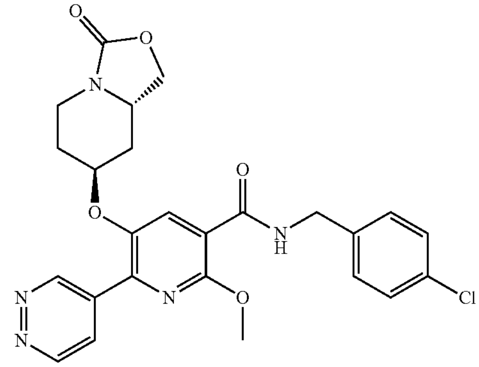
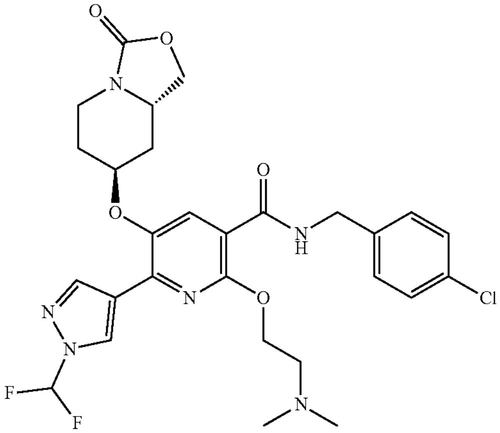
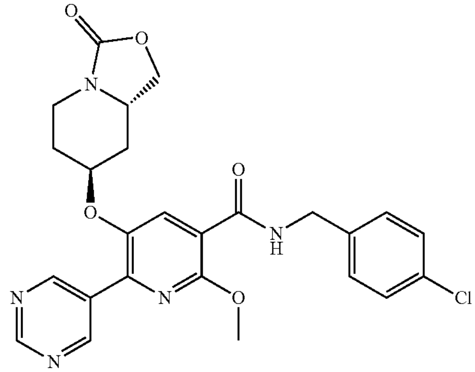

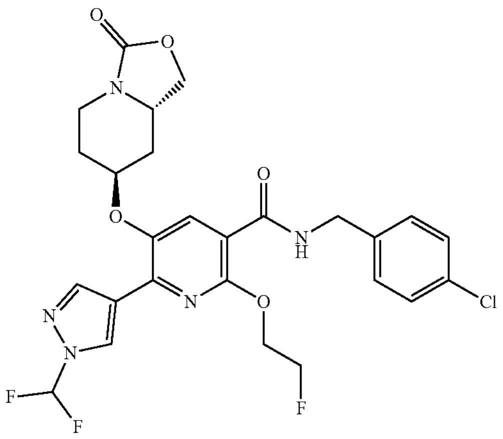
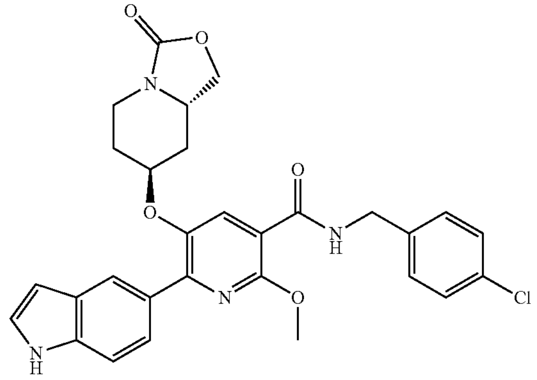
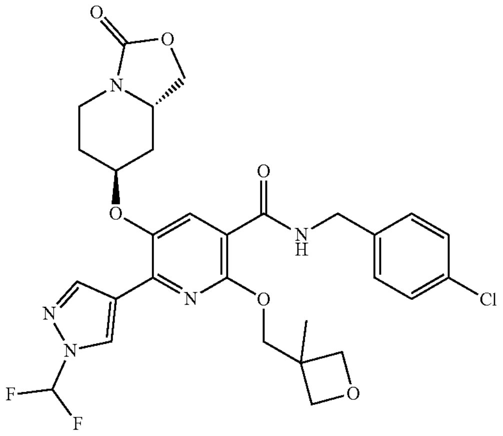
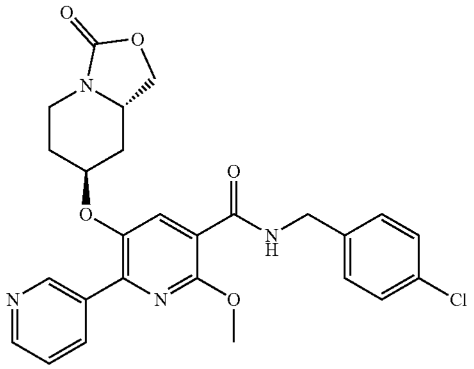
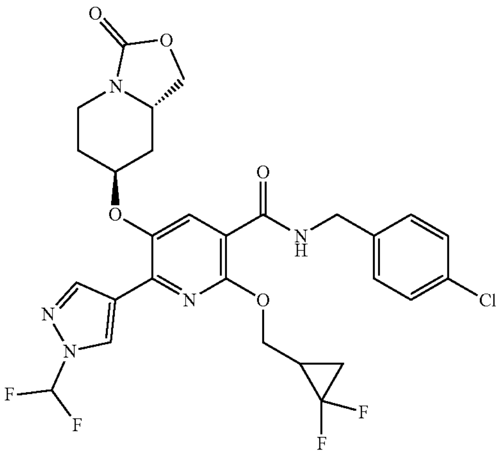
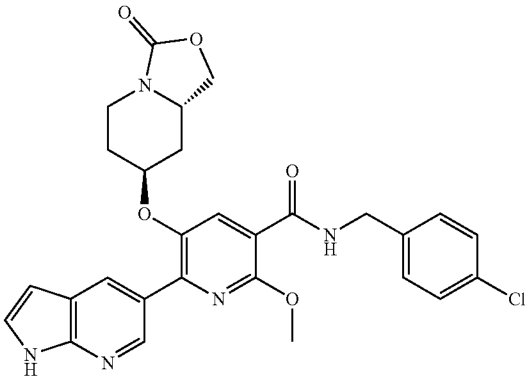
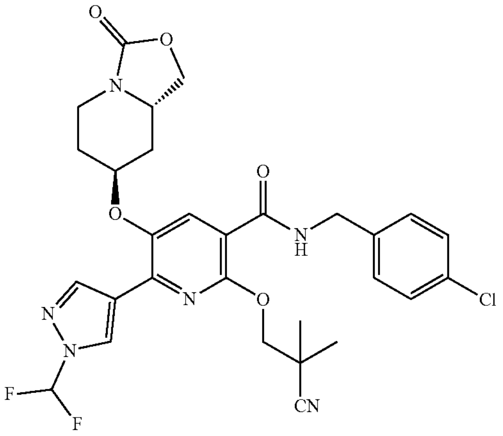
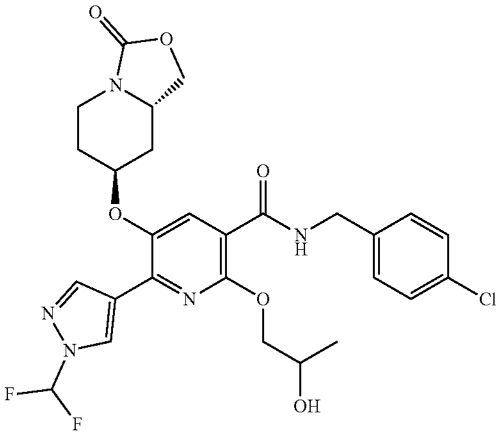

-continued
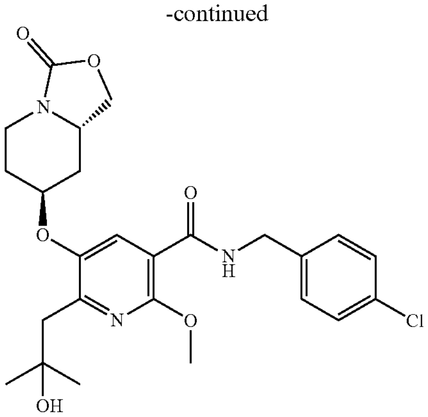
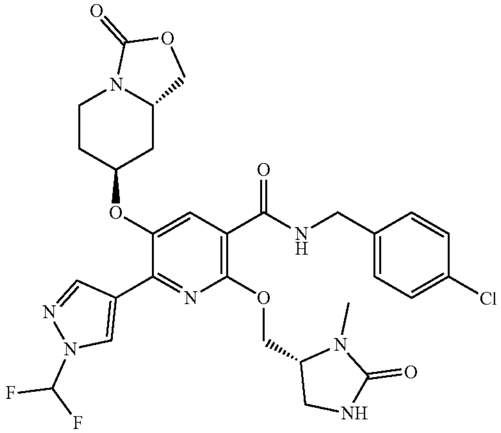
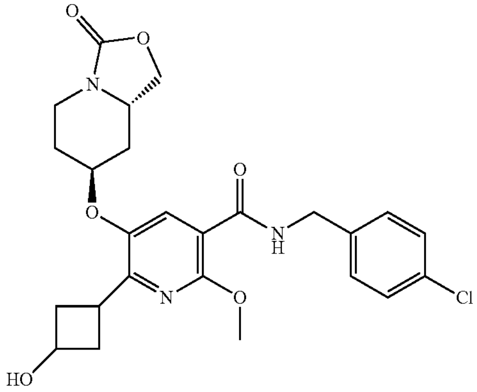
cis
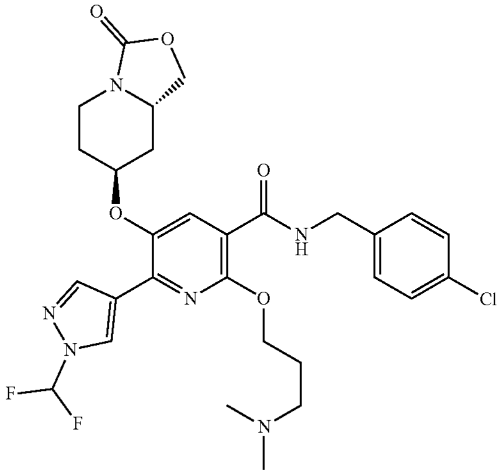
-continued
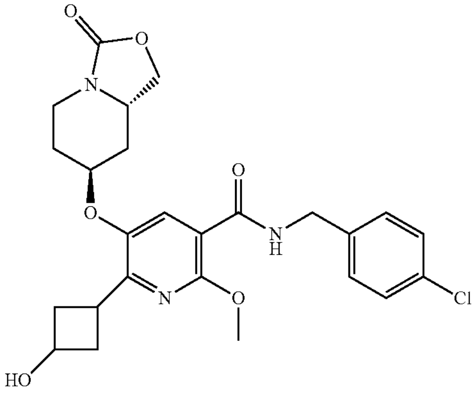
trans
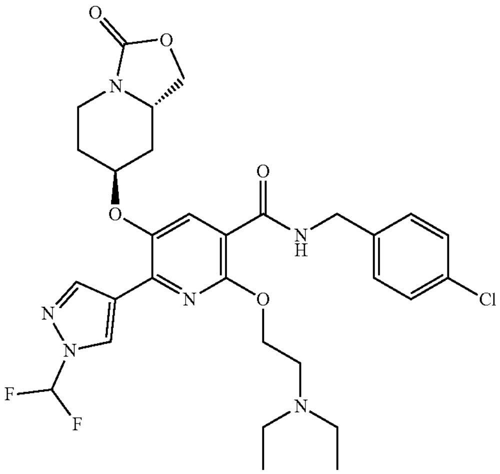
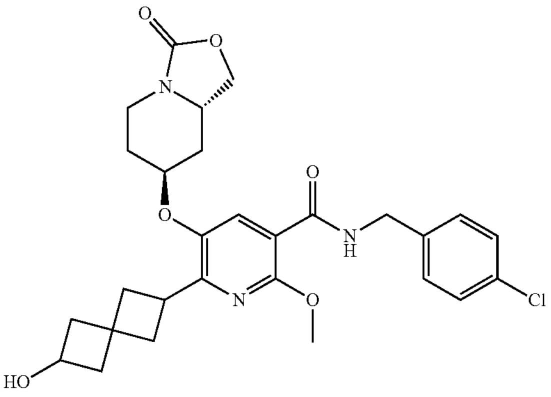

-continued
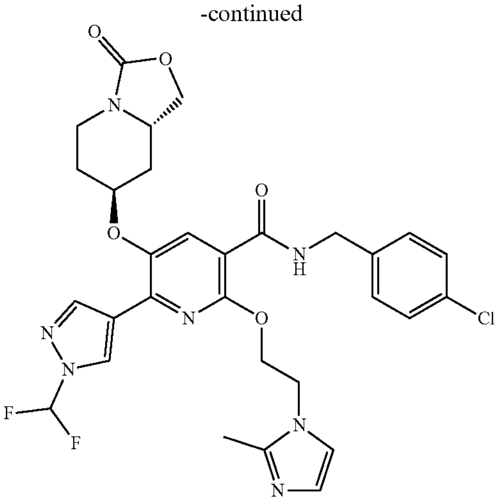
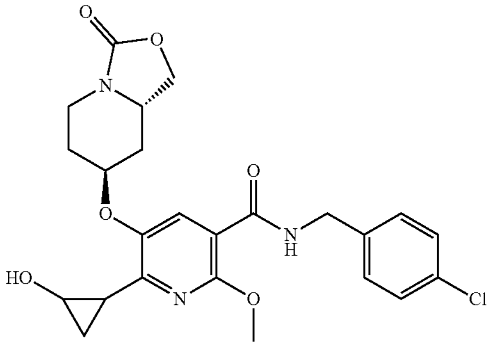
Isomer 3
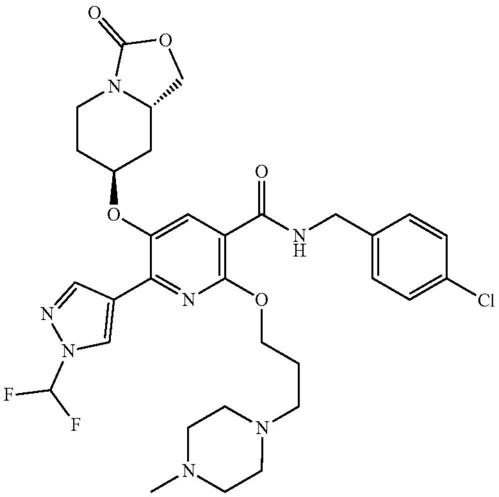
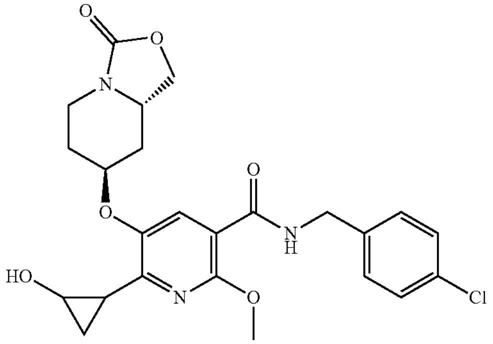
Isomer 2
-continued
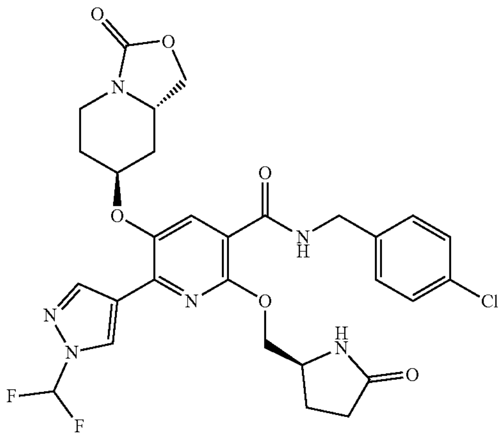
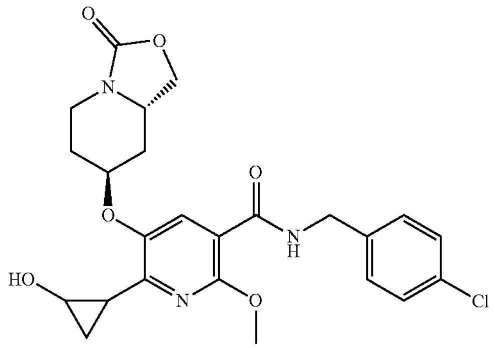
Isomer 3
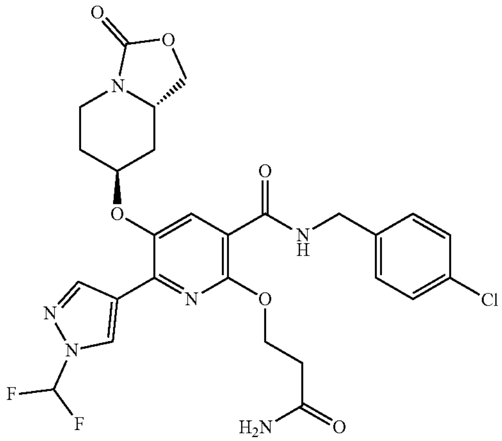
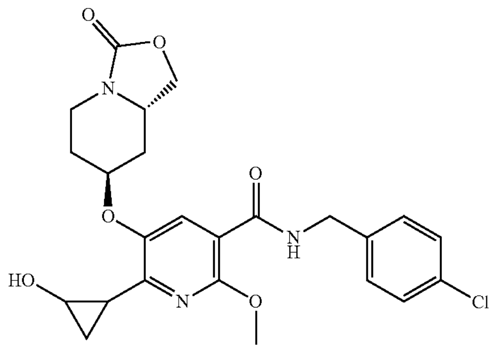
Isomer 4

-continued
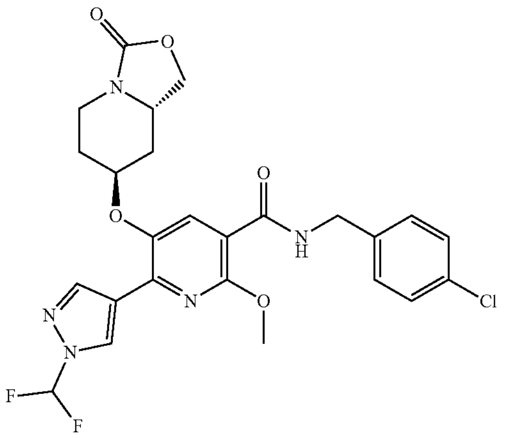
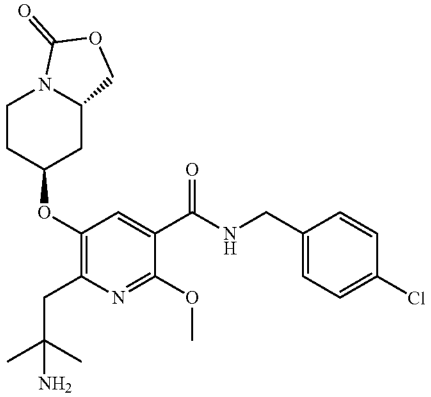
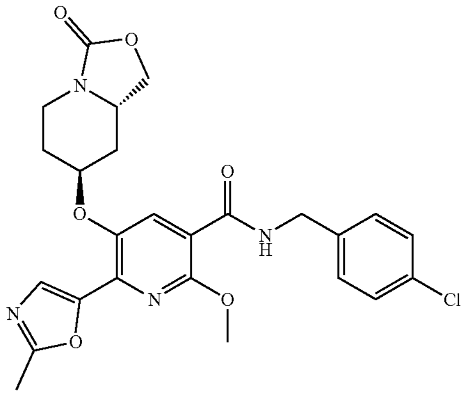
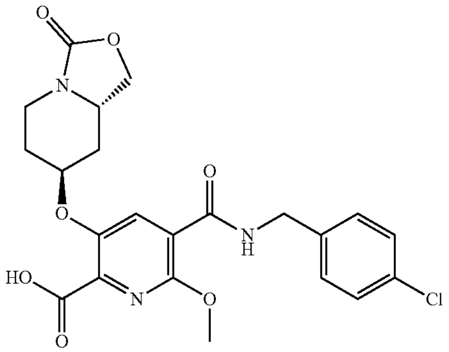
-continued
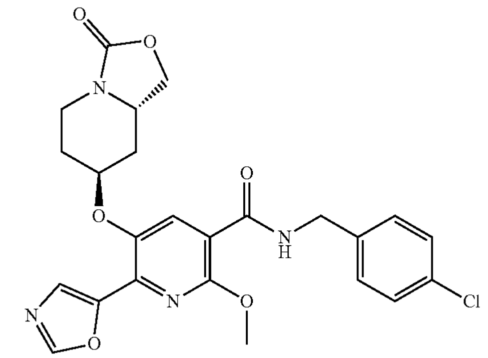
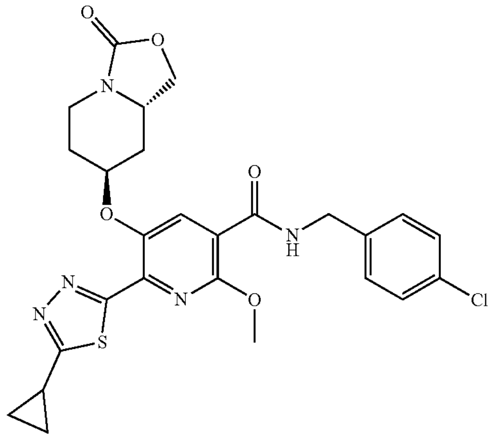
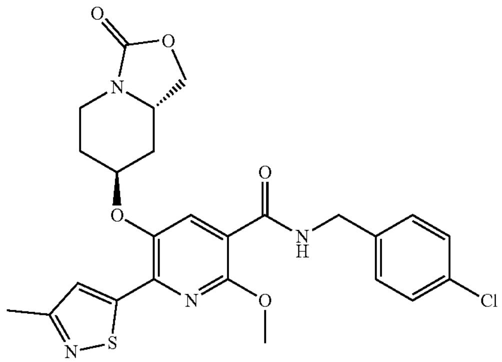
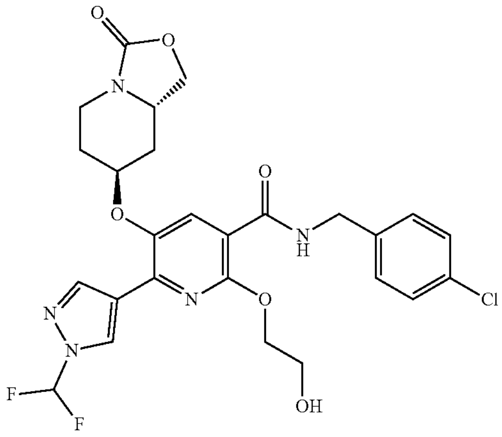

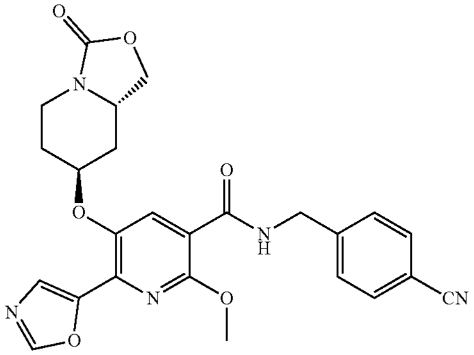
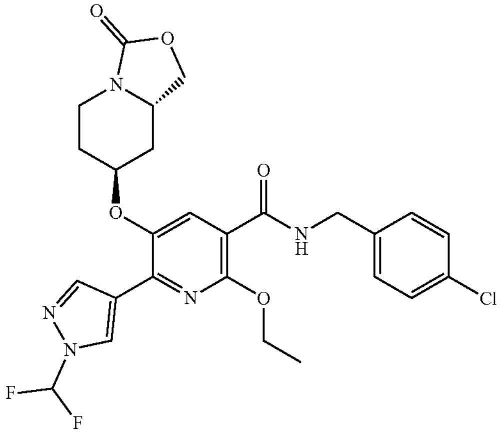
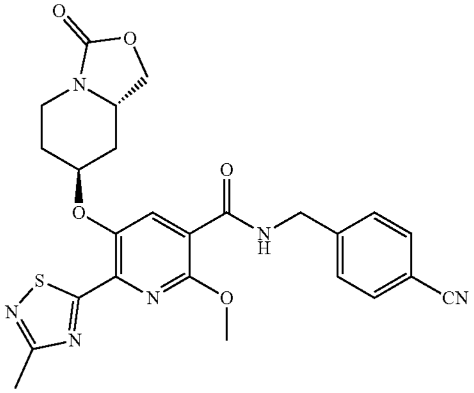
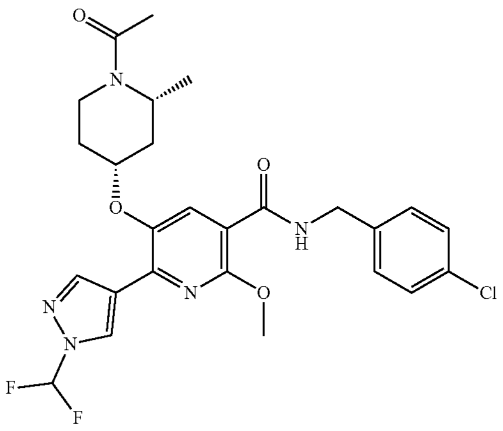
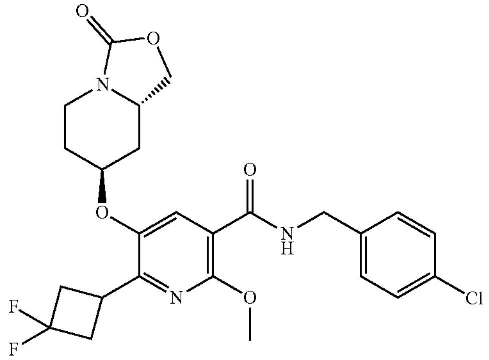
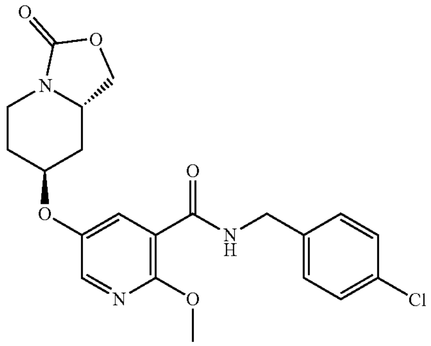
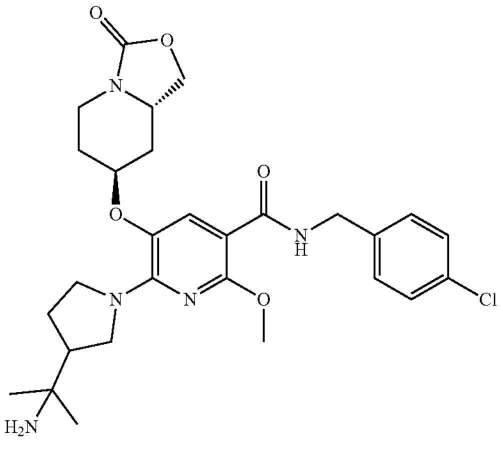
(R or S)
Isomer 1

-continued

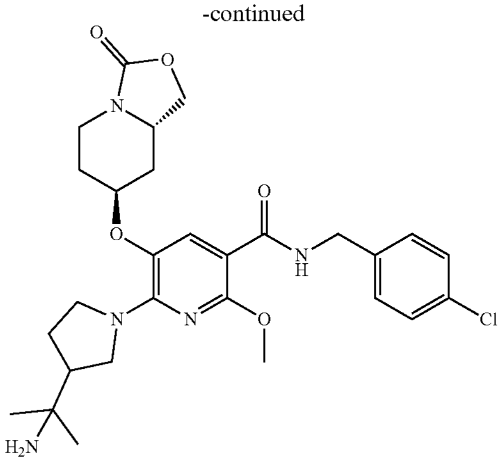

(R or S)
Isomer 2 or a pharmaceutically acceptable salt thereof.

13. A pharmaceutical composition comprising an effective amount of the compound of claim 1, or a pharmaceutically acceptable salt thereof, and a pharmaceutically acceptable carrier.

14. The pharmaceutical composition of claim 13 further comprising one or more additional therapeutic agents, wherein said additional therapeutic agents are selected from anti-herpes agents, and immunomodulators.

15. A method of treating a patient infected with a herpesvirus, comprising the step of administering an amount of the compound of claim 1, or a pharmaceutically acceptable salt thereof, effective to treat infection by said herpesvirus in said patient.

16. The method of claim 15, further comprising administering one or more additional therapeutic agents, wherein said additional therapeutic agents are selected from anti-herpes agents, and immunomodulators.

17. The pharmaceutical composition of claim 14, wherein said additional therapeutic agents comprise letermovir.

18. The method of claim 16, wherein said additional therapeutic agents comprise letermovir.

* * * * *